(12) United States Patent
Goeddel et al.

(10) Patent No.: US 6,610,830 B1
(45) Date of Patent: *Aug. 26, 2003

(54) MICROBIAL PRODUCTION OF MATURE HUMAN LEUKOCYTE INTERFERONS

(75) Inventors: David V. Goeddel, Burlingame, CA (US); Sidney Pestka, North Caldwell, NJ (US)

(73) Assignees: Hoffman-La Roche Inc., Nutley, NJ (US); Genentech, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 06/256,204

(22) Filed: Apr. 21, 1981

Related U.S. Application Data

(63) Continuation-in-part of application No. 06/205,578, filed on Nov. 10, 1980, now abandoned, which is a continuation-in-part of application No. 06/184,909, filed on Sep. 8, 1980, now abandoned, which is a continuation-in-part of application No. 06/164,986, filed on Jul. 1, 1980, now abandoned.

(51) Int. Cl.$^7$ .............................................. C07K 14/56
(52) U.S. Cl. ................. 530/351; 435/69.51; 536/23.52
(58) Field of Search ....................... 260/112.5 R, 112 R; 424/85, 85.7; 435/172.3, 68, 69.51, 84; 530/351

(56) References Cited

U.S. PATENT DOCUMENTS

| | | | |
|---|---|---|---|
| 4,289,690 A | * 9/1981 | Pestka et al. ................. 424/85 |
| 4,332,892 A | 6/1982 | Ptashne et al. ............. 435/69.7 |
| 4,342,832 A | 8/1982 | Goeddel et al. .......... 435/91.41 |
| 4,418,149 A | 11/1983 | Ptashne et al. ........ 435/252.33 |
| 4,503,035 A | 3/1985 | Pestka et al. ............... 424/85.7 |
| 4,530,901 A | 7/1985 | Weissmann ............... 435/69.51 |
| 4,801,685 A | 1/1989 | Goeddel et al. .......... 435/69.51 |
| 4,810,645 A | 3/1989 | Goeddel et al. .......... 435/69.51 |

FOREIGN PATENT DOCUMENTS

| | | |
|---|---|---|
| EP | 0 001 929 | 6/1979 |
| EP | 8030110.6 | 4/1980 |
| EP | 0 006 694 | 10/1983 |
| GB | 2007676 | 5/1979 |
| GB | 2055382 | 3/1981 |

OTHER PUBLICATIONS

Torma and Paucher, J. Biol Chem., vol. 254, pp. 4810–4816, 1976.*
Taniguchi et al., Nature, vol. 285, pp. 547–549, 1980.*
Rubenstein et al., Proc. Natl. Acad. Sci., vol. 76, pp. 640–644, 1979.*
Montei et al., Gene, vol. 10, pp. 1–10, 1980.*
Nagata et al., Nature, vol. 284, pp. 316–320, 1980.*
Levy, W., et al., Proc. Natl. Acad. Sci, vol. 78, pp. 6186–6190, 1981.*
Guarente, L., et al., Science, vol. 209, 1980.*
Cohen, Scientific American, Jul. 1975, pp. 25–33.*
Allen, 1982, "Structure and properties of human interferon–α from Namalwa lymphoblastoid cells," *Biochem. J.* 207:397–408.
Allen and Fantes, 1980, "A family of structural genes for human lymphoblastoid (leukocyte–type) interferon," *Nature* 287:408–411.
Anfinsen, 1981, "Human interferon," *Interdisciplinary Science Reviews* 6(2):110–118.
Backman and Ptashne, 1978, "Maximizing gene expression on a plasmid using recombination in vitro," *Cell* 13(1):65–71.
Bolivar et al., 1977, "Construction and characterization of new cloning vehicles. II. A multipurpose cloning system," *Gene* 2(2):95–113.
Cavalieri et al., 1977, "Synthesis of human interferon by *Xenopus laevis* oocytes: two structural genes for interferons in human cells," *Proc. Natl. Acad. Sci. U.S.A.* 74(8):3287–3291.
Chang et al., 1978, "Phenotypic expression in *E. coli* of a DNA sequence coding for mouse dihydrofolate reductase," *Nature* 275(5681):617–624.
Crea et al., 1978, "Chemical synthesis of genes for human insulin," *Proc. Natl. Acad. Sci. U.S.A.* 75(12):5765–5769.
Derynck et al., 1980, "Isolation and structure of a human fibroblast interferon gene," *Nature* 285(5766):542–547.
Derynck et al., 1980, "Expression of human fibroblast interferon gene in *Escherichia coli*," *Nature* 287(5779):193–197.
Goeddel et al., 1989, "The structure of eight distinct cloned human leukocyte interferon cDNAs," *Nature* 290(5801):20–26.
Goeddel et al., 1980, "Human leukocyte interferon produced by *E. coli* is biologically active," *Nature* 287(5781):411–416.
Goeddel et al., 1980, "Synthesis of Human Fibroblast Interferon by *E. coli*," *Nucleic Acid Research* 8:4057–74.
Goeddel et al., 1979, "Expression in *Escherichia coli* of chemically synthesized genes for human insulin," *Proc. Natl. Acad. Sci. U.S.A.* 76(1):106–110.
Goeddel et al., 1979, "Direct expression in *Escherichia coli* of a DNA sequence coding for humna growth hormone," *Nature* 281(5732):544–548.

(List continued on next page.)

Primary Examiner—James Martinell
(74) Attorney, Agent, or Firm—Pennie & Edmonds LLP

(57) ABSTRACT

Disclosed herein are methods and means of microbially producing, via recombinant DNA technology, mature human leukocyte interferons, useful in the treatment of viral and neoplastic diseases.

46 Claims, 19 Drawing Sheets

OTHER PUBLICATIONS

Green et al., 1976, "Isolation and cell–free translation of immunoglobulin messenger RNA," *Arch. Biochem. Biophys.* 172(1):74–89.

Guarente et al., 1980, "Improved methods for maximizing expression of a cloned gene: a bacterium that synthesizes rabbit beta–globin," *Cell* 20(2):543–553.

Attached are pp. 135–137 of the Main Brief at Final Hearing for Goeddel et al. (including the pages of the record and exhibits cited therein) in Interference No. 101,601, *Goeddel et al. v. Weissman*, re: Heynecker, Speech at NIH Interferon Workshop, Sep. 8–9, 1980.

Houghton, 1980, "Human interferon gene sequences," *Nature* 285 (5766):536.

Itakura et al., 1977, "Expression in *Escherichia coli* of a chemically synthesized gene for the hormone somatostatin," *Science* 198(4321):1056–1063.

Mantei et al., *Chemical Abstracts*, 1980, vol. 93, p. 489, Abstract No. 130319s.

Miller, 1979, "Use of recombinant DNA technology for the production of polypeptides," *Adv. Exp. Med. Biol.* 118:153–174.

Nagata et al., 1980, "The structure of one of the eight or more distinct chromosomal genes for human interferon–alpha," *Nature* 287(5781):401–408.

Nagata et al., *Chemical Abstracts*, 1980, vol. 93, p. 479, Abstract No. 41286m.

Pestka et al., 1987, "Interferons and their actions," *Ann. Rev. Biochem.* 56:727–777.

Prouty et al., 1975, "Degradation of abnormal proteins in *Escherichia coli*: Formation of protein inclusions in cells exposed to amino acid analogs," *J. Biological Chem.* 250(3):1112–1129.

Roberts et al., 1979, "A general method for maximizing the expression of a cloned gene," *Proc. Natl. Acad. Sci. U.S.A.* 76(2):760–764.

Roberts et al., 1979, "Synthesis of simian virus 40 t antigen in *Escherichia coli*," *Proc. Natl. Acad. Sci. U.S.A.* 76(11):5596–5600.

Rubenstein et al., 1981, "Human Leukocye Interferon: Isolation and Characterization of Several Molecular Forms," *Arch. Biochem. Biophys.* 210(1):307–318.

Staehelin et al., 1981, "Production of hybridomas secreting monoclonal antibodies to the human leukocyte interferons," *Proc. Natl. Acad. Sci. U.S.A.* 78(3):1848–1852.

Stebbing et al., "Biological Comparison of Natural and Recombinant DNA–Derived polypeptides," *State of the Art: Insulins and Growth Hormone*. Presentation for FDA Meeting, Jun. 3–4, 1980.

Streuli et al., 1980, "At least three human type α interferons: Structure of α2," *Science* 209:1343–1347.

Taniguchi et al., 1980, "Expression of the human fibroblast interferon gene in *Escherichia coli*," *Proc. Natl. Acad. Sci. U.S.A.* 77(9):5230–5233.

Transcript of Tape Recorded Press Conference in Boston, Mass. at the Park Plaza Hotel, Jan. 16, 1980.

Weissman, 1981, "The cloning of interferon and other mistakes," *Interferon 1981* 3:101–134.

Zoon et al., 1980, "Amino terminal sequence of the major component of human lymphoblastoid interferon," *Science* 207(4430):527–528.

Zoon et al., 1980, "Human lymphoblastoid interferon: purification, amino acid composition, and amino–terminal sequence," *Ann. N.Y. Acad. Sci.* 350:390–398.

Zoon et al., 1979, "Purification and partial characterization of human lymphoblast interferon," *Proc. Natl. Acad. Sci. U.S.A.* 76(11):5601–5605.

Anonymous, Research Disclosure, Jul. 1979.

\* cited by examiner

```
                                                                        40
                 -60              -40               -20               +1                  20                  —
                  —                —                 —                 —                  —
LeIF A    TGAGCCTAAACCTTAGGCTCACCCATTTCAACCAGTCTAGCAGCATCTGCAACATCTACAATGGCCTTGACCTTTGCTTTACTGGTGGCCCTCCTGGTGC
LeIF B                                             TACTAGCTCAGCAGCATCCGCAACATCTACAATGGCCTTGACTTTTTATTTAATGGTGGCCTAGTGGTGC
LeIF C                              CAAGGTTATCCATCTCAAGTAGCCTAGCAATATTTGCAACATCCCAATGGCCCTGTCCTTTCTTTCTTACTTATGGCCGTGCTGGTGC
LeIF D                              CAAGGTTCAGAGTCACCCATCTCAGCAAGCCCAGAAGTATCTGCAATATCTACGATGGCCTCGCCCTTTGCTTTACTGATGGTCCTGGTGGTGC
LeIF E
LeIF F                                                       ACATCCCAATGGCCCTGTCCTTTTCTTTCTTTACTGATGGCCGTGCTGGTGC
LeIF G
LeIF H                          CCAAGGTTCAGTGTTACCCCTCATCAACCAGCAGCATCTTCGGGATTCCCAATGGCATTGCCCTTTGCTTTAATGATGGCCCTGGTGGTGC 60                  80                 100                 120                140
                  —                   —                  —                   —                  —
LeIF A    TCAGCTGCAAGTCAAGCTGCTCTGTGGGCTGTCTGCCTCAAACCCACAGCCTGGGTAGCAGGAGACCTTGATGCTCCTGGCACAGATGAGGAAAAT
LeIF B    TCAGCTGCAAGTCATTCAGCTCTCTGGGCTGTGTGCCTCTGCCTCAGATCCACAGACTCCTGGGTAACAGGAGAGGGCCTTGATACTCCTGGCACACAAATGCGAAGAAT
LeIF C    TCAGCTACAAATCCATCTCTGTTCTGGGCTGTGTGCCTCTGCCTCAGACCCACAGACCCCTGGGTAATAGGAGGAGGGCCTTGATACTCCTGGGACAAATGGGAAGAAT
LeIF D    TCAGCTGCAAGTCAAGCTGCTCTCTGGGCTGTGTGCCTCTGCCTCAGACCCACAGGCCCCACAGCCTGGGTAACAGGAGGAGGGCCTTGATGCTCCTCATACTCCTGACACAATGAGCAGAAT
LeIF E                         CTGCCTCTGGGCTGTGTGCCTCTGCCTCAGACCCACAGGCCCCACAGGCGTGGGTAACAGGAGGAGGGCCCTTCATACTCCTGACACAATGAGGAGAAT
LeIF F    TCAGCTACAAATCCATCTCTGTTCTGGGCTGTGTGCCTCTGCCTCAGACCCACAGGCCCCACAGCCTGGGTAATAGGAGGAGGGCCTTGATACTCCTGGCACAAATGGGAAGAAT
LeIF G                                 CTGCCTCTGGGCTGTGTGCCTCTGCCTCAGACCCACAGCCTGGGTAATAGGAGGAGGGCCTTGATAGGAGGGCCTTGATACTCCTGGCACAAATGAGGAGAAT
LeIF H    TCAGCTGCAAGTCAAGCTGCTCTCTGGGCTGTAATCTGTCTCAAACCCACAGCCTGAATAACAGGAGGACTTTGATGCTCATGGCACAAATGAGGAGAAT
```

FIG.3A

```
            160              180              200              220              240
             |                |                |                |                |
LeIF A  CTCTCTTTCTCCTGCTTGAAGGACAGACATGACTTTGGATTTCCC CAGGAGGAGTTT    GGCAACCAGTTCCAAAAGGCTGAAACCATCCTGTCCT
LeIF B  CTCTCCTTTCTCCTGCCTGAAGGACAGACATGACTTTGAATTCCCC CAGGAGGAGTTTGATGATAAACAGTTCCAGAAGGCTCAAGCCATCTCTGTCCT
LeIF C  CTCTCCTTTCTCCTGCCTGAAGGACAGACATGACTTTCCGAATCCCC CAGGAGGAGTTTGATGGCAACCAGTTCCAGAAGGCTCAAGCCATCTCTGTCCT
LeIF D  CTCTCCTTCCTGTCTGATGGACAGACATGACTTTGGATTTCCC    CAGGAGGAGTTTGATGGCAACCAGTTCCAGAAGGCTCCAGCCATCTCTGTCCT
LeIF E  CTCTCCTTTTCTTCTGAAGGACAGACATGACTTTGATTTCCATCATCAGGTGTTTCATGGCAACCACTTCCAGAAGGTTCAAGCTATCTTCCTTT
LeIF F  CTCTCCTTTCTCCTGCCTGAAGGACAGACATGACTTTGGATTCCC  CAAGAGGAGTTTGATGGCAACCAGTTCCAGAAGGCTCAAGCCATCTCTGTCCT
LeIF G                            CATGACTTTGGATTTCCT CAGGAGGAGTTTGATGGCAACCAGTTGATGGCAACCAGTTCCAGAAGGCTCAAGCCATCTCTGTCCT
LeIF H  CTCTCCTTTCTCCTGCCTGAAGGACAGACATGACTTTGAATTTCCC CAGGAGGAAATTTGATGGCAACCAGTTCCAGAAAGCTCAAGCCATCTCTGTCCT 260              280              300              320              340
              |                |                |                |                |
LeIF A  CCATGAGAGATGATCCAGCAGATCTTCAATCTCTTCAGCACAAAGGACTCATCTGCTGCTTGGGATGAGACCCTCTGCTGCTTAGACAAATTCTACACTGAACTCTAC
LeIF B  CCATGAGAGATGATCCAGCAGATCTTCAACCTCTTCAGCACAAAGGACTCATCTGCTGCTTGGGATGAGACCCTTCTAGATCTACATGAATTCACTGAACTTGAC
LeIF C  CCATGAGAGATGATCCAGCAGATCTTCAACCTCTTCAGCACAAAGGACTCATCTGCTGCTTGGGATGAGAGACCCTTCTAGATGAATTCTACATGAATTCACTGAACTTGAC
LeIF D  CCATGAGCTGATCCAGCAGATCTTCAACCTCTTTACCACAAAGGACTCATCTGCTGCTTGGGATGAGAGAGAGCCTCCTAGAGAACAAATTCCACTGAACTCTAC
LeIF E  CCATGAGAGATGATCCAGCAGATCATCAAAAGATTCATCTGCTGCTTGATACTTGGGATGAGAGAACAGAGACCCTCCTAGACAAATCCTACACTGAACTCTAC
LeIF F  CCATGAGAGATGATCCAGCAGATCTTCAGCACAAAGGACTCATCTGCTGCTTGGGATGAGAGACAGAGCCTCTTTTAGACAAATTTTCCACTGAACTCTAC
LeIF G  CCATGAGAGATGATCCAGCAGATCTTCAGCACAAAGGACTCATCTGCTGCTTGGGATGAGAGAGACACTTCTAGACAAATTCTACACTGAACTCTAC
LeIF H  CCATGAGAGATGAGCAGCAGAGACCTTCAGCACAAAGAACTCATCTGCTGCTTGGGATGAGAGAGACCCTCCTAGAAAAAATTCTACATTGAACTTTTC
```

```
                760                 780                 800                 820                 840
                 |                   |                   |                   |                   |
LeIF A GTCCCCTTACAGAGGACCATGCTGACTGATCCATTATCTATTATTAAAATATTTTAACTATTTATAAAACAACTATTTATTTTGTTCAT
LeIF B GCACTAGTCCCTTACAGATGACCATGCTGATGGATCTGATCATTCATCTATTCATTTTAGTTAACTACTATAGGGACTTAAATTAGTTTTGTT
LeIF C TCCTTTACAGATGACCATTCTGATGTCTCTGTTCATCTTTTGTTTAAATATTTAATTAATATTTATGTAATATCATGAGTCGCTTTACAT
LeIF D TGTTCATATAACGTCATGTGCACCTTTACACTGTGGTAGTGTAATAAAACATGTCCTTATATTACTC-poly(A)
LeIF E CTAGTTCCTTACGGATGATCATGCTGATGGATCTGTTTATCTATTGTCTAAATAATTATTAACTATTTATAAATATTTAAAATCTCTTTTCATGTATC
LeIF F CTAGTCCCTTACAGATGACCATGCTGATAGATCTATTGAAATATTTATTATTAGATTAAATTATTTTGTCCATGTAATATT
LeIF G AAATCTTTACAGATGATCATGCCAATCTATCTATCTATTATCTCATTATTCTAATCTATTTAAATATTTATTATTATAAGAT
LeIF H CTTTACAGATGACCATTCTGATGTCTCCTTTCATCTATTTATTTAACTATTTATTAAAATATTTAAAATATTTATTATGTAATATCA 860                 880                 900                 920                 940
                 |                   |                   |                   |                   |
LeIF A ATTACGTCATGTGCACCTTTGCACAGTGGTTAATAAAATATGTCTTTGTATTTGGT-poly(A)
LeIF B CATATATATATGTAACATATGTGAATTGTGTAACAAAAACATGTTCTATATTATTATTTGCCATGTTATTAAATTTTACTATGAAAAA
LeIF C TGTGGTTAATGTAACAATATATGTTCTTCATATTAATTTCCTTTTTCATTAAATTTTACTATAC-poly(A)
LeIF E ATGTATTTTACTTTGTGGTAATATAACACATGTTCTTTAGTCAATATGTTCTTTTTCATTAAATTTTACTATTAAAACTTCTAT
LeIF F ATGTGTACTTTACATTGTGTTATATCAAATATGTTAATCTATTATTATTTTCTTTATTATTTCTTTTATTAATAAATATGTCTTTATGTTTGTC-poly(A)
LeIF G TTAAATTATTTAAACTATTGTTCAGGTAACAAATATTAATCCACCTTACTTGTGGCTAATATATTAATTCCTTTTCATTAAATTTTACTAT-poly(A)
LeIF H TGAGTACCTTTACATTGTGGTTAATGTAACAAATATGTTCTTCATATTTAGCCAATATATTAATTCCTTTTCATTAAATTTTACTAT-poly(A)

960                 980                1000
                 |                   |                   |
LeIF B AATTCTTTATTCTTTAAAATTGAACTCCAACCCATGAATTGTGCAAACTGATTAAGAATGGATGGT-poly(A)
LeIF F ATTATTTGGTTATTCTTTAATAAGAAATTCCAAGCCC-poly(A)
```

FIG. 3E

```
           S1           S10       S20 S23                  30              40
           |            |          |  |                     |               |
LeIF A     MALTFALLVALLVLSCKSSCCSVGCDLPQTHSLGSRRTLMLLAQMRKISLFSCLKDRHDFGFPQ
LeIF B     MALTFYLMVALVVLSYKSFSSLGCDLPQTHSLGNRRALILLAQMRRISPFSCLKDRHDFEFPQ
LeIF C     MALSFSLLMAVLVLSYKSICSLGCDLPQTHSLGNRRALILLGQMGRISPFSCLKDRHDFRIPQ
LeIF D     MASPFALLMVLVVLSCKSSCCSLGCDLPETHSLDNRRTLMLLAQMSRISPSSCLMDRHDFGFPQ
LeIF E                   LPLGCDLPQAHSVGNRRAFILLTQMRRISPFSYLKDRHDFDFPH
LeIF F     MALSFSLLMAVLVLSYKSICSLGCDLPQTHSLGNRRALILLAQMGRISPFSCLKDRHDFGFPQ
LeIF G                                                       HDFGFPQ
LeIF H     MALPFSLMMALVVLSCKSSCCSLGCNLSQTHSLNNRRTLMLMAQMRRISPFSCLKDRHDFEFPQ

All        MA   F  L    VLS KS   S GC  L  THSL  RR L  L   QM    IS   SCL DRHDF   PQ 50              60              70              80              90             100
                        |               |               |               |               |               |
LeIF A     EEF-GNQFQKAETIPVLHEMIQQIFNLFSTKDSSAAWDETLLDKFYTELYQQLNDLEACVIQG
LeIF B     EEFDDKQFQKAQAISVLHEMIQQTFNLFSTKDSSAALDETLLDEFYIELDQQLNDLEVLCDQE
LeIF C     EEFDGNQFQKAQAISVLHEMIQQTFNLFSTEDSSAAWEQSLLEKFSTELYQQLNDLEACVIQE
LeIF D     EEFDGNQFQKAPAISVLHELIQQIFNLFTTKDSSAAMDEDLLDKFCTELYQQLNDLEACVMQE
LeIF E     QVFHGNHFQKVQAIFLFHEMMQQIFNLFSTKDSSDTWDETLLDKSYTELYQQLNDLEACVM*K
LeIF F     EEFDGNQFQKAQAISVLHEMIQQTFNLFSTKDSSATWEQSLLEKFSTELNQQLNDMEACVIQE
LeIF G     EEFDGNQFQKAQAISVLHEMIQQTFNLFSTKDSSATWDETLLDKFYTELYQQLNDLEACMMQE
LeIF H     EEFDGNQFQKAQAISVLHEMMQQTFNLFSTKNSSAAWDETLLEKFYIELFQQMNDLEACVIQE

All        EEFD  QFQKA  I VLHE  QQ FNLF T  SSA       LL  F   EL QQ  ND E    Q
```

FIG.4A

```
          110       120       130       140       150       160    166
           |         |         |         |         |         |      |
LeIF A    VGVTETPLMKEDSILAVRKYFQRITLYLKEKKYSPCAWEVVRAEIMRSFSLSTNLQESLRSKE
LeIF B    VGVIESPLMYEDSILAVRKYFQRITLYLTEKKYSSCAWEVVRAEIMRSFSLSINLQKRLKSKE
LeIF C    VGVEETPLMNEDSILAVRKYFQRITLYLIERKYSPCAWEVVRAEIMRSLSFSTNLQKRLRRKD
LeIF D    ERVGETPLMNVDSILAVKKYFRRITLYLTEKKYSPCAWEVVRAEIMRSLSLSTNLQERLRRKE
LeIF E    VGVEETPLRNVDSILAVRKYFQRITLYLTKKKYSPCAWEVVRAEIMRSFSL*TNLQERLRRKE
LeIF F    VGVEETPLMNVDSILAVRKYFQRITLYLTEKKYSPCSWEAVRAEIMRSFSLSKIFQERLRRKE
LeIF G    VGVEDTPLMNVDSILTVRKYFQRITLYLTEKKYSPCAWEVVRAEIMRSFSLSANLQERLRRKE
LeIF H    VGVEETPLMNEDSILAVRKYFQRITLYLMEKKYSPCAWEVVRAEIMRSFSFSTNLQKRLRRKD

All        V   PLM  DSIL V KYF RITLYL E KYS CAWEVVRAEIMRS  S S   Q  L   K
```

FIG.4B

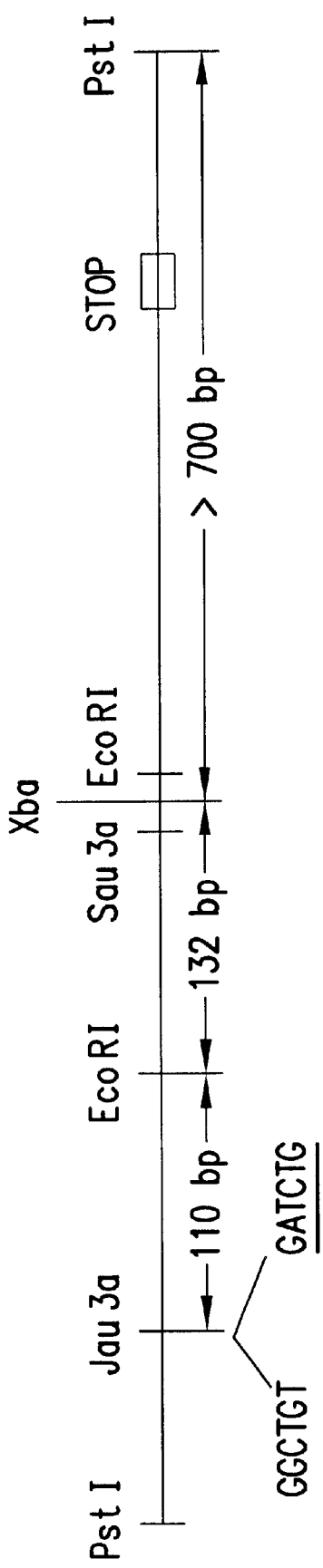
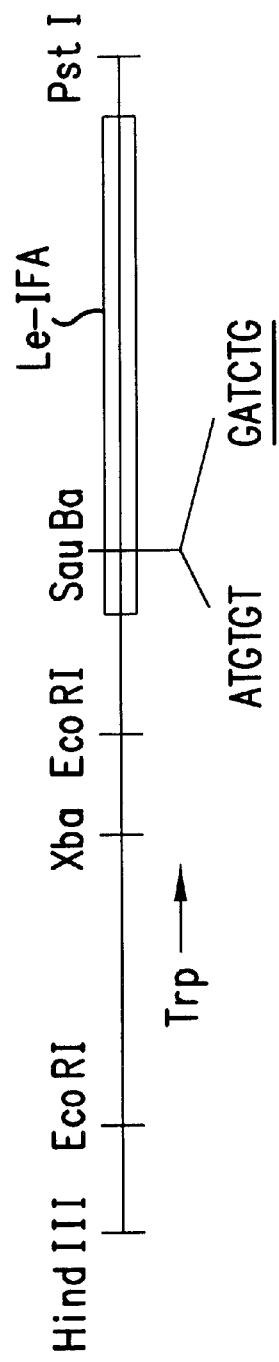
FIG.7a
FIG.7b

```
A         GTATGTTCCTA
H         GTATGTTCCCTA
I         GTATGTTCCTTA
J         GTATGTTCACTA
C         GTATGTTCACTA

A    TTTAAGGC-TAGGCACAAAGCAAGGTCTTCAGAGAACCTGGAGCCTAAGGTTTAGGCTCACCCATT-TCAACCAGTCTAGCAGCATCTGCAACATCTACA
H    TTTAAGGC-TAGGCACAAAGCAAGGTCTTCAGAGAACCTGGAGCCTAAGGTTTAGGCTCACCCATT-TCAACCAGTCTAGCAGCATCTGCAACATCTACA
I    TTTAAGACCTATGCACAGAGCAGCAAGGTCTTCAGAAAACCTAGCACCCAAGGTTCAGTGTTACCCCTCATCAACCAGCCCAGCAGCATCTTCAGGTTCCA
J    TTTAAGGCCTATGCACAGAGCAGCAAGGTCAAAGTCTTCAGAAAACCTAGAGGGCCAAAGTTCAAGGTTACCCATC-TCAAGTAGCTAGCAACATTGCAACATCCA-
C    TTTAAGACCTATGCACAGAGCAGCAAGGTCTCCAGAAAACCTAGAGGGCCACGGTTCAA-GTTACCCACC-TCAGGTAGCCTAGTGTGATATTTGCAAAATCCCA-

+1                                                                                                100
A    ATGGCCTTGACCTTTGCTTTACTGGTGGCCCTCCTCGTGCTGCTCAGCTGCAAGTCTGCTCTGTGGGCTGTGATCTGCCTCAAACCCACAGCCTGGGTA
H    ATGGCATTGCCCTTTGCTTTACTGGTGGCCCTCCTCGTGCTGGTGCTCAGCTGCAAGTCTGCTCAGCTGCAAGTCTGCTCTCTGGGCTGTGATCTGTCTCAAACCCACAGCCTGAATA
I    ATGGCCCTGTCCTTTGTCCTTTCTTTCTTTACTGATGGCCGTGTCGGTGCTGGTGCTCAGCTGCTACAAATCCATCGTTCTCTAGGCTGTGATCTGCCTGATCTGCCTCAGCCTGGGTA
J    ATGGCCCGGTTCCTTGTCCTTTCTTTTCTTTCTTTACTGATGGTGCTGGTGCTCAGCTGCTACAAATCCATCATCTGTGCTGCTGCTGGGCTGTCTCTGGGCTGCTGCCTCAGACCCTGCGTA
C    ATGGCCCTGTCCTTTGTCCTTTCTTTTCTTTACTTATGCCGTGTGCTGGTGCTGGTGCTCAGCTGCTACAAATCCATCGATCTCTGGGCTGTGCTGATCTGCCTGATCTCTGGGCTGTGATCTCTGGGCTGCCTGCCTCAGACCCACCCTGCGTA

200
A    GCAGGAGGACCTTGATGCTCCTGGCACAGATGAGGAGAATCTCTCTTTCTCCTGCTTGAAGGACAGACATGACTTGGATTTCCCCAGGAGGAGTTT--
H    ACAGGAGGACTTTGATGCTCATGGCACAAATGAGGAGAATCTCTCCTTTCTCCTGCCTGAAGGACAGACATGACTTGAATTTCCCCAGGAGGAGTTTGA
I    ATAGGAGGGCCTTGATACTCCTGGCACAAATGGGAAGAATCTCTCCTTTCTCCTTTCTCCTGCCTGAAGGACAGACCTGACTTTGGACTTCCCCAGGAGGAGTTTGA
J    ATAGGAGGGCCTTGATACTCCTGGCACAAATGGGAAGAATCTCTCCTTTCTCCTTTCTCCTGCCTGAAGGACAGACATGAATTCAGATTCCCAGAGGAGTTTGA
C    ATAGGAGGGCCTTGATACTCCTGGGACAAATGGGAAGAATCTCTCTTTCTCCTGCCTGAAGGACAGACATGATTTCCGAATCCCCAGGAGGAGTTTGA
```

FIG.8A

```
A  -GGCAACCAGTTCCAAAAGGCTGAAACCATCCCTGTCCTCCATGAGATGATCCAGCAGATCTTCAATCTCTTCAGCACACAAAGGACTCATCTGCTGCTTGG
H  TGGCAACCAGTTCCAGAAAGCTCAGAAGACTCAAGCCATCTCTGTCCTCCATGAGATGATGATCCAGCAGAGACCTTCAATCTCTTCAGCACACAAAGAACTCATCTGCTGCTTGG
I  TGGCAACCAGTTCCAGAAGACTCAAGCCATCTCTGTCCTCCATGAGATGATGATCCAGCAGAGACCTTCAATCTCTTCAGCACACAGAGGACTCATCTGCTGCTTGG
J  TGGCCACCAGTTCCAGAAGACTCAAGCCATCTCTGTCCTCCATGAGATGATCCAGCAGAGACCTTCAATCTCTTCAGCACACAGAGGACTCATCTGCTGCTTGG
C  TGGCAACCAGTTCCAGAAGGCTCAAGCCATCTCTGTCCTCCATGAGATGATCCAGCAGACCTTCAATCTCTTCAGCACACAGAGGACTCATCTGCTGCTTGG

400

A  GATGAGACCCTCCTAGACAAATTCTACACTGAACTCTACCAGCAGCTGAATGACCTGGAAGCCTGTGTGATACAGGGGGTGGGGGTGACAGAGACTCCCC
H  GATGAGACCCTCCTAGAGAAAATTCTACATTGAACTTTCCAGCAAATGAATGACCTGGAAGCCTGTGTGATACAGGAGAGTGGAAGAGGTTGGGGTGGAAGAGACTCCCC
I  GAACAGAGCCTCCTAGAGAAAATTTTCCACTGAACTTTCCACCAGCAACTGAATAACCTGGAAGCCTGTGTGATACAGGAGAGTGGATGGAAGAGGTTGGGATGGAAGAGACTCCCC
J  GAACAGAGCCTCCTAGAGAAAATTTTCCACTGAACTTTCCACCAGCAACTGAATGACCTGGAAGCCTGTGTGATACAGGAGCATGTGTGGGGTGGAAGAGGTTGGGGTGGAAGAGACTCCCC
C  GAACAGAGCCTCCTACAAAATTTTCCACTGAAATTTACCAGCAGCTGAATGACCTGGAAGCCTGTGTGATACAGGAGCATGTGAGCATGTGGAGCATGTGGAGAGGTTGGGGTGGAAGAGACTCCCC

500

A  TGATGAAGGAGGACTCCATTCTGGCTGTGAGGAAATACTTCCAAAGAATCACTCTCTATCTGAAAGAGAAGAAGAAATACAGCCCTTGTGCCTGGGAGGTTGT
H  TGATGAATGAGGAGGACTCCATCCTGGCTGTGAGGAAATACTTCCAAAGAATCACTCTCTTTATCTGATGAGAGAAGAAGAAATACAGCCCTTGTGCCTGGGGAGGTTGT
I  TGATGAATGAGGAGGACTCCATCCTGGCTGTGAGGAAATACTTCCAAAGAATCACTCTCTTTATCTAACAGAAGAAGAAATACAGCCCTTGTGCCTGGGGAGGTTGT
J  TGATGAATGAGGACTTCATCCTGGCTGTGAGGAAATACTTCCAAAGAATCACTCTCTTTATCTTTATCTAATGGAGAAGAAATACAGCCCTTGTGCCTGGGGAGGTTGT
C  TGATGAATGAGGACTCCATCCTGGCTGTGAGGAAATACTTCCAAAGAATCACTCTCTTTATCTTTATCTAATAGAGAGGAAATACAGCCCTTGTGCCTGGGGAGGTTGT
```

MICROBIAL PRODUCTION OF MATURE HUMAN LEUKOCYTE INTERFERONS

CROSS-REFERENCE TO RELATED APPLICATION

This is a continuation-in-part of our applications of same title: Ser. No. 06/205,578, filed Nov. 10, 1980 now abandoned; Ser. No. 06/184,909, filed Sep. 8, 1980; now abandoned and Ser. No. 06/164,986, filed Jul. 1, 1980 now abandoned.

FIELD OF THE INVENTION

This invention relates to the microbial production, via recombinant DNA technology, of human leukocyte interferons for use in thie treatment of viral and neoplastic diseases, and to the means and end products of such production.

BACKGROUND OF THE INVENTION

The publications and other materials referred to herein to illuminate the background of the invention and, in particular cases, to provide additional detail respecting its practice are incorporated herein by reference and, for convenience, are numerically referenced in the following text and respectively grouped in the appended bibliography.

Leukocyte Interferon

Human leukocyte interferon was first discovered and prepared in the form of very crude precipitates by Isaacs and Lindenmann (3). Efforts to purify and characterize the material have been ongoing since that time, and have led to the preparation of relatively homogeneous leukocyte interferons derived from normal or leukemic (chronic myelogenous leukemia or "CML") donors' leukocytes (4). These interferons are a family of proteins characterized by a potent ability to confer a virus-resistant state in their target cells (1,2). In addition, interferon can act to inhibit cell proliferation and modulate immune response. These properties have prompted the clinical use of leukocyte interferon as a therapeutic agent for the treatment of viral infections and malignancies.

Leukocyte interferons have been purified to essential homogeneity (7,8), and reported molecular weights range from about 17,500 to about 21,000. The specific activity of these preparations is remarkably high, $2 \times 10^8$ to $1 \times 10^9$ units/mg protein, but yields from cell culture methods have been discouragingly low. Nevertheless, advances in protein sequencing techniques have, in our hands, permitted the determination of partial amino acid sequences (4). Elucidation of the glycosylation of various leukocyte interferons is not at present complete, but it is now clear (by virtue of the work reported infra) that differences in glycosylation among family members does not alone account for the spectrum of molecular weights observed. Instead, the leukocyte interferons differ markedly in amino acid composition and sequence, and amino acid homology is, in some cases, less than 80 percent.

While isolation from donor leukocytes has provided sufficient material for partial characterization and limited clinical studies with homogeneous leukocyte interferon, it is a totally inadequate source for the amounts of interferon needed for large scale clinical trials and for broad scale prophylactic and/or therapeutic use thereafter. Indeed, presently clinical investigations employing human leukocyte-derived interferons in antitumor and antiviral testing have principally been confined to crude (<1 percent pure) preparations of the material, and long lead times for the manufacture of sufficient quantities, even at unrealistic price levels, have critically delayed investigation on an expanded front.

Recombinant DNA Technology

With the advent of recombinant DNA technology, the controlled microbial production of an enormous variety of useful polypeptides has become possible. Already in hand are bacteria modified by this technology to permit the production of such polypeptide products such as somatostatin (5), the (component) A and B chains of human insulin (9) and human growth hormone (18). More recently, recombinant DNA techniques have been used to occasion the bacterial production of proinsulin and thymosin alpha 1, an immune potentiating substance produced by the thymus.

Other workers have reported on the obtention of DNA coding for human leukocyte interferon and to resultant proteins having leukocyte interferon activity—cf. Nagata et al., *Nature* 284, 316 (1980); Mantei et al., *Gene* 10, 1 (1980). See also Taniguchi et al., *Nature* 285, 547 (1980).

The workhorse of recombinant DNA technology is the plasmid, a non-chromosomal loop of double-stranded DNA found in bacteria and other microbes, oftentimes in multiple copies per cell. Included in the information encoded in the plasmid DNA is that required to reproduce the plasmid in daughter cells (i.e., a "replicon") and ordinarily, one or more selection characteristics such as, in the case of bacteria, resistance to antibiotics which permit clones of the host cell containing the plasmid of interest to be recognized and preferentially grown in selective media. The utility of plasmids lies in the fact that they can be specifically cleaved by one or another restriction endonuclease or "restriction enzyme", each of which recognizes a different site on the plasmidic DNA. Thereafter heterologous genes or gene fragments may be inserted into the plasmid by endwise joining at the cleavage site or at reconstructed ends adjacent to the cleavage site. DNA recombination is performed outside the cell, but the resulting "recombinant" plasmid can be introduced into it by a process known as transformation and large quantities of the heterologous gene-containing recombinant plasmid obtained by growing the transformant. Moreover, where the gene is properly inserted with reference to portions of the plasmid which govern the transcription and translation of the encoded DNA message, the resulting expression vehicle can be used to actually produce the polypeptide sequence for which the inserted gene codes, a process referred to as expression.

Expression is initiated in a region known as the promoter which is recognized by and bound by RNA polymerase. In some cases, as in the tryptophan or "trp" promoter preferred in the practice of the present invention, promoter regions are overlapped by "operator" regions to form a combined promoter-operator. Operators are DNA sequences which are recognized by so-called repressor proteins which serve to regulate the frequency of transcription initiation at a particular promoter. The polymerase travels along the DNA, transcribing the information contained in the coding strand from its 5' to 3' end into messenger RNA which is in turn translated into a polypeptide having the amino acid sequence for which the DNA codes. Each amino acid is encoded by a nucleotide triplet or "codon" within what may for present purposes be referred to as the "structural gene", i.e. that part which encodes the amino acid sequence of the expressed product. After binding to the promoter, the RNA polymerase first transcribes nucleotides encoding a ribosome binding site, then a translation initiation or "start" signal (ordinarily ATG, which in the resulting messenger RNA becomes AUG), then the nucleotide codons within the structural gene itself. So-called stop codons are transcribed at the end of the structural gene whereafter the polymerase may form an additional sequence of messenger RNA which, because of the presence of the stop signal, will remain untranslated by the ribosomes. Ribosomes bind to the binding site provided on the messenger RNA, in bacteria ordinarily as the mRNA is being formed, and themselves produce the encoded polypeptide, beginning at the translation start signal and ending at the previously mentioned stop signal. The desired product is produced if the sequences encoding the ribosome binding site are positioned properly with respect to the AUG initiator codon and if all remaining codons follow the initiator codon in phase. The resulting product may be obtained by lysing the host cell and recovering the product by appropriate purification from other bacterial protein.

We perceived that application of recombinant DNA technology would be the most effective way of providing large quantities of leukocyte interferon which, despite the absence in material so produced of the glycosylation characteristic of human-derived material, could be employed clinically in the treatment of a wide range of viral and neoplastic diseases.

More particularly, we proposed and have since succeeded in producing mature human leukocyte interferon microbially, by constructing one or more genes therefor which could then be inserted in microbial expression vehicles and expressed under the control of microbial gene regulatory controls.

Our approach to obtaining a first leukocyte gene involved the following tasks:

1. Partial amino acid sequences would be obtained by characterization of leukocyte interferon purified to essential homogeneity, and construct sets of synthetic DNA probes constructed whose codons would, in the aggregate, represent all the possible combinations capable of encoding the partial amino acid sequences.

2. Bacterial colony banks would be prepared containing cDNA from induced messenger RNA. Other induced mRNA that had been radio-labelled would be hybridized to plasmid cDNA from this bank. Hybridizing mRNA would be eluted and tested for translation into interferon in oocyte assay. Plasmid DNA from colonies shown positive for interferon in this manner would be further tested for hybridization to probes made as described in (1) above.

3. Parallel to the approach in part (2) above, induced mRNA-derived cDNA in plasmids would be used to form an independent bank of transformant colonies. The probes of part (1) would be used to prime the synthesis of radio-labelled single stranded cDNA for use as hybridization probes. The synthetic probes would hybridize with induced mRNA as template and be extended by reverse transcription to form induced, radio-labelled cDNA. Clones from the colony bank that hybridized to radio-labelled cDNA obtained in this manner would be investigated further to confirm the presence of a full-length interferon encoding gene. Any partial length putative gene fragment obtained in parts (1) or (2) would itself be used as a probe for the full-length gene.

4. The full-length gene obtained above would be tailored, using synthetic DNA, to eliminate any leader sequence that might prevent microbial expression of the mature polypeptide and to permit appropriate positioning in an expression vehicle relative to start signals and the ribosome binding site of a microbial promoter. Expressed interferon would be purified to a point permitting confirmation of its character and determination of its activity notwithstanding the absence of glycosylation.

5. The interferon gene fragment prepared in the foregoing fashion could itself be used in probing, by hybridization, for other partially homologous leukocyte interferon species.

BRIEF SUMMARY OF INVENTION

We have discovered and, through recombinant DNA technology, enabled the microbial production in high yield of the family of homologous leukocyte interferons (sans glycosylation) as mature polypeptides, essentially unaccompanied by the corresponding presequence or any portion thereof. These may be directly expressed, recovered and purified to levels fitting them for use in the treatment of viral and malignant diseases of animals and man. Family members so far expressed have proven efficacious in in vitro testing and, in the first such demonstration of its kind, in in vivo testing as well, the latter involving the first mature leukocyte interferon to have been microbially produced. The invention comprises the interferons so produced and means of producing them.

Reference herein to the expression of a "mature leukocyte interferon," connotes the bacterial or other microbial production of an interferon molecule unaccompanied by associated glycosylation and the presequence that (as we have discovered) immediately attends mRNA translation of a human leukocyte interferon genome. Mature leukocyte interferon, according to the present invention, is immediately expressed from a translation start signal (ATG) just before the first amino acid codon of the natural product, in which event the mature polypeptide includes the methionine for which ATG codes without essentially altering its character, or the microbial host may process the translation product to delete the initial methionine. Mature leukocyte interferon could be expressed together with a conjugated protein other than the conventional leader, the conjugate being specifically cleavable in an intra- or extracellular environment. See British Patent Publication No. 2007676A. Finally, the mature interferon could be produced in conjunction with a microbial "signal" peptide which transports the conjugate to the cell wall, where the signal is processed away and the mature polypeptide secreted.

Particular leukocyte interferon proteins hereof have been defined by means of determined DNA gene and deductive amino acid sequencing—cf. FIGS. 3, 4, 8 and 9, for example. It will be understood that for these particular interferons, indeed all of the family of leukocyte interferon proteins embraced herein, natural allelic variations exist and occur from individual to individual. These variations may be demonstrated by (an) amino acid difference(s) in the overall sequence or by deletions, substitutions, insertions, inversions or additions of (an) amino acid(s) in said sequence. For each leukocyte interferon protein hereof, labelled LeIF A, LeIF B . . . LeIF J, etc., such allelic variations are included within the scope of the label or term defining such, and thus, this invention.

BRIEF DESCRIPTION OF THE DRAWINGS

FIGS. 3A–3E depict the nucleotide sequence (coding strand) of eight gene fragments isolated as candidates for use in the expression of leukocyte interferons, respectively designated "A" through "H". The ATG translational initiation codon and the termination triplet for each LeIF is underlined. The stop codons or termination triplets are followed by 3' untranslated regions. The included full length gene for Le-IF "A" is missing one codon found in the others depicted, as indicated in the third "A" line of FIG. 3B. 5' untranslated regions precede the leader sequences. As isolated, fragment "E" lacked the full presequence or leader, but included the entire gene for the putative mature Le-IF "E". Fragment G as isolated lacked the full coding sequence. The nucleotide sequence in the rows labeled "LeIF A" (SEQ ID NO:1) encodes a 188 amino acid translation product (SEQ ID NO:2). The nucleotide sequence in the rows labeled "LeIF B" (SEQ ID NO:3) encodes a 189 amino acid translation product (SEQ ID NO:4). The nucleotide sequence in the rows labeled "LeIF C"(SEQ ID NO:5) encodes a 189 amino acid translation product (SEQ ID NO:6). The nucleotide sequence in the rows labeled "LeIF D" (SEQ ID NO:7) encodes a 189 amino acid translation product (SEQ ID NO:8). The nucleotide sequence in the rows labeled "LeIF E"(SEQ ID NO:9) encodes fragments of a translation product: nucleotides 1–186 encode a 62 amino acid fragment (SEQ ID NO: 10), nucleotides 190–234 encode a 15 amino acid fragment (SEQ ID NO:62), nucleotides 250–273 encode an 8 amino acid fragment (SEQ ID NO:63), nucleotides 277–294 encode a 6 amino acid fragment (SEQ ID NO:64), nucleotides 298–420 encode a 41 amino acid fragment (SEQ ID NO:65), and nucleotides 424–534 encode a 37 amino acid fragment (SEQ ID NO:66). The nucleotide sequence in the rows labeled "LeIF F" (SEQ ID NO:11) encodes a 189 amino acid translation product (SEQ ID NO:12). The nucleotide sequence in the rows labeled "LeIF G" (SEQ ID NO: 13) encodes a partial amino acid translation product (SEQ ID NO:14). The nucleotide sequence in the rows labeled "LeIF H" (SEQ ID NO:15) encodes a 189 amino acid translation product (SEQ ID NO:16). Nucleotides 126–623 of SEQ ID NO:15 encode a 166 residue mature amino acid translation product (SEQ ID NO:56).

The nucleotide sequence in the rows labeled "LeIF A" (SEQ ID NO:1) encodes a 188 amino acid translation product (SEQ ID NO:2). The nucleotide sequence in the rows labeled "LeIF B" (SEQ ID NO:3) encodes a 189 amino acid translation product (SEQ ID NO:4). The nucleotide sequence in the rows labeled "LeIF C" (SEQ ID NO:5) encodes a 189 amino acid translation product (SEQ ID NO:6). The nucleotide sequence in the rows labeled "LeIF D" (SEQ ID NO:7) encodes a 189 amino acid translation product (SEQ ID NO:8). The nucleotide sequence in the rows labeled "LeIF E" (SEQ ID NO:9) encodes fragments of a translation product: nucleotides 1–186 encode a 62 amino acid fragment (SEQ ID NO:10), nucleotides 190–234 encode a 15 amino acid fragment (SEQ ID NO:62), nucleotides 250–273 encode an 8 amino acid fragment (SEQ ID NO:63), nucleotides 277–294 encode a 6 amino acid fragment (SEQ ID NO:64), nucleotides 298–420 encode a 41 amino acid fragment (SEQ ID NO:65), and nucleotides 424–534 encode a 37 amino acid fragment (SEQ ID NO:66). The nucleotide sequence in the rows labeled "LeIF F" (SEQ ID NO:11) encodes a 189 amino acid translation product (SEQ ID NO:12). The nucleotide sequence in the rows labeled "LeIF G" (SEQ ID NO:13) encodes a partial amino acid translation product (SEQ ID NO:14). The nucleotide sequence in the rows labeled "LeIF H" (SEQ ID NO:15) encodes a 189 amino acid translation product (SEQ ID NO:16). Nucleotides 126–623 of SEQ ID NO:15 encode a 166 residue mature amino acid translation product (SEQ ID NO:56).

Figure 3C:
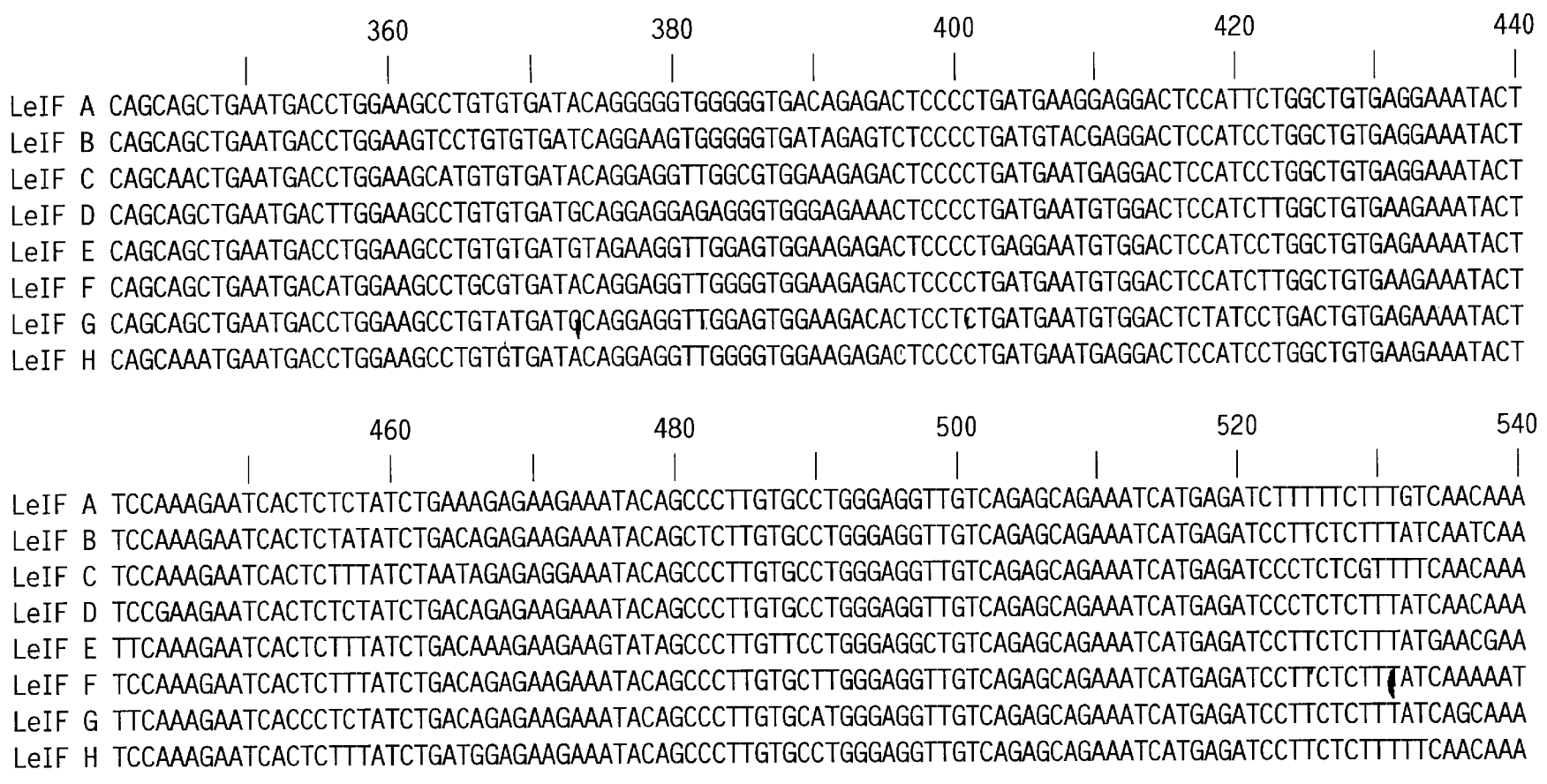
Figure 3D:
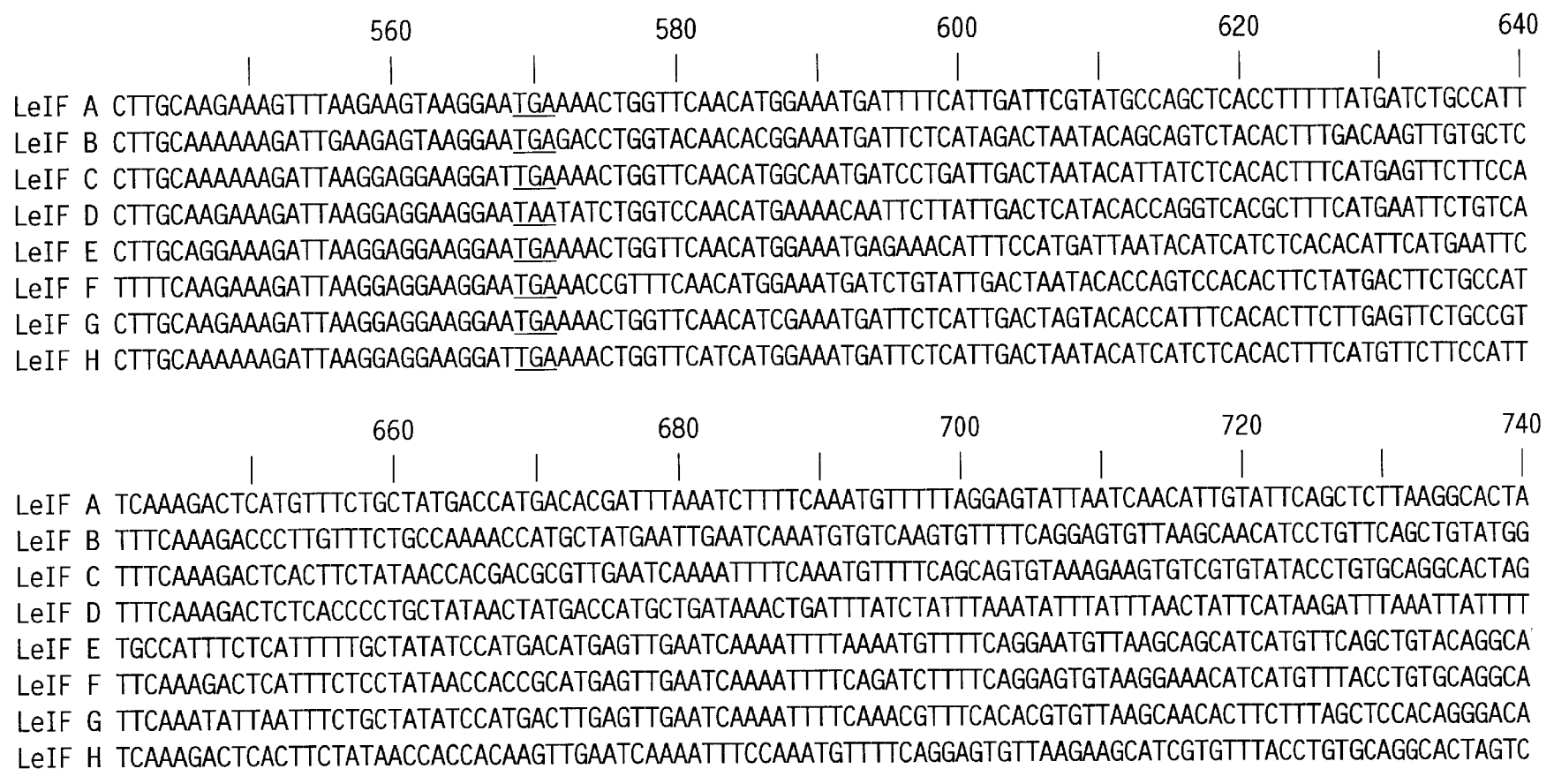

FIGS. 4A–4B are a comparison of eight LeIF protein sequences predicted from nucleotide sequences. The one letter abbreviations recommended by the IUPAC-IUB Commission on Biochemical Nomenclature are used: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; and Y, tyrosine. The numbers refer to amino acid position (S refers to signal peptide). The dash in the 165 amino acid LeIF A sequence at position 44 is introduced to align the LeIF A sequence with the 166 amino acid sequences of the other LeIFs. The LeIF E sequence was determined by ignoring the extra nucleotide (position 187 of FIG. 3B) in its coding region. The asterisks indicate in-phase termination codons. The amino acid sequence in the rows labeled "LeIF A" is a 188 residue LeIF A polypeptide (SEQ ID NO:17) with an intact signal peptide. The amino acid sequence labeled S1–S23 is the signal peptide, and the amino acid sequence labeled 1–166 is the mature LeIF A polypeptide (SEQ ID NO:45).

Figure 5:
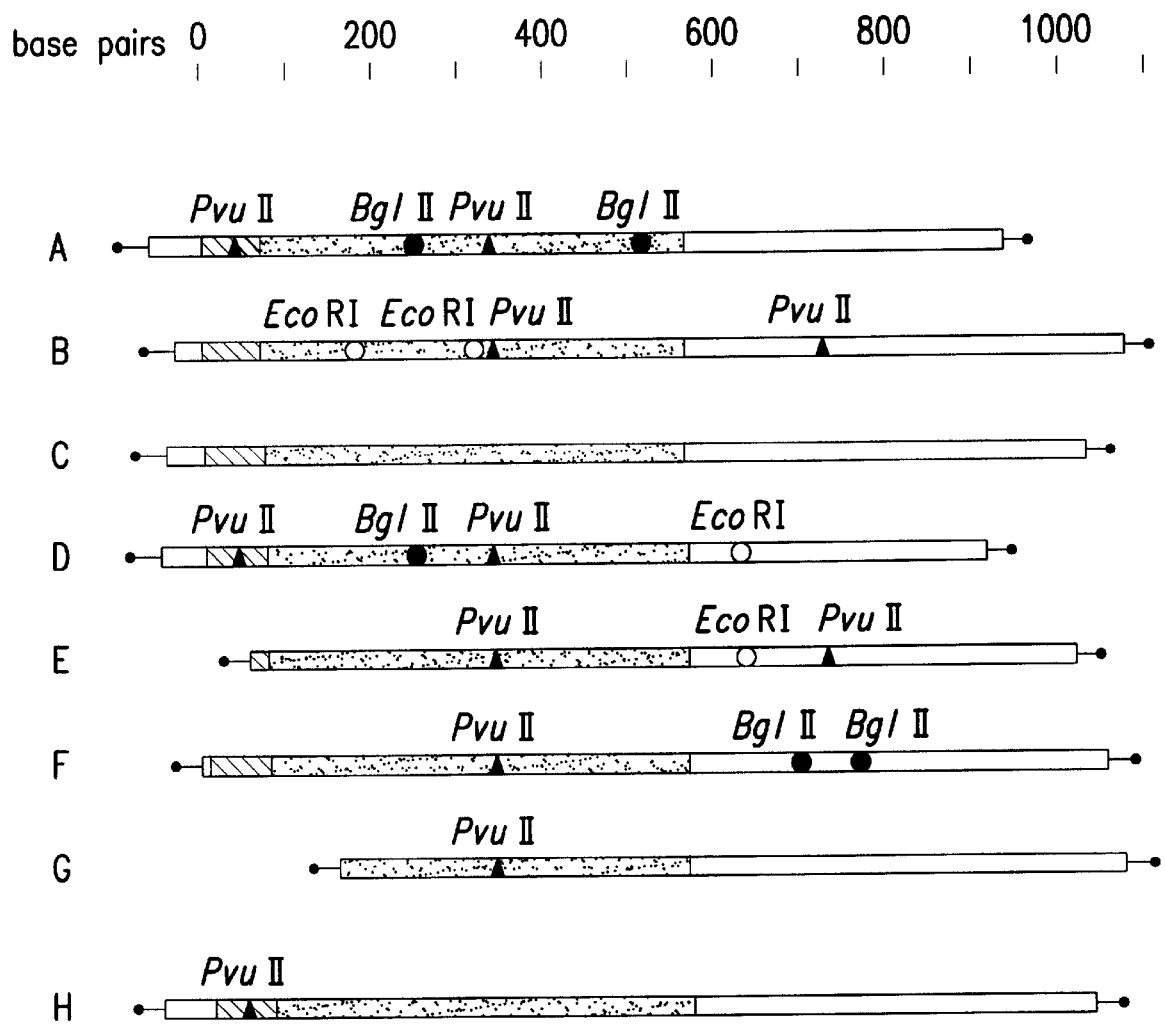

FIG. 5 depicts restriction endonuclease maps of the eight types of LeIF cloned cDNAs (A through H). The hybrid plasmids were constructed by the dC:dG tailing method Goeddel, D. V. et al, Nature 287, 411–416 (1980). Therefore, the cDNA inserts can be exised using Pst I. The lines at the end of each cDNA insert represent the flanking homopolymeric dC:dG tails. The positions of Pvu II, Eco RI and Bgl II restriction sites are indicated. Shaded regions of the figure represent the coding sequences of mature LeIFs; the cross-hatched regions indicate signal peptide coding sequences; and the open regions show 3' and 5' noncoding sequences.

Figure 6:
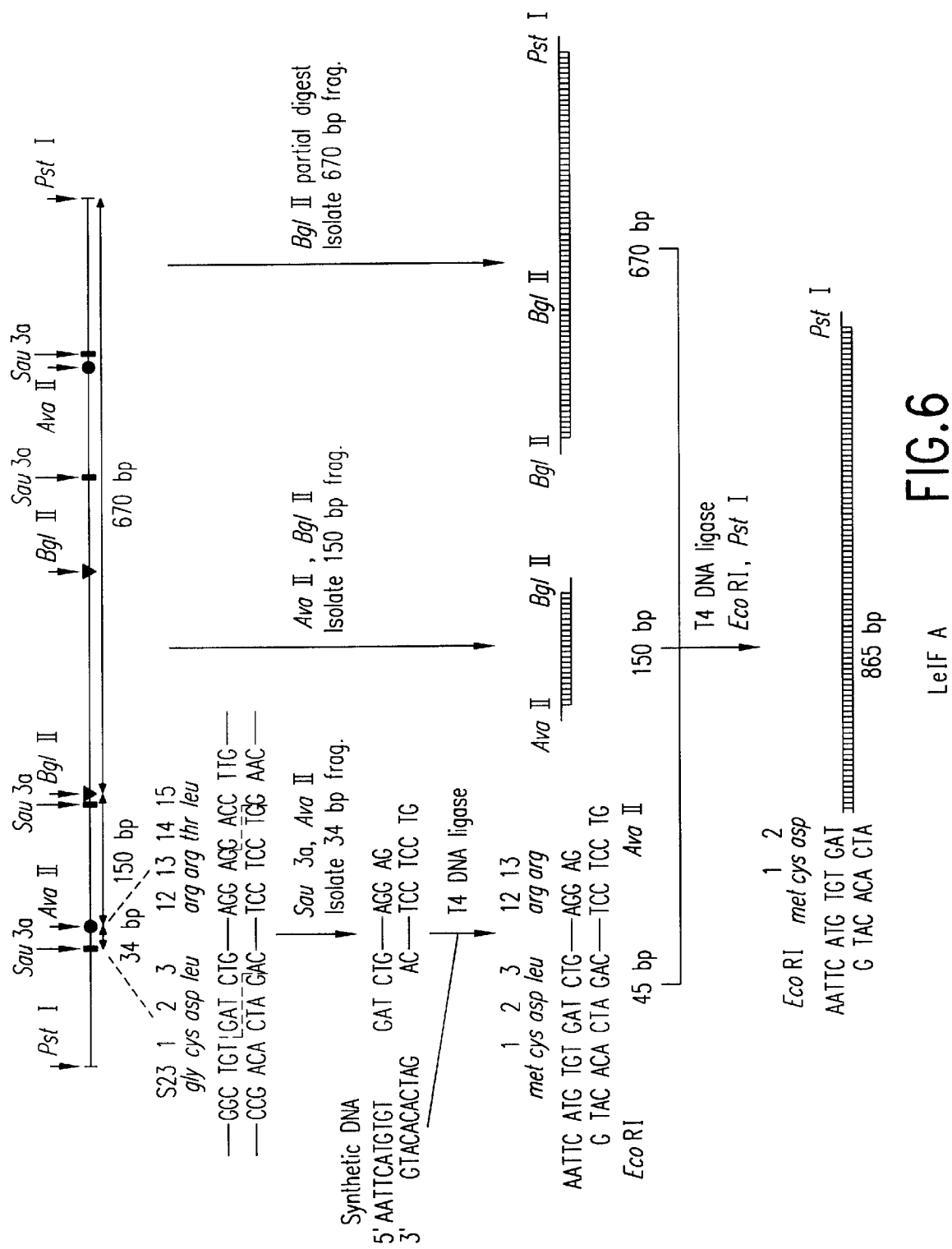

FIG. 6 schematically depicts the construction of a gene coding for the direct microbial synthesis of mature Le-IF A. Restriction sites and residues are as shown ("Pst I", etc.). The term "b.p." connotes "base pair."

FIGS. 7(a and b) (not to scale) schematically depicts a restriction map of two gene fragments employed in expressing the mature leukocyte interferon Le-IF B. The codon sequences indicated are the coding strand terminii resulting from digestion with the restriction enzyme Sau 3a in the two cases shown.

FIGS. 8A–8D provide the DNA sequences of the five LeIF proteins hereof, including types I and J. The nucleotide sequence (SEQ ID NO:25) in the rows labeled "A" encodes a 188 amino acid translation product (SEQ ID NO:26). The nucleotide sequence (SEQ ID NO:27) in the rows labeled "H" encodes a 189 amino acid translation product (SEQ ID NO:28). Nucleotides 180–677 of SEQ ID NO:27 encode a mature 166 amino acid translation product (SEQ ID NO:58). The nucleotide sequence (SEQ ID NO:29) in the rows labeled "I" encodes a 189 amino acid translation product (SEQ ID NO:30). Nucleotides 182–679 of SEQ ID NO:29 encode a mature 166 amino acid translation product (SEQ ID NO:59). The nucleotide sequence (SEQ ID NO:31) in the rows labeled "J" encodes a 189 amino acid translation product (SEQ ID NO:32). The nucleotide sequence (SEQ ID NO:33) in the rows labeled "C" encodes two amino acid translation products. Nucleotides 110–166 of SEQ ID NO:33 encode a 19 amino acid translation product (SEQ ID NO:69), and nucleotides 170–676 of SEQ ID NO:33 encode a 169 amino acid translation product (SEQ ID NO:34). Nucleotides 179–676 of SEQ ID NO:33 encode a mature 166 amino acid translation product (SEQ ID NO:57).

FIGS. 9A–9B provide the amino acid (see FIGS. 4A–4B above for the corresponding one letter abbreviations)

sequences of five LeIF proteins hereof. The asterisk indicates a termination codon and the hyphen, a deletion or gap in the sequence. The amino acid sequence in the rows labeled "A" is a 188 residue polypeptide (SEQ ID NO:35) with an intact signal peptide. The amino acid sequence labeled S1–S23 is the signal peptide, and the amino acid sequence labeled 1–166 is the mature polypeptide (SEQ ID NO:53).

Figure 10:

FIG. 10 schematically depicts filling in of 2 of the 4 nucleotides complementary to the 5' protruding end of the XbaI cleavage site.

Figure 11:
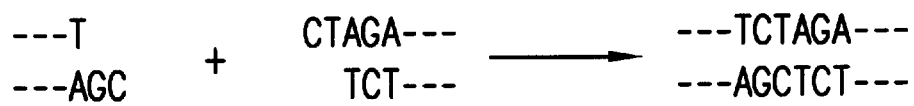

FIG. 11 schematically depicts ligation of the Taq I protruding end of the Eco RI-Taq I fragment to the XbaI remaining protruding end of the fragment from pHS32.

Figure 12:
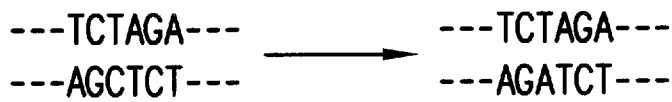

FIG. 12 schematically depicts regeneration of the BbaI site via E. coli catalyzed DNA repair and replication.

Figure 13:
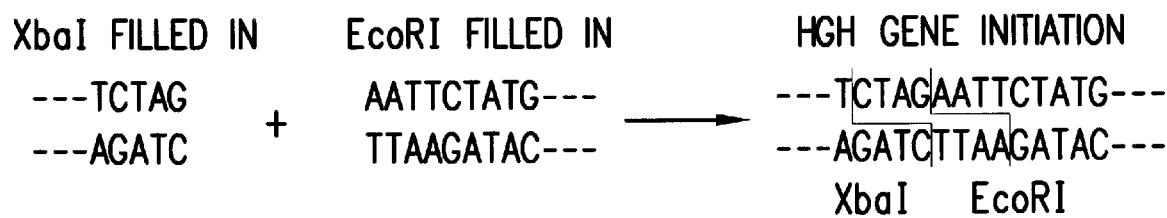

FIG. 13 schematically depicts blunt end ligation of an XbaI filled in fragment with an Eco RI filled in fragment to recreate both the XbaI and the Eco RI site.

The amino acid sequence in the rows labeled "H" is a 189 residue polypeptide (SEQ ID NO:36) with an intact signal peptide. The amino acid sequence labeled S1–S23 is the signal peptide, and the amino acid sequence labeled 1–166 is the mature polypeptide (SEQ ID NO:55).

The amino acid sequence in the rows labeled "I" is a 189 residue polypeptide (SEQ ID NO:37) with an intact signal peptide. The amino acid sequence labeled S1–S23 is the signal peptide, and the amino acid sequence labeled 1–166 is the mature polypeptide (SEQ ID NO:51).

The amino acid sequence in the rows labeled "J" is a 189 residue polypeptide with an intact signal peptide (SEQ ID NO:32). The amino acid sequence labeled S1–S23 is the signal peptide, and the amino acid sequence labeled 1–166 is the mature polypeptide (SEQ ID NO:52).

The amino acid sequences in the rows labeled "C" are two polypeptide fragments. The amino acid sequence labeled S1–S19 is a 19 residue polypeptide (SEQ ID NO:70), and the amino acid sequence labeled S21–166 is a 169 residue polypeptide (SEQ ID NO:38). The amino acid sequence labeled 1–166 of SEQ ID NO:38 is a mature polypeptide (SEQ ID NO:54).

DESCRIPTION OF THE PREFERRED EMBODIMENTS

A. Microorganisms Employed

The work described involved use of two microorganisms: E. coli x1776, as described in (11), and E. coli K-12 strain 294 (end A, thi⁻, hsr⁻, hsm$_k$⁺), as described in (12). Each has been deposited with the American Type Culture Collection, respectively ATCC accession nos. 31537 and 31446. All recombinant DNA work was performed in compliance with applicable guidelines of the National institutes of Health.

The invention, in its most preferred embodiments, is described with reference to E. coli, including not only strains E. coli x 1776 and E. coli K-12 strain 294, defined above, but also other known E. coli strains such as E. coli B, or other microbial strains many of which are deposited and (potentially) available from recognized microorganism depository institutions, such as the American Type Culture Collection (ATCC)—cf. the ATCC catalogue listing. See also German Offenlegungsschrift 2644432. These other microorganisms include, for example, Bacilli such as Bacillus subtilis and other enterobacteriaceae among which can be mentioned as examples Salmonella typhimurium and Serratia marcesans, utilizing plasmids that can replicate and express heterologous gene sequences therein. Yeast, such as Saccharomyces cerevisiae, may also be employed to advantage as host organism in the preparation of the interferon proteins hereof by expression of genes coding therefor under the control of a yeast promoter. (See the copending U.S. patent application of Hitzenan et al., filed Feb. 25, 1981 (Attorney Docket No. 100/43), assignee Genentech, Inc. et al., which is incorporated herein by reference.)

B. Source of Le-IF mRNA

Le-IF mRNA may be obtained from human leukocytes, ordinarily those of patients with chronic myelogenous leukemia, that have been induced to produce interferon with Sendai or NDV virus, as described in (4). A particularly preferred source, and that used in the work reported herein, is a cell line designated KG-1 derived from a patient with acute myelogenous leukemia. The cell line, described by Koeffler, H. P. and Golde, D. W., Science 200, 1153 (1978), reference (15), grows readily in a culture medium comprising RPMI 1640 plus 10 FCS (heat-inactivated), 25 mM Hepes buffer and 50 μg/ml of gentamicin, and is subcultured 1 to 3 split two times a week. Cells may be frozen from the foregoing growth medium plus 10 dimethyl sulfoxide. KG-1 has been deposited with the American Type Culture Collection, ATCC accession no. CRL 8031.

C. Messenger RNA Purification from KG-1 Cells

KG-1 cells were induced to produce interferon (and leukocyte interferon mRNA) with Sendai or NDV following the procedure described by Rubinstein et al., Proc. Natl. Acad. Sci. USA 76, 640 (1979) and Familetti et al., Methods in Enzymology, (1981) (in press) and (4). Cells were harvested 5 hours after induction and RNA prepared by the guanidine thiocyanate-guanidine hydrochloride procedure (14). RNA from uninduced cells was isolated in the same manner. Oligo (dT)-cellulose chromatography and sucrose gradient ultracentrifugation was used to obtain the 12 S sucrose gradient fraction of poly (A) RNA as described (16,21). This mRNA had an interferon titer of 8000–10,000 units per microgram in the Xenopus laevis oocyte assay (6).

D. Preparation of Colony Banks Containing Le-IF cDNA Sequences

5 μg of mRNA was used to prepare double stranded cDNA by standard procedures (17,18). The cDNA was size fractionated by electrophoresis on a 6 polyacrylamide gel and 230 ng of material ranging in size from 500 to 1500 base pairs were recovered by electroelution. A 100 ng portion of this cDNA was tailed with deoxyC residues (19), annealed with 470 ng of plasmid pBR322 (20) which had been tailed with deoxy G residues at the Pst I site, and used to transform E. coli X1776. Approximately 130 tetracycline resistant, ampicillin sensitive transformants were obtained per ng of cDNA.

In a second similar experiment, approximately 1000 tetracycline resistant, ampicillin sensitive E. coli 294 transformants were obtained per ng of cDNA. In this case size fractionated cDNA material ranging in size from 600 to 1300 b.p. was recovered by electroelution for deoxyC tailing.

E. Preparation of Synthetic Oligonucleotides

Figure 1:
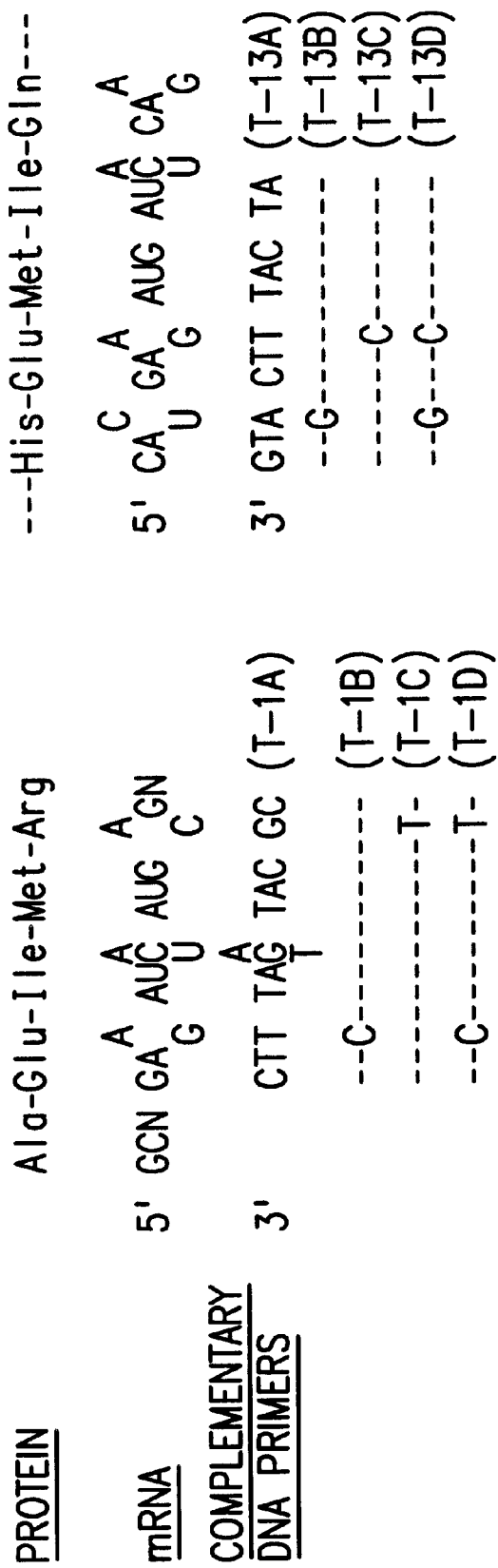
FIG. 1 depicts two series of synthetic deoxynucleotides designated T-1 and T-13 designed to prime cDNA synthesis from leukocyte interferon ("Le-IF") mRNA. Amino acid sequences are given for peptide 1 and a portion of peptide 13 derived from a tryptic digest of human Le-IF β(4). All potential mRNA sequences coding for these peptides are shown, as are the corresponding DNA sequences. Here and throughout, the letters A, T, C, G and U respectively connote the nucleotides containing the bases adenine, thymine, guanine, cytosine and uracil, and polynucleotides are depicted as reading from the 5' (left) in the 3' (right) direction and, where double stranded ("d.s.") DNA is depicted, vice-versa for the bottom or non-coding strand.

The amino acid sequences of several tryptic fragments of human leukocyte interferon were determined (4). This information. permitted the design of synthetic deoxyoligonucleotides potentially complementary to different regions of LeIF mRNA. The two tryptic peptides T1 and T13 were selected because they had amino acid sequences requiring the synthesis of only 12 and 4 undecamers, respectively, to acount for all possible coding sequences (FIG. 1.). Four sets of deoxyoligonucleotide probes were synthesized for each sequence, containing either three (T-1A, B, C, D) or one (T-13A, B, C, D) oligonucleotide each. The indicated complementary deoxyoligonucleotides 11 bases long were chemically synthesized by the phosphotriester method (24). Four individual probes were prepared in the T-13 series. The twelve T-1 probes were prepared in four pools of three probes as shown in FIG. 1.

F. Isolation of Partial Le-IF Gene Fragment Containing Plasmid No. 104

Transformants of E. coli x1776 were screened by the colony hybridization procedure (27) using $^{32}$P-labelled (32) induced mRNA as probe. Unlabelled mRNA from uninduced cells was mixed with the probe at a ratio of 200 to 1 to compete with uninduced mRNA present in the $^{32}$P-labelled preparation. Hybridization of labelled mRNA should occur preferentially to colonies containing induced sequences. Three classes of transformants were obtained. (1) 2–3 of the colonies hybridized to $^{32}$P-mRNA very strongly, (2) 10 hybridized significantly less than class 1, and (3) the remainder gave no detectable hybridization signal. This 3rd class was eliminated from further screening.

The positive colonies were examined for the presence of interferon-specific sequences by an assay which depends upon hybridization of interferon mRNA specifically to plasmid DNA. Initially, 60 strong positive colonies (class 1) were grown individually in 100 ml of M-9 broth (42) supplemented with tetracycline (20 µg/ml), diaminopimelic acid (100 µg/ml), thymidine (20 µg/ml), and d-biotin (1µg/ml). Ten cultures were pooled and plasmid DNA was isolated from the six pools as described earlier (34,35). Ten µg of each plasmid DNA pool were cleaved with HindIII, denatured and covalently bound to DBM paper (36). One µg of purified mRNA from induced cells was hybridized to each filter. Unhybridized mRNA was removed-by washing. The specifically hybridized mRNA was eluted and translated in Xenopus laevis oocytes. By this assay, all six pools were negative. Five pools of ten colonies each and one pool of nine colonies were made from 59 weakly positive colonies, (class 2) and plasmids were prepared from the pools and examined as above. Among the six pools tested, one (K10) hybridized to interferon mRNA at levels significantly above background levels each time it was tested. In order to identify the specific interferon cDNA clone plasmid DNAs were prepared from the 9 colonies of pool K10 and examined individually. Two of the nine plasmids ( No. 101 and No. 104) bound interferon mRNA well above background levels.

G. Preparation and Use of cDNA Probes Obtained by Synthetic Oligonucleotide Priming of Induced mRNA; Identification of Colonies pL 1–30

A rapid plasmid isolation procedure (22) was used to prepare 1 µg of plasmid DNA from each of 500 individual E. coli 294 transformants. Each DNA sample was denatured and applied to nitrocellulose filters in triplicate following a published procedure (23).

The four individual probes of the T-13 series and the twelve T-1 probes prepared in four pools of three primers each were used to prime the synthesis of radiolabelled single stranded cDNA for use as hybridization probes. The template mRNA was either the 12S RNA from Sendai-induced KG-1 cells (8000 units IF activity per µg) or total poly (A) mRNA from uninduced leukocytes (<10 units per µg). P-labelled cDNA was prepared from these primers using published reaction conditions (25). The 60 µl reactions were performed in 20 mM Tris-HCl (pH8.3), 20 mM KCl, 8 mM MgCl$_2$, 30 mM β-merceptoethanol. Reactions included one µg of each primer (i.e. 12 µg total for T-1 series, 4 µg total for T-13 series), 2 µg of "induced" 12S fraction mRNA (or 10 µg of uninduced poly (A) mRNA), 0.5 mM dATP, dGTP, dTTP, 200 µCi ($\alpha^{32}$P)dCTP (Amersham, 2–3,000 Ci/mmole), and 60 units reverse transcriptase (Bethesda Research Laboratories). Product was separated from unincorporated label by gel filtration on a 10 ml Sephadex G-50 column, treated with 0.3N NaOH for 30' at 70° C. to destroy RNA, and neutralized with HCl. Hybridizations were performed as described (23).

The three sets of nitrocellulose filters containing the 500 plasmid samples were hybridized with a) induced cDNA primed with the T-1 set of primers, b) T-13 primed induced cDNA, and c) uninduced cDNA prepared by using both sets of primers. Clones were considered positive if they hybridized more strongly to one or both of the induced cDNA probes than to the total uninduced probe. Thirty "positive" clones (pL1–pL30) were selected from the 500 for further analysis.

H. Selection of Additional "Positive" Colonies pl31–39 Using a Restriction Fragment of Plasmid 104

A unique 260 b.p. BglII restriction fragment isolated from the plasmid 104 clone was labelled by a published. procedure (26) with $^{32}$P and used as probe to independently screen 400 E. coli 294 transformants by an in situ colony screening procedure. (27). Nine colonies (pL31–pL39) were identified which hybridized to different extents with this probe. In addition, the labelled 260 bp fragment was used to independently screen 4000 E. Coli 294 transformants in the same manner. 50 colonies were identified which hybridized to different extents with this probe. One contained the Le-IF G fragment, one contained the Le-IF H fragment, and one contained a fragment designated Le-IF H1, an apparent allele of Le-IF H. The hybrid plasmids which result are designated "pLe-IF H", etc.

I. Isolation and DHJA Sequencing of a First Full-Length Le-IF Gene Fragment from pLi-39

Plasmid DNA was prepared from all 39 potential Le-IF cDNA clones and rescreened with the same 260 b.p. DNA probe using the dot hybridization procedure (23). Three plasmids (pL4, pL31, pL34) gave very strong hybridization signals, four (pL13, pL30, pL32, pL36) hybridized moderately, and three (pL6, pL8, pL14) hybridized weakly with the probe.

Figure 2:
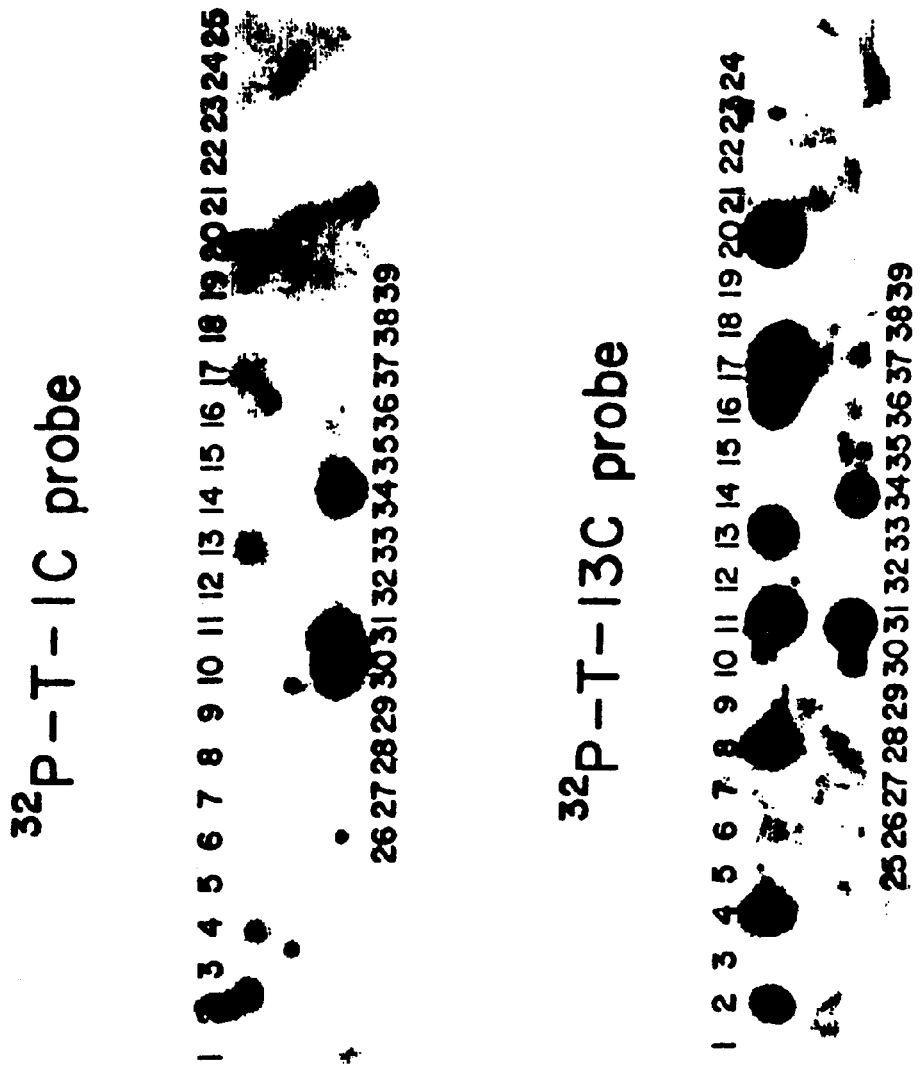
FIG. 2 is an autoradiogram showing hybridization of potential Le-IF plasmids with $^{32}$P-labelled synthetic deoxyoligonucleotides.

The 39 potential Le-IF cDNA recombinant plasmids were also screened by using $^{32}$P-labelled synthetic undecamers (individual T-1 primer pools or individual T-13 primers) directly as hybridization probes. The hybridization conditions were chosen such that perfect base pairing should be required for detectable hybridization signals (28). Thus, plasmid DNA from the 39 clones was prepared by a standard cleared lysate procedure (29) and purified by Biorad Agarose A-50 column chromatography. Samples (3 µg) of each prep were linearized by treatment with Eco RI, denatured in alkali and spotted on 2 separate nitrocellulose filters (1.5 µg per spot) (23). Individual synthetic deoxyoligonucleotide primers and primer pools were phosphorylated with ($\gamma^{32}$P) ATP as follows: 50 pmoles of oligonucleotide and 100 pmoles of ($\gamma^{32}$P) ATP (New England Nuclear, 2500 Ci/mmole) were combined in 30 µl of 60 mM Tris-HCl (pH8), 10 mM MgCl$_2$, 15 mM β-merceptothanol. 2 units of T4 polynucleotide kinase were added and, after 30' at 37° C., $^{32}$P labelled primers were purified by chromatography on 10 ml Sephadex G-50 columns. Hybridizations were performed using $10^6$ cpm, of primer T-13C or 3×$10^6$ cpm of primer pool T-1C. The hybridizations were performed at 15° C. for 14 hours in 6xSSC, 10X Denhardt's solution, as described by Wallace et al. (28). Filters were washed for 5' (3 times) at 0° C. in 6xSSC, dried, and exposed to x-ray film. Results are shown in FIG. 2 for $^{32}$P primer pool T-13C and primer T-1C.

Plasmid DNA from clone 104 was found to give significant hybridization with primer pool T-1C and primer T-13C, but no detectable hybridization with the other undecamers. As shown in FIG. 2, several of the 39 potential Le-IF plasmids (pL2, 4, 13, 17, 20, 30, 31, 34) also hybridized with both of these probes. Restriction analysis showed that only one of these plasmids, pL31, also contained a 260 b.p. internal Bgl II fragment. Pst I digestion of pL31 showed the size of the cDNA insert to be approximately 1000 base pairs.

The entire Pst I insert of pL31 was sequenced by both the Maxam-Gilbert chemical method (30) and by dideoxy chain termination procedure (31) after subcloning Sau 3a fragments into an M13 vector. The DNA sequence is shown ("A") in FIGS. 3A–3E. The appropriate translational reading frame could be predicted from protein sequence information in hand (4), the known range of Le-IF molecular weights and the relative incidence of stop triplets in the three possible reading frames, and that in turn permitted prediction of the entire Le-IF amino acid sequence, including a pre- or signal peptide. The first ATG translational initiation codon is found 60 nucleotides from the 5' end of the sequence and is followed, 188 codons later, by a TGA termination triplet; there are 342 untranslated nucleotides at the 3' end followed by a poly (A) sequence. The putative signal peptide (presumably involved in the secretion of the mature LeIF from leukocytes) is 23 amino acids long. The 165 amino acids constituting the mature LeIF have a calculated MW of 19,390. We have termed the Le-IF encoded by pL31 "Le-IF A." It can be seen from the sequence data ("A") in FIG. 5 that tryptic peptides T1 and T13 of Le-IF B (4) (FIG. 1) correspond to amino acids 145–149 and 57–61 respectively of the Le-IF A. The actual DNA coding sequences found in these two regions are those represented by primer pool T1-C and primer T13-C as the data shown in FIG. 2 suggested.

J. Direct Expression of a First Mature Leukocyte Interferon

1. Generally

The procedure followed to express Le-IF A directly as a mature interferon polypeptide was a variant of that earlier employed for human growth hormone (18), insofar as it involved the combination of synthetic (N-terminal) and complementary DNAs.

As shown in FIG. 6, a Sau 3a restriction endonuclease site is conveniently located between codons 1 and 2 of Le-IF A. Two synthetic deoxyoligonucleotides were designed which incorporate an ATG translational initiation codon, restore the codon for amino acid 1 (cysteine), and create an Eco RI sticky end. These oligomers were ligated to a 34 b.p. Sau 3a-Ava II fragment of pL31. The resulting 45 b.p. product was ligated to two additional DNA fragments to construct an 865 base pair synthetic-natural hybrid gene which codes for Le-IF A and which is bounded by Eco RI and Pst I restriction sites. This gene was inserted into pBR322 between the Eco RI and Pst I sites to give the plasmid pLe-IF A1.

Plasmid pGM1 carries the *E. coli* tryptophan operon containing the deletion ΔLE1413 (G. F. Miozzari, et al., (1978) *J. Bacteriology* 133, 1457–1466)) and hence expresses a fusion protein comprising the first 6 amino acids of the trp leader and approximately the last third of the trp E polypeptide (hereinafter referred to in conjunction as LE'), as well as the trp D polypeptide in its entirety, all under the control of the trp promoter-operator system. The plasmid, 20 μg, was digested with the restriction enzyme PvuII which cleaves the plasmid at five sites. The gene fragments were next combined with EcoRI linkers (consisting of a self complementary oligonucleotide of the sequence: pCAT-GAATTCATG (SEQ ID NO: 39)) providing an EcoRI cleavage site for a later cloning into a plasmid containing an EcoRI site. The 20 μg of DNA fragments obtained from pGM1 were treated with 10 units $T_4$ DNA ligase in the presence of 200 pico moles of the 5'-phosphorylated synthetic oligonucleotide pCATGAATTCATGi (SEQ ID NO:39) and in 20 μl $T_4$ DNA ligase buffer (20 mM tris, pH 7.6, 0.5 mM ATP, 10 mM $MgCl_2$, 5 mM dithiothreitol) at 4° C. overnight. The solution was then heated 10 minutes at 70° C. to halt ligation. The linkers were cleaved by EcoRI digestion and the fragments, now with EcoRI ends were separated using 5 percent polyacrylamide gel electrophoresis (hereinafter "PAGE") and the three largest fragments isolated from the gel by first staining with ethidium bromide, locating the fragments with ultraviolet light, and cutting from the gel the portions of interest. Each gel fragment, with 300 microliters 0.1xTBE, was placed in a dialysis bag and subjected to electrophoresis at 100 v for one hour in 0.1xTBE buffer (TBE buffer contains: 10.8 gm tris base, 5.5 gm boric acid, 0.09 gm $Na_2EDTA$ in 1 liter $H_2O$). The aqueous solution was collected from the dialysis bag, phenol extracted, chloroform extracted and made 0.2 M sodium chloride, and the DNA recovered in water after ethanol precipitation. The trp promoter-operator-containing gene with EcoRI sticky ends was identified in the procedure next described, which entails the insertion of fragments into a tetracycline sensitive plasmid which, upon promoter-operator insertion, becomes tetracycline resistant.

Plasmid pBRH1 (R. I. Rodriguez, et al., Nucleic Acids Research 6, 3267–3287 [1979]) expresses ampicilin resistance and contains the gene for tetracycline resistance but, there being no associated promoter, does not express that resistance. The plasmid is accordingly tetracycline sensitive. By introducing a promoter-operator system in the EcoRI site, the plasmid can be made tetracycline resistant.

pBRH1 with EcoRI and the enzyme removed by phenol extraction followed by chloroform extraction and recovered in water after ethanol precipitation. The resulting DNA molecule was, in separate reaction mixtures, combined with each of the three DNA fragments obtained above and ligated with $T_4$ DNA ligase as previously described. The DNA present in the reaction mixture was used to transform competent *E. coli* K-12 strain 294 K. Backman et al., Proc Nat'l Acad Sci USA 73, 4174–4198 [1976]) by standard techniques (V. Hershfield et al., Proc Nat'l Acad Sci USA 71, 3455–3459 [1974]) and the bacteria plated on LB plates containing 20 μg/ml ampicillin and 5 μg/ml tetracycline. Several tetracycline-resistant colonies were selected, plasmid DNA isolated and the presence of the desired fragment confirmed by restriction enzyme analysis. The resulting plasmid is designated pBRHtrp.

An EcoRI and BamHI digestion product of the viral genome of hepatitis B was obtained by conventional means and cloned into the EcoRI and BamHI sites of plasmid pGH6 (D. V. Goeddel et al., Nature 281, 544 [1979])) to form the plasmid pHS32. Plasmid pHS32 was cleaved with XbaI, phenol extracted, chloroform extracted and ethanol precipitated. It was then treated with 1 μl *E. coli* polymerase I, Klenow fragment (Boehringer-Mannheim) in 30 μl polymerase buffer (50 mM potassium phosphate pH 7.4, 7mM $MgCl_2$, 1 mM β-mercaptoethanol) containing 0.1 mM dTTP and 0.1 mM dCTP for 30 minutes at 0° C. then 2 hr. at 37° C. This treatment causes 2 of the 4 nucleotides complementary to the 5' protruding end of the XbaI cleavage site to be filled in. See FIG. 10.

Two nucleotides, dC and dT, were incorporated giving an end with two 5' protruding nucleotides. This linear residue of plasmid pHS32 (after phenol and chloroform extraction and recovery in water after ethanol precipitation) was cleaved with EcoRI. The large plasmid fragment was separated from the smaller EcoRI-XbaI fragment by PAGE and isolated after electroelution. This DNA fragment from pHS32 (0.2 μg), was ligated, under conditions similar to those described above, to the EcoRI-Taq I fragment of the tryptophan operon (~0.01 μg), derived from pBRHtrp.

In the process of ligating the fragment from pHS32 to the Eco RI-Taq I fragment, as described above, the Taq I protruding end is ligated to the XbaI remaining protruding end even though it is not completely Watson-Crick base-paired. See FIG. 11.

A portion of this ligation reaction mixture was transformed into E. coli 294 cells, heat treated and plated on LB plates containing ampicillin. Twenty-four colonies were selected, grown in 3 ml LB media, and plasmid isolated. Six of these were found to have the Xba I site regenerated via E. coli catalyzed DNA repair and replication. See FIG. 12.

These plasmids were also found to cleave both with EcoRI and HpaI and to give the expected restriction fragments. One plasmid, designated pTrp 14, was used for expression of heterologous polypeptides, as next discussed.

The plasmid pHGH 107 (D. V. Goeddel et al, Nature, 281, 544, 1979) contains a gene for human growth hormone made up of 23 amino acid codons produced from synthetic DNA fragments and 163 amino acid codons obtained from complementary DNA produced via reverse transcription of human growth hormone messenger RNA. This gene, though it lacks the codons of the "pre" sequence of human growth hormone, does contain an ATG translation initiation codon. The gene was isolated from 10 μg pHCH 107 after treatment with EcoRI followed by E. coli polymerase I Klenow fragment and dTTP and dATP as described above. Following phenol and chloroform extraction and ethanol precipitation the plasmid was treated with BamHI.

The human growth hormone ("HGH") gene-containing fragment was isolated by PAGE followed by electroelution. The resulting DNA fragment also contains the first 350 nucleotides of the tetracycline resistance structural gene, but lacks the tetracyline promoter-operator system so that, when subsequently cloned into an expression plasmid, plasmids containing the insert can be located by the restoration of tetracycline resistance. Because the EcoRI end of the fragment has been filled in by the Klenow polymerase I procedure, the fragment has one blunt and one sticky end, ensuring proper orientation when later inserted into an expression plasmid.

The expression plasmid pTrp14 was next prepared to receive the HGH gene-containing fragment prepared above. Thus, pTrp14 was XbaI digested and the resulting sticky ends filled in with the Klenow polymerase I procedure employing dATP, dTTP, dGTP and dCTP. After phenol and chloroform extraction and ethanol precipitation the resulting DNA was treated with BamHI and the resulting large plasmid fragment isolated by PAGE and electroelution. The pTrp14-derived fragment had one blunt and one sticky end, permitting recombination in proper orientation with the HGH gene containing fragment previously-described.

The HGH gene fragment and the pTrp14 fragment were combined and ligated together under conditions similar to those described above. The filled in XbaI and EcoRI ends ligated together by blunt end ligation to recreate both the XbaI and the EcoRI site. See FIG. 13.

This construction also recreates the tetracycline resistance gene. Since the plasmid pHGH 107 expresses tetracycline resistance from a promoter lying upstream from the HGH gene (the lac promoter), this construction, designated pHGH 207, permits expression of the gene for tetracycline resis-tance under the control of the tryptophan promoter-operator. Thus the ligation mixture was transformed into E. coli 294 and colonies selected on LB plates containing 5 μg/ml tetracycline.

Plasmid pHGH207 was Eco RI digested and the trp promoter containing a 300 b.p. Eco RI fragment recovered by PAGE followed by electroelution. The 300 b.p. Eco RI fragment contains the E. coli trp promoter, operator, and trp leader ribosome binding site but lacks an ATG sequence for initiation of translation. This DNA fragment was cloned into the Eco RI site of pLe-IF A. The construction of the fragment is described in detail in (36).

2. The Tryptophan Control Element

The trp fragment just referred to is an analog of the E. coli tryptophan operon from which the so-called trp attenuator has been deleted, See (36), to controllably heighten expression levels. Expression plasmids containing the modified trp regulon can be grown to predetermined levels in nutrient media containing additive tryptophan in quantities sufficent to repress the promoter-operator system, then be deprived of tryptophan so as to derepress the system and occasion the expression of the intended product (36).

3. Detailed Description

More particularly, and with reference to FIG. 6, 250 μg of plasmid pL31were digested with Pst I and the 1000 b.p. insert isolated by gel electrophoresis on a 6 polyacrylamide gel. Approximately 40 μg of insert was electroeluted from the gel and divided into 3 aliquots for further digestion: a) A 16 μg sample of this fragment was partially digested with 40 units of Bgl II for 45' at 37° C. and the reaction mixture purified on a 6 polyacrylamide gel. Approximately 2 μg of the desired 670 b.p. fragment were recovered. b) Another sample (8 μg) of the 1000 b.p. Pst I insert was restricted with Ava II and Bgl II. One pg of the indicated 150 b.p. fragment was recovered after gel electrophoresis. c) 16 μg of the 1000 b.p. piece was treated with Sau 3a and Ava II. After electrophoresis on a 10 polyacrylamide gel, approximately 0.25 μg (~10 pmole) of the 34 b.p. fragment was recovered. The two indicated deoxyoligonuclectides, 5'-dAATTCATGT (SEQ ID NO: 42) (fragment 1) and 5'-d GATCACACATG (SEQ ID NO: 43) (fragment 2) were synthesized by the phosphotriester procedure (24). Fragment 2 was phosphorylated as follows. 200 μl (~40 pmole) of ($\gamma^{32}$P) ATP (Amersham, 5000 Ci/mmole) was dried down and resuspended in 30 μl of 60 mM Tris-HCl (pH8), 10 mM MgCl$_2$, 15 mM β-merceptoethanol, containing 100 pmoles of DNA fragment and 2 units of T4 polynucleotide kinase. After 15 minutes at 37° C., 1 μl of 10 mM ATP was added and the reaction allowed to proceed another 15 minutes. The mixture was then heated at 70° C. for 15 minutes, combined with 100 pmole of 5'-OH fragment 1 and 10 pmole of the 34 b.p. Sau 3a-Ava II fragment. Ligation was performed for 5 hours at 4° C. in 50 μl of 20 mM Tris-HCl (pH7.5) 10 mM Mg Cl$_2$, 10 nM dithiothreitol, 0.5 mM ATP and 10 units T4 DNA ligase. The mixture was electrophoresed on a 6 polyacrylamide gel and the 45 b.p. product recovered by electroelution. 860,000 Cerenkov cpm were recovered (~30 ng, 1 pmole), combined with 0.5 μg (5 pmoles) of the 150 b.p. Ava II-Bgl II fragment and 1 μg (2 pmoles) of the 670 b.p. Bgl II-Pst I fragment. The ligation was performed at 20° C. for 16 hours using 20 units of T4 DNA ligase. The ligase was inactivated by heating to 65 ° C. for 10 minutes. The mixture was then digested with Eco RI and Pst I to eliminate polymers of the gene. The mixture was purified by 6 percent polyacrylamide gel electrophoresis. 36,000 cpm (~0.04 pmole, 20 ng) of 865 b.p. product were isolated. One-half (10 ng) of this was ligated into pBR322 (0.3 μg) between the Eco RI and Pst I sites. Transformation of E. coli 294 gave 70 tetracycline resistant, ampicillin sensitive tranformants. Plasmid DNA isolated from 18 of these transformants was digested with Eco RI and Pst I. 16 of the 18 plasmids had an Eco RI-Pst I fragment 865 b.p. in length. One µg of one of these, pLe-IF Al, was digested with Eco RI and ligated to a 300 b.p. Eco RI fragment (0.1 µg) containing the E. coli trp promoter and trp leader ribosome binding site, prepared as described above. Transformants containing the trp promoter were identified using a $^{32}$P-trp probe in conjunction with the Grunstein-Hogness colony screening procedure (27). An asymetrically located Xba I site in the trp fragment allowed determination of recombinants in which the trp promoter-was oriented in the direction of the Le-IF A gene.

K. Induction of Interferon Expression and In Vitro Assay

Extracts were prepared for IF assay as follows. One ml cultures were grown in L broth containing 5 µg/ml tetracycline to an $A_{550}$ of about 1.0, then diluted into 25 ml of M9 media containing 5 µg/ml tetracycline. 10 ml samples were harvested by centrifugation when $A_{550}$ reached 1.0 and cell pellets were suspended in 1 ml of 15 percent sucrose, 50 mM Tris-HCl (pH 8.0), 50 mM EDTA. One mg of lysozyme was added and, after 5 minutes at 0° C., cells were disrupted by sonication. The samples were centrifuged 10 minutes at 15,000 rpm in a Sorvall SM-24 rotor. Interferon activity in the supernatants was determined by comparison with Le-IF standards by the cytopathic effect (CPE) inhibition assay (2). To determine the number of IF molecules per cell a Le-IF specific activity of $4 \times 10^8$ units/mg was used (7).

As shown in Table 1, Clone pLe-IF A trp 25, in which the trp promoter was inserted in the desired orientation, gives high levels of activity (as high as $2.5 \times 10^8$ units per liter). As shown in Table 2, the IF produced by E. coli K-12 strain 294/pLe-IF A trp 25 behaves like authentic human Le-IF; it is stable to treatment at pH2 and is neutralized by rabbit anti-human leukocyte antibodies. The interferon has an apparent molecular weight of approximately 20,000.

L. In Vivo Antiviral Activity of Le-IF A

The in vivo efficacy of interferon requires the presence of macrophages and NK cells and the in vivo mode of action appears to involve stimulation of these cells (33). Thus, it remained possible that the interferon produced by E. coli 294/pLe-IF A25, while having antiviral activity in the cell culture assay, would not be active in infected animals. Moreover, the in vivo antiviral activity of the bacterially produced, non-glycosylated Le-IF A might be different from the glycosylated Le-IF derived from human "buffy coat" leukocytes. Therefore the biological activity of bacterially synthesized Le-IF A (~2 Pure) was compared with buffy coat Le-IF (~8 percent pure) in lethal encephalyomyocarditis (EMC) virus infection of squirrel monkeys (Table 3).

TABLE 1

Interferon activity in extracts of E. coli

| E. coli K-12 strain 294 transformed by: | Cell density (cells/ml) | IF Activity units/ml culture | Le-IF molecules per cell |
|---|---|---|---|
| pLe-IF A trp 25 | $3.5 \times 10^8$ | 36,000 | 9,000 |
| pLe-IF A trp 25 | $1.8 \times 10^9$ | 250,000 | 12,000 |

TABLE 2

Comparison of activities of extracts from E. coli 294/pLe-Tr A25 with standard Le-IF

| | Interferon Activity (units/ml) | | |
|---|---|---|---|
| | untreated | pH2 | rabbit anti-human leukocyte antibodies |
| 294/pLeIF-A trp 25 extract | 500 | 500 | <10 |
| Le-IF standard | 500 | 500 | <10 |

[1]The 250,000 U/ml extract of E. coli 294/pLe-IF A trp 25 described in Table 1 was diluted 500-fold with minimal essential medium giving a specific activity of 500 U/ml. A leukocyte interferon standard (Wadley Institute) previously titrated against the NIH leukocyte interferon standard, was also diluted to a final concentration of 500 U/ml. One ml aliquots were adjusted to pH 2 with 1N HCl, incubated at 4° C. for 52 hours, neutralized by addition of NaOH and IF activity determined by the standard CPE inhibition assay. 25 µl aliquots of the 500 U/ml samples (untreated) were incubated with 25 µl of rabbit anti-human leukocyte interferon for 60 at 37° C., centrifuged at 12,000×g for 5 minutes and the supernatant assayed.

TABLE 3

Antiviral effect of various Le-IF preparations against EMC virus infection of squirrel monkeys

| | | Serum p.f.u./ml. | | |
|---|---|---|---|---|
| Treatment | Survivors | day 2 | day 3 | day 4 |
| Control | 0/3 | 10   3 | $3 \times 10^4$   $10^4$ | $>10^5$   $>3.4 \times 10^4$ |
| (bacterial proteins) | | 0 | 0 | 1,200 |
| Bacterial | | 0 | 0 | 0 |
| Le-IF A | 3/3 | 0 | 0 | 0 |
| | | 0 | 0 | 0 |
| Le-IF standard | 3/3 | 0 | 0 | 0 |
| | | 0 | 0 | 0 |
| | | 0 | 0 | 0 |

All monkeys were male (average weight 713 g) and had no EMC virus antibodies prior to infection. The monkeys were infected intramuscularly with $100 \times LD_{50}$ EMC virus (determined in mice). The control treated monkeys died at 134, 158 and 164 hours post-infection. Interferon treatments of $10^6$ units were by the intravenous route at −4, +2, 23, 29, 48, 72, 168 and 240 hours, relative to infection. The bacterial leukocyte interferon was a column chromatography fraction from a lysate of E. coli 294/pLe-IF A25 at a specific activity of $7.4 \times 10^6$ U/mg protein. The control bacterial proteins were an equivalent column fraction from a lysate of E. coli 294/pBR322 at twice the total protein concentration. The leukocyte interferon standard was Sendai virus induced interferon from normal human "buffy-coat" cells, purified chromatographically to a specific activity of $32 \times 10^6$ U/mg protein.

The control monkeys showed progressive lethargy, loss of balance, flaccid paralysis of the hind-limbs and watering of the eyes commencing around 8 hours prior to death. The interferon treated monkeys showed none of these abnormalities; they remained active at all times and developed no viremia (Table 3). The one monkey in the control group which did not develop viremia by 4 days died latest (164 h post-infection) but showed high titers of virus in the heart and brain on post-mortem. The interferon treated monkeys did not develop antibodies to EMC virus as determined 14 and 21 days after infection. These results demonstrate that the antiviral effects of Le-IF preparations in the infected animals can be attributed solely to interferon because the contaminating proteins are quite different in the bacterial and buffy coat preparations.

M. Isolation of cDNAs for Additional Leukocyte Interferons

DNA from the fully characterized Le-IF A cDNA-containing plasmid was excised with Pst I, isolated electrophoretically, and labelled by a published procedure (26) with $^{32}$P. The resulting radioactively labelled DNA was used as a probe to screen additional E. coli 294 transformants, obtained identically as those in Part D, by an in situ colony screening procedure (27). Colonies were isolated which hybridized in varying amounts to the probe. Plasmid DNA from these colonies and the ten hybridizing colonies referred to in Part I above was isolated by Pst cutting and characterized by three different methods. First, these Pst fragments were characterized by their restriction endonuclease digestion patterns with the enzymes Bgl II, Pvu II, and Eco RI. This analysis allowed the classification of at least eight different types (Le-IF A, Le-IF B, Le-IF C, Le-IF D, Le-IF A, Le-IF F, Le-IF G and Le-IF H), shown in FIG. 5, which approximates the location of various restriction cuts relative to the by-now known presequence and coding sequence of Le-IF A. One of these, Le-IF D, is believed to be identical to that reported in (39).

Secondly, certain of the DNAs were tested by a published hybridization selection assay (38) for the ability to selectively remove Le-IF mRNA from poly-A containing KG-1 cell RNA. Le-IF A, B, C and F were positive by this assay. Third, the latter Pst fragments were inserted in an expression plasmid, E. coli 294 transformed with the plasmid, and the fragments expressed. The expression products, believed to have been preinterferons, were all positive by CPE assay for interferon activity, albeit marginally active in the case of the Le-IF-F fragment. In addition to the foregoing, all of the Le-IF types described have been sequenced (See FIG. 3).

N. Direct Expression of a Second Mature Leukocyte Interferon

The sequence of the isolated fragment comprising the gene for mature Le-IF-B shows the first fourteen nucleotides of types A and B to be identical. We accordingly proposed to isolate a fragment from pLe-IF A25 bearing the trp-promoter-operator, ribosome binding site and the start of the Le-IF (A=B) gene, and combine this with the remaining portion of the B sequence in an expression plasmid. The salient restriction maps for the Pst fragment of pL4 (a plasmid comprising the Le-IF B Pst-ended gene depicted in FIG. 5) and pLe-IF A25 are shown, respectively, in FIGS. 7a and 7b.

To obtain the approximately 950 b.p. Sau 3a to Pst I fragment from the sequence shown in FIG. 7a several steps were necessary because of the presence of one or more intervening Sau 3a restriction sites, i.e.:

1. The following fragments were isolated:
  a) 110b b.p. from Sau 3a to Eco RI;
  b) 132 b.p. from Eco RI to Xba;
  c) >700 b.p. from Xba to Pst.

2. Fragments (1a) and (1b) were ligated and cut with Xba and Bgl II to preclude self-polymerization through Sau 3a and Xba end terminals (the relevant Sau 3a site was within a Bgl II site; Bgl II cuts to leave a Sau 3a sticky end). A 242 b.p. fragment was isolated.

3. The product of (2) and (1c) were ligated and cut with Pst I and Bgl II, again to prevent self-polymerization. An approximate 950 b.p. fragment, Sau 3a to Pst I of FIG. 7a, was isolated. This fragment comprised that portion of the Le-IF B gene not common to Le-IF A.

4. An approximate 300 b.p. fragment (Hind III to Sau 3a) comprising the trp promoter-operator, ribosome binding site, ATG start signal and cysteine codon of Le-IF A was isolated from pLe-IF A25.

5. An approximately 3600 b.p. fragment Pst I to Hind III was isolated from pBr 322. This comprised the replicon and encoded tetracycline but not ampicillin resistance.

6. The fragments obtained in steps 3, 4 and 5 were triple-ligated and the resulting plasmid transformed into E. coli K-12 strain 294.

Transformants were miniscreened (37) and plasmid samples were digested with Eco RI. Digests yielded three fragments characteristic of:

1) The Eco RI-Eco RI trp promoter fragment; 2) The internal Eco RI to Eco RI fragment of pL4; and 3) protein translational start signal to Eco RI fragment of pL4.

In CPE assay, bacterial extracts from clones made in the foregoing fashion typically assay at about 10×10$^6$ units interferon activity per liter at A$_{550}$=1. One representative clone prepared in this manner is 294/pLIF B trp 7.

0. Direct Expression of Further Mature Leukocyte Interferons

Additional full-length gene fragments that comprise other Le-IF types may be tailored and placed in expression vehicles for expression as in the case of Le-IF A. Complete sequencing by conventional means will reveal whether a restriction site lies sufficiently near the first amino acid codon of the mature interferon type as to permit convenient resort to the approach employed in part J, supra, for the expression of mature Le-IF A, i.e., elimination of the presequence by restriction cutting and replacement of codons for the N-terminal amino acids lost in presequence elimination by ligation of a synthetic DNA fragment. Failing that, the procedure described in (36) may be employed. Briefly, this entails cleaving the presequence-containing fragment precisely before the point at which the codon for the first amino acid of the mature polypeptide begins, by:

1. converting the double stranded DNA to single-stranded DNA in a region surrounding that point;
2. hybridizing to the single-stranded region formed in step (a) a complementary primer length of single-stranded DNA, the 5' end of the primer lying opposite the nucleotide adjoining the intended cleavage site;
3. restoring that portion of the second strand eliminated in step 1 which lies in the 3' direction from the primer by reaction with DNA polymerase in the presence of adenine, thymine, guanine and cytosine-containing deoxynucleotide triphosphates; and
4. digesting the remaining single-stranded length of DNA which protrudes beyond the intended cleavage point.

A short length of synthetic DNA terminating, at the 3' end of the coding strand, with the translation start signal ATG can then be ligated by, e.g., blunt-end ligation to the resulting tailored gene for the mature interferons and the gene inserted into an expression plasmid and brought under the control of a promoter and its associated ribosome binding site.

In a manner similar to that employed in part N, supra, gene fragments encoding Le-IF-C and Le-IF-D were appropriately configured for direct bacterial expression. The expression strategy for these additional leukocyte interferons included, in each case, resort to the approximately 300 b.p. fragment (Hind III to Sau 3a) comprising the trp promoter-operator, ribosome binding site, ATG start signal and cysteine codon of Le-IF A from pLe-IF A25. To this were combined gene fragments from the additional interferon genes encoding their respective amino acid sequences beyond the initial cysteine common to all. Each resulting plasmid was used to transform *E. coli* K-12 strain 294. Ligations to form the respective genes were as follows:

Le IF-C

Isolate the following fragments from pLe IF-C:

(a) 35 b.p. from Sau 3a to Sau 96

(b) >900 b.p. Sau 96 to Pst (c) Isolate an approximate 300 b.p. fragment (Hind III-Sau 3a) from pLe IF A-25 as in part N (4) supra.

(d) Isolate the approximately 3600 b.p. fragment of part N (5) supra.

Construction (1) Ligate (a) and (c). Cleave with Bgl II, Hind III and isolate the approximately 335 b.p. product.

(2) Triple ligate (1)+(b)+(d) and transform *E. coli* with the resulting plasmid.

A representative clone made in this manner is *E. coli* K-12 strain 294/pLe IF C trp 35.

Le-IF D

Isolate from pLe IF-D:

a) 35 b.p. from Sau 3a to Ava II b) 150 b.p. from Ava II to Bgl II c) approx. 700 b.p. from Bgl II to Pst Isolate from pLe IF A25:

d) 300 b.p. from Hind III to Sau 3a Isolate from PBr 322:

e) approx. 3600 b.p. from Hind III to Pst

Construction (1) ligate (a)+(b), cut with Bgl II and purify a 185 b.p. product (1)

(2) ligate (1)+(d), cut with Hind III, Bgl II, and purify the approx. 500 b.p. product (2).

(3) ligate (2)+(c)+(e) and transform *E. coli* with the resulting plasmid.

A representative clone made in this manner is *E. coli* K-12 strain 294/pLeIF D trp 11.

Le-IF F

The Le-IF F containing fragment may be tailored for direct expression through reassembly made convenient by the complete homology of amino acids 1–13 of Le-IF B and Le-IF F. A trp promoter-containing fragment (a) with appropriately configured ends is obtained from pHGH 207, described above, via Pst I and Xba I digestion followed by isolation of the ca. 1050 b.p. fragment. A second fragment (b) is obtained as the larger of the fragments resulting from Pst I and Bgl II digestion of the plasmid pHKY 10 (36). Fragment (a) contains approximately half the gene encoding amplicillin resistance; fragment (b) contains the remainder of that gene and the entire gene for tetracycline resistance save for the associated promoter. Fragments (a) and (b) are combined via T4 ligase and the product treated with Xba I and Bgl II to eliminate dimerization, forming a fragment (c) comprising the trp promoter-operator and genes for tetracycline and ampicillin resistance.

A fragment (d) of approximately 580 b.p. is obtained by Ava II and Bgl II digestion of pLe IF-F. This comprises codons for amino acids 14–166 of Le-IF F.

A fragment (e) (49 b.p.) is obtained by Xba I and Ava II digestion of pLe-IF B. Fragment (e) encodes amino acids 1–13 of Le-IF F.

Fragments (c), (d) and (e) are triple ligated in the presence of T4 ligase. The cohesive ends of the respective fragments are such that the composite plasmid circularizes correctly, bringing the tetracycline resistance gene under the control of the trp promoter-operator along with the gene for mature Le-IF F, such that bacteria transformed with the desired plasmid may be selected on tetracycline-containing plates. A representative clone prepared in this manner is *E. coli* K-12 strain 294/pLeIF F trp 1.

Le-IF H

The complete Le-IF H gene may be configured for expression as a mature leukocyte interferon as follows:

1. Plasmid pLe-IF H is subjected to Hae II and Rsa I digestion with isolation of the 816 base pair fragment extending front the signal peptide amino acid 10 to the 3' noncoding region.

2. The fragment is denatured and subjected to repair synthesis with Klenow fragment, Klenow et al., *Proc. Natl. Acad. Sci. (USA)* 65, 168 (1970), employing the synthetic deoxyribooligonucleotide primer 5'-dATG TGT AAT CTG TCT. This general procedure is also described by Goeddel et al., U.S. Ser. No. 190,799, filed Sep. 25, 1980.

3. The resulting product is cleaved with Sau 3a and a 452 base pair ("bp") fragment representing amino acids 1 to 150 isolated.

4. Sau 3a and Pst I digestion of pLeIF H and isolation of the resulting 500 b.p. fragment yields a gene encoding amino acids 150 through the end of the coding sequence.

5. Fragments isolated in steps (3) and (4) are ligated to form a fragment:

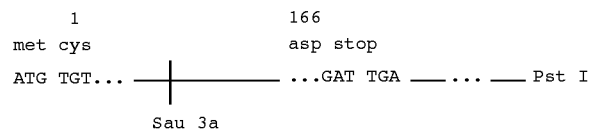

encoding the 166 amino acids of Le-IF H.

6. pLeIF A trp 25 is digested with Xba I, blunt-ended with DNA polymerase I and the product digested with Pst I. The large resulting fragment may be isolated and ligated with the product of step (5) to form an expression plasmid capable, upon transformation of *E. Coli* K-12 strain 294 or other host bacteria, of expressing mature Le-IF H.

LeIF-I

The phage λ Charon 4A recombinant library of the human genome constructed by Lawn et al., *Cell* 15, 1157 (1978), was screened for leukocyte interferon genes by procedures described by Lawn et al., Supra and Maniatis et al., *Cell* 15, 687 (1978). A radioactive LeIF probe derived from the cDNA clone LeIF A (Goeddel et al., *Nature* 287, 411 (1980), was used to screen approximately 500,000 plaques. Six LeIF genome clones were obtained in this screening. Following rescreening and plaque purification, one of these clones, λHLeIF2, was selected for further analysis.

Using the method described above. other probes can be used to advantage to isolate additional LeIF clones from the human genome. These, in turn, can be employed to produce additional leukocyte interferon proteins in accordance with this invention.

1. The 2000 base pair Eco RI fragment of the genomic clone (λHLeIF2) was subcloned into pBR325 at the Eco RI site. The resulting plasmid LeIF I was cleaved with Eco RI and the 2000 base pair fragment isolated. The deoxyoligo-nucleotide dAATTCTGCAG (SEQ ID NO: 49) (an Eco RI>Pst I convertor) was ligated to the 2000 base pair Eco RI fragment and the resulting product cleaved with Pst I to give a 2000 base pair fragment containing Pst I ends. This was cleaved wtih Sau 96 and a 1100 base pair fragment isolated which has one Pst I end and one Sau 96 end.

2. The plasmid pLeIF C trp 35 was digested with Pst I and Xba I. The large fragment was isolated.

3. The small Xba I-Pst I fragment from pLeIF C trp 35 was digested with Xba I and Sau 96. A 40 base pair Xba I-Sau 96 fragment was isolated.

4. The fragments isolated in steps 1), 2) and 3) were ligated to form the expression plasmid pLeIF I trp 1.

LeIF-J

1. The plasmid pLeIF J contains a 3.8 kilobase Hind III fragment of human genomic DNA which includes the LeIF J gene sequence. A 760 base pair Dde I-Rsa I fragment was isolated from this plasmid.

2. The plasmid pLeIF B trp 7 was cleaved with Hind III and Dde I and a 340 bp Hind III-Dde I fragment isolated.

3. The plasmid pBR322 was cleaved with Pst I, blunt ended by incubation with DNA Pol I (Klenow fragment), then digested with Hind III. The large (~3600 bp) fragment was isolated.

4. Fragments isolated in steps 1), 2) and 3) were ligated to form the expression plasmid pLeIF J trp 1.

P. Purification

The content of leukocyte interferon in bacterial extracts may be enhanced by successive:

1. polyethylene-amine precipitation, in which most of the cellular protein, including the interferon, remains in the supernatant;

2. ammonium sulfate fractionation, in which interferon comes out of solution in 55 saturated ammonium sulfate;

suspension of the ammonium sulfate pellet in 0.06 M potassium phosphate, 10 mM tris-HCl, pH 7.2, and dialysis against 25 nM tris-HCl, pH 7.9 (interferon activity remains in solution); and 4. Loading the above supernatant, pH adjusted to 8.5, on a DEAE-cellulose (Whatman DE-53) column and eluting with a linear gradient of 0 to 0.2M NaCl in 25 mM tris HCl pH 8.5.

5. Adsorption on Cibachrome Blue Agarose (Amicon Blue A) or hydroxyapatitie and elution with high salt (1.5 M KCl or 0.2 M phosphate respectively)—optional.

6. Molecular sizing on a Sephadex G-75 column.

7. Cation exchange chromatography on CM-cellulose (Whatman CM-52) in 25 mM ammonium acetate at pH5.0, developed with an ammonium acetate gradient (to 0.2 M. ammonium acetate).

In our hands, the above process gives essentially homogeneous material (e.g. >95 percent pure).

The material can also be further purified by further steps such as, in succession:

8. Size exclusion chromatography;

9. Reverse phase (RP-8) high pressure liquid chromatography; and if desired

10. Affinity chromatography on immobilized antiinterferon antibodies.

Affinity chromatography on a monoclonal antibody column can be used as an alternative to the Step 6 Sephadex G-75 column above. The material from step 4 is loaded on the monoclonal antibody column, prepared as described by Milstein, C., *Scientific American* 243, No. 4, p. 66 (1980), and eluted with 0.2 M) acetic acid 0.1 percent triton and 0.15 M NaCl.

In an alternative, preferred embodiment, the leukocyte interferon produced by the procedures described herein can be purified by the following steps:

1. Frozen cell pellets containing the expressed leukocyte interferon are broken up manually or by appropriate size reduction equipment. The partially thawed cells are suspended in 4 volumes of buffer A. The suspension is held to approximately 40° C.

Buffer A:
0.1 M Tris adjusted to pH 7.5–8.0
10% (w/v) sucrose
0.2 M NaCl
5 mM EDTA
0.1 mM PMSF
10–100 mM $MgCl_2$ The suspension is passed through a Manton Gaulin laboratory homogenizer at about 6000 psi followed by a second pass at less than 1000 psi. Effluent from the homogenizer from both passes is cooled in an ice bath.

2. Polyethylene-imine (PEI) (e.g. Polymin P) is added slowly to the homogenate to a concentration of about 0.35% and allowed to stand for about 30 min. The solids are removed by centrifugation or filtration. This step is temperature controlled or performed sufficiently quickly that the supernatant (filtrate) is kept at less than 10° C. The supernatant (filtrate) is concentrated by ultrafiltration, e.g. on a Millipore Pellicon cassette system (PTGC, 5 ft.$^2$, MWCO 10,000), to approximately 1/10 the original volume. Particulate matter or haziness in the retentate may be removed by an appropriate filter such as a microporous membrane.

3. The clarified solution is loaded directly onto a monoclonal antibody column at a flux of 5–8 cm/hr. (e.g. 25–40 ml/hr. on 2.6 cm Diam column). After loading the column is washed with approximately 10 column volumes of 25 mM Tris HCl, pH 7.5–8.5 including NaCl (0.5M) and surfactant such as Triton X-100 (0.2%) or equivalent. Following the wash the column is rinsed with about 10 column volumes of solution containing 0.15 M NaCl and surfactant such as Triton X-100 (0.1%) or equivalent. The column is eluted with 0.2 M acetic acid containing surfactant such as Triton X-100 (0.1%) or equivalent. The protein peak from the monoclonal antibody column (as determined by UV absorbence or other convenient assay) is pooled and the pH1 adjusted to approximately 4.5 with 1 N NaOH or 1.0 M Tris base. 4. The pooled interferon peak is loaded onto a cationic exchanger such as Whatman CM52 cellulose or equivalent which has been equilibrated with suitable buffer such as ammonium acetate pH 4.5 (50 mM). After loading, the column is washed with equilibrating buffer until the UV absorbence of the effluent has reached a plateau so that little additional protein is eluting from the column. The column is then eluted with 25 mM ammonium acetate/0.12 M sodium chloride or a combination which optimizes recovery of interferon and affords a lyophilized cake having satisfactory appearance and solubility properties.

The monoclonal antibodies employed in the preferred embodiment described above can be prepared by the procedures described by Staehelin, et. al., *P.N.A.S.*, 78, pp. 1848–52 (1981). Monoclonal antibodies are purified and covalently linked to Affigel-10 as described below:

Preparation and Purification of Monoclonal Antibodies from Ascitic Fluid

Five female Balb/c mice were each inoculated with 5 to $10 \times 10^6$ hybridoma cells from mid-log growth phase. About $5 \times 10^6$ viable cells obtained from the mouse producing fluid were inoculated intraperitoneally into each of 10 or more mice. The ascitic fluid was collected repeatedly (2 to 4 times) from each mouse. Up to three transfers and collections may be performed from one group of mice to the next. Ascitic fluid from mice at each transfer was pooled.

Cells and debris were removed from the ascitic fluid by low speed centrifugation (500–1000×g) for 15 min. Then centrifugation was performed for 90 min. at 18,000 rpm in the SS34 Sorvall rotor without braking. The supernatant was frozen and stored at −20° C. After thawing, additional fibrin and particulate material were removed by centrifugation at 35,000 rpm for 90 min. in the Type 35 Spinco rotor. Batches of ascitic fluid from each transfer were tested for specific antibody activity by a solid phase antibody-binding assay (Staehelin, et. al., *P.N.A.S.*, 78, pp. 1848–52 (1981) and pooled if found satisfactory.

Concentration of protein in the pooled solutions was estimated by the approximation that 1 mg of protein yields an absorbance of 1.2 at 280 nm in a cuvette with a path length of 1.0 cm. Ascites fluids with high levels of antibody contain 30 to 35 mg protein/ml. This is equivalent to 4–7 mg of specific antibody/ml. The fluid was diluted with PBS (0.01 M sodium phosphate, pH 7.3, 0.15 M NaCl) to a protein concentration of 10 to 12 mg/ml (12 to 15 $A_{280}$ units/ml).

To each 100 ml of diluted solution, 90 ml of room temperature saturated ammonium sulfate solution was added slowly with vigorous stirring at 0° C. The suspension was kept in ice for 40 to 60 min., then centrifuged for 15 min. at 10,000 rpm in a Sorvall GS-A rotor at 40° C. The supernatant was decanted and drained well. The protein pellets were dissolved in 0.02 M Tris.HCl (pH 7.9)/0.04 M NaCl (Buffer A; about 5 ml per 250 ml centrifuge bottle). The protein solution was dialyzed for 16 to 18 hrs. at room temperature against 100 volumes of Buffer A with at least one change of the buffer. The dialyzed solution was centrifuged at 15,000 rpm in a SS34 Sorvall rotor for 10 min. to remove undissolved material. About 30% to 35% of the original amount of total protein in the ascitic fluid was recovered as estimated by absorption at 280 nm.

The solution containing 30 to 40 mg of protein per ml was then applied to a column of DEAE-cellulose (DE52, Whatman) equilibrated with Buffer A. A column bed volume of at least 100 ml was used for each gram of protein applied. The antibody was eluted from the column with a linear NaCl gradient containing 0.02 M Tris.HCl, pH7.9, from 0.04 M to 0.5 M NaCl. Pooled peak fractions eluting between 0.06 and 0.1 M NaCl were concentrated by precipitation with an equal volume of room temperature saturated ammonium sulfate and centrifugation. The protein pellets were dissolved in 0.2 M NaHCO$_3$ (pH~8.0)/0.3 M NaCl (Buffer B) followed by dialysis against three changes of the same buffer at room temperature. The dialyzed solutions were centrifuged at 20,000×g for 15 min. to remove any insoluble material. Protein concentration was adjusted to 20 to 25 mg/ml with Buffer B. SDS-polyacrylamide gel electrophoresis of representative monoclonal antibodies is shown in FIG. 1.

Preparation of Immunoadsorbants

Affigel-10 (BioRad Laboratories, Richmond, Calif.) was washed on a sintered glass filter three times with ice-cold isopropanol followed by three washes with ice-cold distilled water. The gel slurry (~50% in cold water) was transferred to plastic tubes and sedimented by a brief centrifugation. The supernatant was aspirated. The packed gel was mixed with an equal volume of purified antibody solution and rotated end-over-end at 4° C. for 5 hrs. After reaction, the gel was centrifuged, then washed twice with Buffer C (0.1 M NaHCO$_3$/0.15 M NaCl) to remove uncoupled antibody. Protein determination of the combined washes revealed that more than 90% of antibody was coupled to the gel.

To block unreacted sites, the gel was mixed with an equal volume of 0.1 M ethanolamine.HCl (pH 8) and rotated end-over-end at room temperature for 60 min. The gel slurry was wished free of reactants with PBS and stored in PBS in the presence of 0.02% (w/v) sodium azide at 4° C.

Le-IF may be parenterally administered to subjects requiring antitumor, or antiviral treatment, and to those exhibiting immunosuppressive conditions. Dosage and dose rate may parallel that currently in use in clinical investigations of human derived materials, e.g., about $(1–10) \times 10^6$ units daily, and in the case of materials of purity greater than 1 percent, likely up to, e.g., $50 \times 10^6$ units daily. Preliminary indications in the monkey study described above suggest that dosages of bacterially obtained Le-IF could be significantly elevated for greater effect owing to the essential absence of human proteins other than Le-IF, Which proteins in leukocyte-derived materials may act as pyrogens, exhibiting adverse effects, e.g., malaise, temperature elevation, etc.

As one example of an appropriate dosage form for essentially homogeneous bacterial Le-IF in parenteral form, 3 mg. Le-IF of specific activity of, say, $2 \times 10^8$ U/mg may be dissolved in 25 ml. 5 N serum albumin (human)-USP, the solution passed through a bacteriological filter and the filtered solution aseptically subdivided into 100 vials, each containing $6 \times 10^6$ units pure interferon suitable for parenteral administration. The vials are preferably stored in the cold (−20° C.) prior to use.

The compounds of the present invention can be formulated according to known methods to prepare pharmaceutically useful compositions, whereby the polypeptide hereof is combined in admixture with a pharmaceutically acceptable carrier vehicle. Suitable vehicles and their formulation are described in Remington's *Pharmaceutical Sciences* by E. W. Martin, which is hereby incorporated by reference. Such compositions will contain an effective amount of the interferon protein hereof together with a suitable amount of vehicle in order to prepare pharmaceutically acceptable compositions suitable for effective administration to the host. One preferred mode of administration is parenteral.

REFERENCES

1. Isaacs, A. and Lindenmann, J. *Proc. R. Soc. B*147, 258–267 (1957).
2. Stewart, W. E. II *The Interferon System*, Springer, N.Y. (1979).
3. U.S. Pat. No. 3,699,222.
4. U.S. patent application Ser. No. 106,644 filed Dec. 26, 1979 by S. Pestka and M. Rubenstein, assigned to Hoffman LaRoche, Inc.
5. K. Itakura et. al, *Science* 198, 1056 (1971).
6. Cavalieri, R. L., Havell, E. A., Vileck, J. and Pestka, S. *Proc. Natn. Acad. Sci. U.S.A.* 74, 3287–3291 (1977).
7. Rubinstein, M., Rubinstein, S., Familletti, P. C., Miller, R. S., Waldman, A. A. and Pestka, S. *Proc. Natn. Acad. Sci. U.S.A.* 76, 640–644 (1979).
8. Zoon, K. C., Smith, M. E., Bridgen, P. J., zur Nedden, D. and Anfinsen, C. B. *Proc. Natn. Acad. Sci. U.S.A.* 76, 5601–5605 (1979).

9. D. V. Goeddel et. al, *Proc. National Academy of Sciences*, USA 76, 106 (1979).
10. G. B. Patent Publication No. 2 007 676 A.
11. U.S. Pat. No. 4,190,495.
12. British Patent Publication No. 2055382A.
13. (No reference)
14. Chirgwin, J. M. et. al (1979) *Biochemistry* 18, 5294.
15. Koeffler, H. P. and Golde, D. W. *Science* 200, 1153–1154 (1978).
16. Green, M. et. al (1976) *Arch. Biochem. Biophys.* 172, 74–89.
17. Wickens, M. P., Buell, G. N. and Schimke, R. T. *J. Biol. Chem.* 253, 2483–2495 (1978).
18. Goeddel, D. V., Heyneker, H. L., Hozumi, T., Arentzen, R., Itakura, K., Yansura, D. G., Ross, M. J., Miozzari, G., Crea, R. and Seeburg, P. H. *Nature* 281, 544–548 (1979).
19. Chang, A. C. Y., Nunberg, J. H., Kaufman, R. J., Erlich, H. A, Schimke, R. T. and Cohen, S. N. *Nature* 275, 617–624 (1978).
20. Bolivar, F., Rodriguez, R. L., Greene, P. J., Betlach, M. C., Heyneker, H. L., Boyer, H. W., Crosa, J. H. and Falkow, S. *Gene*, 95–113 (1977).
21. Okuyuma, A. et. al (1978) *Arch. Biochem. Biophys.* 188, 98.
22. Birnboim., H. C. and Doly, J. *Nucleic Acids Res.* 7, 1513–1523 (1979).
23. Kafatos, F. C., Jones, C. W. and Efstratiadis, A. *Nucleic Acids Res.* 7, 1541–1552 (1979).
24. Crea, R., Kraszewski, A., Hirose, T. and Itakura, K. *Proc. Natn. Acad. Sci. U.S.A.* 75, 5765–5769 (1978).
25. Noyes, B., Mevarech, M., Stein, R. and Agarwal, K. L. *Proc. Natn. Acad. Sci. U.S.A.* 76, 1770–1774 (1979).
26. Taylor, J. M., Illemensee, R. and Summers, S. *Biochim. Biophys. Acta* 442, 324–330 (1976).
27. Grunstein, M. and Hogness, D. S., *Proc. Natn. Acad. Sci. U.S.A.* 72, 3961–3965 (1975).
28. Wallace, R. B., Shaffer, J., Murphy, R. F., Bonner, J. and Itakura, K. *Nucleic Acids Res.* 6, 3543–3557 (1979).
29. Clewell, D. B. and Helinski, D. R. *Biochemistry* 9, 4428–4440 (1970).
30. Maxam, A. M. and Gilbert, W. *Methods Enzymol.* 65, 499–560 (1980).
31. Smith, A. J. H. *Methods Enzymol.* 65, 560–580 (1980).
32. Lillenhaug, J. R. et. al (1976) *Biochemistry* 15, 1858
33. Herberman, R. B., Djeu, J. V., Ortaldo, J. R., Holden, H. T., West, W. H. and Bonnard, G. D. *Cancer Treat. Rep.* 62, 1893–1896 (1978); Gidlund, M., Orn, A., Wigzell, H., Senik, A. and Gressor, I. *Nature* 273, 759–761 (1978); Stebbing, N., Dawson, K. M. and Lindley, I. J. D. *Infect. Immun.* 19, 5–11 (1978).
34. Clewell, D. B. (1970) *Biochemistry* 9, 4428.
35. Radloff, R. et. al (1967) *Proc. Natl. Acad. Sci. U.S.A.* 57, 1514. 136.
36. U.S. patent application Ser. No. 06/133,296 filed Mar. 24, 1980 by Dennis G. Kleid et. al, assigned to Genentech, Inc.
37. Birnboim, H. C. and Doly, J., *Nucleic Acids Research* 7, 1513 (1979)
38. Cleveland, D. W. et. al (1980) *Cell* 20, 95
39. Nagata, S. et. al, *Nature* 284, 316 (1980)

What is claimed is:

1. A polypeptide of about 165–166 amino acids comprising the amino acid sequence of a mature human leukocyte interferon microbially produced and unaccompanied by any corresponding presequence or portion thereof.

2. The polypeptide according to claim 1, wherein the amino acid sequence is SEQ ID NO:45 or SEQ ID NO:71.

3. The polypeptide according to claim 1, wherein the amino acid sequence is SEQ ID NO:46 or SEQ ID NO:72.

4. The polypeptide according to claim 1, wherein the amino acid sequence is SEQ ID NO:47 or SEQ ID NO:73.

5. The polypeptide according to claim 1, wherein the amino acid sequence is SEQ ID NO:48 or SEQ ID NO:74.

6. The polypeptide according to claim 1, wherein the amino acid sequence is SEQ ID NO:49 or SEQ ID NO:75.

7. The polypeptide according to claim 1, wherein the amino acid sequence is SEQ ID NO:50 or SEQ ID NO:76.

8. The polypeptide according to claim 1, wherein the amino acid sequence is SEQ ID NO:51 or SEQ ID NO:77.

9. The polypeptide according to claim 1, wherein the amino acid sequence is SEQ ID NO:53 or SEQ ID NO:78.

10. The polypeptide according to claim 1, wherein the amino acid sequence is SEQ ID NO:55 or SEQ ID NO:79.

11. The polypeptide according to claim 1, wherein the amino acid sequence is SEQ ID NO:54 or SEQ ID NO:80.

12. The polypeptide according to claim 1, wherein the amino acid sequence is SEQ ID NO:55 or SEQ ID NO:81.

13. The polypeptide according to claim 1, wherein the amino acid sequence is SEQ ID NO:56 or SEQ ID NO:82.

14. The polypeptide according to claim 1, wherein the amino acid sequence is SEQ ID NO:57 or SEQ ID NO:83.

15. The polypeptide according to claim 1, wherein the amino acid sequence is SEQ ID NO:58 or SEQ ID NO:84.

16. The polypeptide according to claim 1, wherein the amino acid sequence is SEQ ID NO:59 or SEQ ID NO:85.

17. A composition comprising a polypeptide of about 165–166 amino acids comprising the amino acid sequence of a mature human leukocyte interferon unaccompanied by any corresponding presequence or portion thereof, wherein the composition is free of other human proteins.

18. The composition according to claim 17, wherein the amino acid sequence is SEQ ID NO:45 or SEQ ID NO:71.

19. The composition according to claim 17, wherein the amino acid sequence is SEQ ID NO:46 or SEQ ID NO:72.

20. The composition according to claim 17, wherein the amino acid sequence is SEQ ID NO:47 or SEQ ID NO:73.

21. The composition according to claim 17, wherein the amino acid sequence is SEQ ID NO:48 or SEQ ID NO:74.

22. The composition according to claim 17, wherein the amino acid sequence is SEQ ID NO:49 or SEQ ID NO:75.

23. The composition according to claim 17, wherein the amino acid sequence is SEQ ID NO:50 or SEQ ID NO:76.

24. The composition according to claim 17, wherein the amino acid sequence is SEQ ID NO:51 or SEQ ID NO:77.

25. The composition according to claim 17, wherein the amino acid sequence is SEQ ID NO:52 or SEQ ID NO:78.

26. The composition according to claim 17, wherein the amino acid sequence is SEQ ID NO:53 or SEQ ID NO:79.

27. The composition according to claim 17, wherein the amino acid sequence is SEQ ID NO:54 or SEQ ID NO:80.

28. The composition according to claim 17, wherein the amino acid sequence is SEQ ID NO:55 or SEQ ID NO:81.

29. The composition according to claim 17, wherein the amino acid sequence is SEQ ID NO:56 or SEQ ID NO:82.

30. The composition according to claim 17, wherein the amino acid sequence is SEQ ID NO:57 or SEQ ID NO:83.

31. The composition according to claim 17, wherein the amino acid sequence is SEQ ID NO:58 or SEQ ID NO:84.

32. The composition according to claim 17, wherein the amino acid sequence is SEQ ID NO:59 or SEQ ID NO:85.

33. The polypeptide according to claim 1, wherein the amino acid sequence includes the amino acids specified and positioned as indicated in the sequence "All" of FIG. 4.

34. The polypeptide according to any one of claims 1–16, and 33, wherein the amino-terminal amino acid is methionine.

35. A composition comprising a polypeptide according to any one of claims 1–16 and 33 and soluble microbial proteins.

36. A composition comprising a polypeptide according to any one of claims 1–16 and 33 and soluble bacterial proteins.

37. A composition comprising a polypeptide according to any one of claims 1–16 and 33, wherein the composition is free of other animal proteins.

38. A composition comprising a polypeptide according to any one of claims 1–16 and 33, wherein the composition is free of other mammalian proteins.

39. A composition comprising a polypeptide according to any one of claims 1–16 and 33, wherein the composition is free of other human proteins.

40. The polypeptide according to any one of claims 1–16 and 33, wherein the polypeptide is bacterially produced.

41. The composition according to claim 17, wherein the amino acid sequence includes the amino acids specified and positioned as indicated in the sequence "All" of FIG. 4.

42. The composition according to any one of claims 17–32 and 41, wherein the amino-terminal amino acid of the polypeptide is methionine.

43. The composition according to any one of claims 17–32 and 41, further comprising soluble microbial proteins.

44. The composition according to any one of claims 17–32 and 41, further comprising soluble bacterial proteins.

45. The composition according to any one of claims 17–32 and 41, wherein the composition is free of other animal proteins.

46. The composition according to any one of claims 17–32 and 41, wherein the composition is free of other mammalian proteins.

* * * * *

UNITED STATES PATENT AND TRADEMARK OFFICE
CERTIFICATE OF CORRECTION

PATENT NO. : 6,610,830 B1
DATED : April 26, 2003
INVENTOR(S) : Goeddel et al.

It is certified that error appears in the above-identified patent and that said Letters Patent is hereby corrected as shown below:

Title page,
Item [73], Assignee, please replace "Hoffman-La Roche Inc." with
-- Hoffmann-La Roche Inc. --
Item [*] Notice, please delete the following paragraph, "This patent is subject to a terminal disclaimer."
Item [56], References Cited, OTHER PUBLICATIONS, please replace "Goeddel et al., 1989" with -- Goeddel et al., 1981 --.

Column 6,
Line 22, please insert the following paragraphs
-- The amino acid sequence in the rows labeled "LeIF.B". is, a 189 residue LeIF B polypeptide (SEQ ID NO:18) with a portion of a signal peptide. The amino acid sequence labeled S1-S23 is the signal peptide, and the amino acid sequence labeled 1-166 is the mature LeIf B polypeptide (SEQ ID NO:46).
The amino acid sequence in the rows labeled "LeIF C" is a 189 residue LeIF C polypeptide (SEQ ID NO:19) with an intact signal peptide. The amino acid sequence labeled S1-S23 is the signal peptide, and the amino acid sequence labeled 1-166 is the mature LeIF C polypeptide (SEQ ID NO:47).
The amino acid sequence in the rows labeled "LeIF D" is a 189 residue LeIF D polypeptide (SEQ ID NO:20) with an intact signal peptide. The amino acid sequence labeled S1-S23 is the signal peptide, and the amino acid sequence labeled 1-166 is the mature LeIF D polypeptide (SEQ ID NO:48).
The amino acid sequences in the rows labeled "LeIF E" are fragments of a LeIF E polypeptide including the amino acid sequence labeled S20-101 (SEQ ID NO:21), the amino acid sequence labeled 103-154 (SEQ ID NO:67), and the amino acid sequence labeled 156-166 (SEQ ID NO:68).
The amino acid sequence in the rows labeled "LeIF F" is a 189 residue LeIF F polypeptide (SEQ ID NO:22) with an intact signal peptide. The amino acid sequence labeled S1-S23 is the signal peptide, and the amino acid sequence labeled 1-166 is the mature LeIF F polypeptide (SEQ ID NO:49).
The amino acid sequence in the rows labeled "LeIF G" is a 133 residue fragment of a LeIF G polypeptide (SEQ ID NO:23).
The amino acid sequence in the rows labeled "LeIF H" is a 189 residue LeIF H polypeptide (SEQ ID NO:24) with an intact signal peptide. The amino acid sequence labeled S1-S23 is the signal peptide, and the amino acid sequence labeled 1-166 is the mature LeIF H polypeptide (SEQ ID NO:50). Amino acids common to all LeIFs (excluding the pseudogene LeIF E) are also shown. The underlined residues are amino acids which are also present in human fibroblast interferon. --

UNITED STATES PATENT AND TRADEMARK OFFICE
CERTIFICATE OF CORRECTION

PATENT NO.    : 6,610,830 B1
DATED         : April 26, 2003
INVENTOR(S)   : Goeddel et al.

It is certified that error appears in the above-identified patent and that said Letters Patent is hereby corrected as shown below:

Column 7,
Lines 21-42, please delete the paragraphs.
Line 9, please insert the following paragraphs,
-- The amino acid sequence in the rows labeled "H" is a 189 residue polypeptide (SEQ ID NO:36) with an intact signal peptide. The amino acid sequence labeled S1-S23 is the signal peptide, and the amino acid sequence labeled 1-166 is the mature polypeptide (SEQ ID NO:55).
The amino acid sequence in the rows labeled "I" is a 189 residue polypeptide (SEQ ID NO:37) with an intact signal peptide. The amino acid sequence labeled S1-S23 is the signal peptide, and the amino acid sequence labeled 1-166 is the mature polypeptide (SEQ ID NO:51).
The amino acid sequence in the rows labeled "J" is a 189 residue polypeptide with an intact signal peptide (SEQ ID NO:32). The amino acid sequence labeled S1-S23 is the signal peptide, and the amino acid sequence labeled 1-166 is the mature polypeptide (SEQ ID NO:52).
The amino acid sequences in the rows labeled "C" are two polypeptide fragments. The amino acid sequence labeled S1-S19 is a 19 residue polypeptide (SEQ ID NO:70), and the amino acid sequence labeled S21-166 is a 169 residue; polypeptide (SEQ ID NO:38). The amino acid sequence labeled 1-166 of SEQ ID NO:38 is a mature polypeptide (SEQ ID NO:54). --

Column 113,
Line 32, please replace "SEQ ID NO:53" with -- SEQ ID NO:52 --.
Line 34, please replace "SEQ ID NO:55" with -- SEQ ID NO:53 --.

Signed and Sealed this

Fifteenth Day of June, 2004

JON W. DUDAS
*Acting Director of the United States Patent and Trademark Office*

SEQUENCE LISTING

<160> NUMBER OF SEQ ID NOS: 85

<210> SEQ ID NO 1
<211> LENGTH: 958
<212> TYPE: DNA
<213> ORGANISM: Homo sapiens
<220> FEATURE:
<221> NAME/KEY: CDS
<222> LOCATION: (61)...(624)

<400> SEQUENCE: 1

```
tgagcgtaaa ccttaggctc acccatttca accagtctag cagcatctgc aacatctaca      60 atg gcc ttg acc ttt gct tta ctg gtg gcc ctc ctg gtg ctc agc tgc     108
Met Ala Leu Thr Phe Ala Leu Leu Val Ala Leu Leu Val Leu Ser Cys
 1               5                  10                  15 aag tca agc tgc tct gtg ggc tgt gat ctg cct caa acc cac agc ctg     156
Lys Ser Ser Cys Ser Val Gly Cys Asp Leu Pro Gln Thr His Ser Leu
             20                  25                  30 ggt agc agg agg acc ttg atg ctc ctg gca cag atg agg aaa atc tct     204
Gly Ser Arg Arg Thr Leu Met Leu Leu Ala Gln Met Arg Lys Ile Ser
         35                  40                  45 ctt ttc tcc tgc ttg aag gac aga cat gac ttt gga ttt ccc cag gag     252
Leu Phe Ser Cys Leu Lys Asp Arg His Asp Phe Gly Phe Pro Gln Glu
     50                  55                  60 gag ttt ggc aac cag ttc caa aag gct gaa acc atc cct gtc ctc cat     300
Glu Phe Gly Asn Gln Phe Gln Lys Ala Glu Thr Ile Pro Val Leu His
 65                  70                  75                  80 gag atg atc cag cag atc ttc aat ctc ttc agc aca aag gac tca tct     348
Glu Met Ile Gln Gln Ile Phe Asn Leu Phe Ser Thr Lys Asp Ser Ser
                 85                  90                  95
```

-continued

```
gct gct tgg gat gag acc ctc cta gac aaa ttc tac act gaa ctc tac          396
Ala Ala Trp Asp Glu Thr Leu Leu Asp Lys Phe Tyr Thr Glu Leu Tyr
            100                 105                 110 cag cag ctg aat gac ctg gaa gcc tgt gtg ata cag ggg gtg ggg gtg          444
Gln Gln Leu Asn Asp Leu Glu Ala Cys Val Ile Gln Gly Val Gly Val
        115                 120                 125 aca gag act ccc ctg atg aag gag gac tcc att ctg gct gtg agg aaa          492
Thr Glu Thr Pro Leu Met Lys Glu Asp Ser Ile Leu Ala Val Arg Lys
    130                 135                 140 tac ttc caa aga atc act ctc tat ctg aaa gag aag aaa tac agc cct          540
Tyr Phe Gln Arg Ile Thr Leu Tyr Leu Lys Glu Lys Lys Tyr Ser Pro
145                 150                 155                 160 tgt gcc tgg gag gtt gtc aga gca gaa atc atg aga tct ttt tct ttg          588
Cys Ala Trp Glu Val Val Arg Ala Glu Ile Met Arg Ser Phe Ser Leu
                165                 170                 175 tca aca aac ttg caa gaa agt tta aga agt aag gaa tgaaaactgg               634
Ser Thr Asn Leu Gln Glu Ser Leu Arg Ser Lys Glu
            180                 185 ttcaacatgg aaatgatttt cattgattcg tatgccagct cacctttta tgatctgcca         694 tttcaaagac tcatgtttct gctatgacca tgacacgatt taaatctttt caaatgtttt        754
taggagtatt aatcaacatt gtattcagct cttaaggcac tagtcccta cagaggacca         814 tgctgactga tccattatct atttaaatat ttttaaaata ttatttattt aactatttat        874
aaaacaactt atttttgttc atattacgtc atgtgcacct ttgcacagtg gttaatgtaa        934
taaaatatgt tctttgtatt tgct                                               958

<210> SEQ ID NO 2
<211> LENGTH: 188
<212> TYPE: PRT
<213> ORGANISM: Homo sapiens

<400> SEQUENCE: 2

Met Ala Leu Thr Phe Ala Leu Leu Val Ala Leu Leu Val Leu Ser Cys
  1               5                  10                  15

Lys Ser Ser Cys Ser Val Gly Cys Asp Leu Pro Gln Thr His Ser Leu
             20                  25                  30

Gly Ser Arg Arg Thr Leu Met Leu Leu Ala Gln Met Arg Lys Ile Ser
         35                  40                  45

Leu Phe Ser Cys Leu Lys Asp Arg His Asp Phe Gly Phe Pro Gln Glu
     50                  55                  60

Glu Phe Gly Asn Gln Phe Gln Lys Ala Glu Thr Ile Pro Val Leu His
 65                  70                  75                  80

Glu Met Ile Gln Gln Ile Phe Asn Leu Phe Ser Thr Lys Asp Ser Ser
                 85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185
```

180         185

<210> SEQ ID NO 3
<211> LENGTH: 1041
<212> TYPE: DNA
<213> ORGANISM: Homo sapiens
<220> FEATURE:
<221> NAME/KEY: CDS
<222> LOCATION: (32)...(598)

<400> SEQUENCE: 3

```
tactagctca gcagcatggg caacatctac a atg gcc ttg act ttt tat tta        52
                                   Met Ala Leu Thr Phe Tyr Leu
                                    1               5 atg gtg gcc cta gtg gtg ctc agc tac aag tca ttc agc tct ctg ggc      100
Met Val Ala Leu Val Val Leu Ser Tyr Lys Ser Phe Ser Ser Leu Gly
        10                  15                  20 tgt gat ctg cct cag act cac agc ctg ggt aac agg agg gcc ttg ata      148
Cys Asp Leu Pro Gln Thr His Ser Leu Gly Asn Arg Arg Ala Leu Ile
 25                  30                  35 ctc ctg gca caa atg cga aga atc tct cct ttc tcc tgc ctg aag gac      196
Leu Leu Ala Gln Met Arg Arg Ile Ser Pro Phe Ser Cys Leu Lys Asp
 40                  45                  50                  55 aga cat gac ttt gaa ttc ccc cag gag gag ttt gat gat aaa cag ttc      244
Arg His Asp Phe Glu Phe Pro Gln Glu Glu Phe Asp Asp Lys Gln Phe
             60                  65                  70 cag aag gct caa gcc atc tct gtc ctc cat gag atg atc cag cag acc      292
Gln Lys Ala Gln Ala Ile Ser Val Leu His Glu Met Ile Gln Gln Thr
         75                  80                  85 ttc aac ctc ttc agc aca aag gac tca tct gct gct ttg gat gag acc      340
Phe Asn Leu Phe Ser Thr Lys Asp Ser Ser Ala Ala Leu Asp Glu Thr
     90                  95                 100 ctt cta gat gaa ttc tac atc gaa ctt gac cag cag ctg aat gac ctg      388
Leu Leu Asp Glu Phe Tyr Ile Glu Leu Asp Gln Gln Leu Asn Asp Leu
    105                 110                 115 gaa gtc ctg tgt gat cag gaa gtg ggg gtg ata gag tct ccc ctg atg      436
Glu Val Leu Cys Asp Gln Glu Val Gly Val Ile Glu Ser Pro Leu Met
120                 125                 130                 135 tac gag gac tcc atc ctg gct gtg agg aaa tac ttc caa aga atc act      484
Tyr Glu Asp Ser Ile Leu Ala Val Arg Lys Tyr Phe Gln Arg Ile Thr
                140                 145                 150 cta tat ctg aca gag aag aaa tac agc tct tgt gcc tgg gag gtt gtc      532
Leu Tyr Leu Thr Glu Lys Lys Tyr Ser Ser Cys Ala Trp Glu Val Val
            155                 160                 165 aga gca gaa atc atg aga tcc ttc tct tta tca atc aac ttg caa aaa      580
Arg Ala Glu Ile Met Arg Ser Phe Ser Leu Ser Ile Asn Leu Gln Lys
        170                 175                 180 aga ttg aag agt aag gaa tgagacctgg tacaacacgg aaatgattct             628
Arg Leu Lys Ser Lys Glu
    185 catagactaa tacagcagtc tacactttga caagttgtgc tctttcaaag acccttgttt    688 ctgccaaaac catgctatga attgaatcaa atgtgtcaag tgttttcagg agtgttaagc    748 aacatcctgt tcagctgtat gggcactagt cccttacaga tgaccatgct gatggatcta    808 ttcatctatt tatttaaatc tttatttagt taactactat agggacttaa attagttttg    868 ttcatattat attatgtgaa cttttacatt gtgaattgtg taacaaaaac atgttcttat    928 atttattatt ttgccatgtt tattaaattt ttactatgaa aaaattcttt atttattctt    988 taaaattgaa ctccaaccca tgaattgtgc aaactgatta aagaatggat ggt          1041
```

<210> SEQ ID NO 4
<211> LENGTH: 189
<212> TYPE: PRT
<213> ORGANISM: Homo sapiens

<400> SEQUENCE: 4

Met Ala Leu Thr Phe Tyr Leu Met Val Ala Leu Val Val Leu Ser Tyr
1               5                   10                  15

Lys Ser Phe Ser Ser Leu Gly Cys Asp Leu Pro Gln Thr His Ser Leu
            20                  25                  30

Gly Asn Arg Arg Ala Leu Ile Leu Leu Ala Gln Met Arg Arg Ile Ser
        35                  40                  45

Pro Phe Ser Cys Leu Lys Asp Arg His Asp Phe Glu Phe Pro Gln Glu
    50                  55                  60

Glu Phe Asp Asp Lys Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Ala Leu Asp Glu Thr Leu Leu Asp Glu Phe Tyr Ile Glu Leu
            100                 105                 110

Asp Gln Gln Leu Asn Asp Leu Glu Val Leu Cys Asp Gln Glu Val Gly
        115                 120                 125

Val Ile Glu Ser Pro Leu Met Tyr Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Ser Cys Ala Trp Glu Val Val Arg Ala Glu Ile Met Arg Ser Phe Ser
                165                 170                 175

Leu Ser Ile Asn Leu Gln Lys Arg Leu Lys Ser Lys Glu
            180                 185

<210> SEQ ID NO 5
<211> LENGTH: 963
<212> TYPE: DNA
<213> ORGANISM: Homo sapiens
<220> FEATURE:
<221> NAME/KEY: CDS
<222> LOCATION: (46)...(612)

<400> SEQUENCE: 5
aaggttatcc atctcaagta gcctagcaat atttgcaaca tccca atg gcc ctg tcc        57
                                                Met Ala Leu Ser
                                                            1 ttt tct tta ctt atg gcc gtg ctg gtg ctc agc tac aaa tcc atc tgt        105
Phe Ser Leu Leu Met Ala Val Leu Val Leu Ser Tyr Lys Ser Ile Cys
 5                  10                  15                  20 tct ctg ggc tgt gat ctg cct cag acc cac agc ctg ggt aat agg agg        153
Ser Leu Gly Cys Asp Leu Pro Gln Thr His Ser Leu Gly Asn Arg Arg
                25                  30                  35 gcc ttg ata ctc ctg gga caa atg gga aga atc tct cct ttc tcc tgc        201
Ala Leu Ile Leu Leu Gly Gln Met Gly Arg Ile Ser Pro Phe Ser Cys
            40                  45                  50 ctg aag gac aga cat gat ttc cga atc ccc cag gag gag ttt gat ggc        249
Leu Lys Asp Arg His Asp Phe Arg Ile Pro Gln Glu Glu Phe Asp Gly
        55                  60                  65 aac cag ttc cag aag gct caa gcc atc tct gtc ctc cat gag atg atc        297
Asn Gln Phe Gln Lys Ala Gln Ala Ile Ser Val Leu His Glu Met Ile
    70                  75                  80

-continued

```
cag cag acc ttc aat ctc ttc agc aca gag gac tca tct gct gct tgg      345
Gln Gln Thr Phe Asn Leu Phe Ser Thr Glu Asp Ser Ser Ala Ala Trp
 85                  90                  95                 100 gaa cag agc ctc cta gaa aaa ttt tcc act gaa ctt tac cag caa ctg      393
Glu Gln Ser Leu Leu Glu Lys Phe Ser Thr Glu Leu Tyr Gln Gln Leu
                105                 110                 115 aat gac ctg gaa gca tgt gtg ata cag gag gtt ggg gtg gaa gag act      441
Asn Asp Leu Glu Ala Cys Val Ile Gln Glu Val Gly Val Glu Glu Thr
            120                 125                 130 ccc ctg atg aat gag gac tcc atc ctg gct gtg agg aaa tac ttc caa      489
Pro Leu Met Asn Glu Asp Ser Ile Leu Ala Val Arg Lys Tyr Phe Gln
        135                 140                 145 aga atc act ctt tat cta ata gag agg aaa tac agc cct tgt gcc tgg      537
Arg Ile Thr Leu Tyr Leu Ile Glu Arg Lys Tyr Ser Pro Cys Ala Trp
    150                 155                 160 gag gtt gtc aga gca gaa atc atg aga tcc ctc tcg ttt tca aca aac      585
Glu Val Val Arg Ala Glu Ile Met Arg Ser Leu Ser Phe Ser Thr Asn
165                 170                 175                 180 ttg caa aaa aga tta agg agg aag gat tgaaaactgg ttcaacatgg            632
Leu Gln Lys Arg Leu Arg Arg Lys Asp
                185 caatgatcct gattgactaa tacattatct cacactttca cgagttcttc catttcaaag    692 actcacttct ataaccacaa acgcgttgaa tcaaattttt caaatgtttt cagcagtgta    752 aagaagtgtc gtgtatacct gtgcaggcac tagtccttta cagatgacca ttctgatgtc    812 tctgttcatc ttttgtttaa atatttattt aattattttt aaaatttatg taatatcatg    872 agtcccttta cattgtggtt aatgtaacaa tatatgttct tcatatttag ccaatatatt    932 aatttccttt tcattaaaat ttttactata c                                   963

<210> SEQ ID NO 6
<211> LENGTH: 189
<212> TYPE: PRT
<213> ORGANISM: Homo sapiens

<400> SEQUENCE: 6

Met Ala Leu Ser Phe Ser Leu Leu Met Ala Val Leu Val Leu Ser Tyr
  1               5                  10                  15

Lys Ser Ile Cys Ser Leu Gly Cys Asp Leu Pro Gln Thr His Ser Leu
             20                  25                  30

Gly Asn Arg Arg Ala Leu Ile Leu Leu Gly Gln Met Gly Arg Ile Ser
         35                  40                  45

Pro Phe Ser Cys Leu Lys Asp Arg His Asp Phe Arg Ile Pro Gln Glu
     50                  55                  60

Glu Phe Asp Gly Asn Gln Phe Gln Lys Ala Gln Ala Ile Ser Val Leu
 65                  70                  75                  80

His Glu Met Ile Gln Gln Thr Phe Asn Leu Phe Ser Thr Glu Asp Ser
                 85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Ile Glu Arg Lys Tyr Ser
145                 150                 155                 160

Pro Cys Ala Trp Glu Val Val Arg Ala Glu Ile Met Arg Ser Leu Ser
```

```
                    165                 170                 175
Phe Ser Thr Asn Leu Gln Lys Arg Leu Arg Arg Lys Asp
                180                 185

<210> SEQ ID NO 7
<211> LENGTH: 863
<212> TYPE: DNA
<213> ORGANISM: Homo sapiens
<220> FEATURE:
<221> NAME/KEY: CDS
<222> LOCATION: (55)...(621)

<400> SEQUENCE: 7
caaggttcag agtcacccat ctcagcaagc ccagaagtat ctgcaatatg tacg atg         57
                                                             Met
                                                              1 gcc tcg ccc ttt gct tta ctg atg gtc ctg gtg gtg ctc agc tgc aag       105
Ala Ser Pro Phe Ala Leu Leu Met Val Leu Val Val Leu Ser Cys Lys
            5                  10                  15 tca agc tgc tct ctg ggc tgt gat ctg cct gag acc cac agc ctg gat       153
Ser Ser Cys Ser Leu Gly Cys Asp Leu Pro Glu Thr His Ser Leu Asp
         20                  25                  30 aac agg agg acc ttg atg ctc ctg gca caa atg agc aga atc tct cct       201
Asn Arg Arg Thr Leu Met Leu Leu Ala Gln Met Ser Arg Ile Ser Pro
 35                  40                  45 tcc tcc tgt ctg atg gac aga cat gac ttt gga ttt ccc cag gag gag       249
Ser Ser Cys Leu Met Asp Arg His Asp Phe Gly Phe Pro Gln Glu Glu
 50                  55                  60                  65 ttt gat ggc aac cag ttc cag aag gct cca gcc atc tct gtc ctc cat       297
Phe Asp Gly Asn Gln Phe Gln Lys Ala Pro Ala Ile Ser Val Leu His
                 70                  75                  80 gag ctg atc cag cag atc ttc aac ctc ttt acc aca aaa gat tca tct       345
Glu Leu Ile Gln Gln Ile Phe Asn Leu Phe Thr Thr Lys Asp Ser Ser
             85                  90                  95 gct gct tgg gat gag gac ctc cta gac aaa ttc tgc acc gaa ctc tac       393
Ala Ala Trp Asp Glu Asp Leu Leu Asp Lys Phe Cys Thr Glu Leu Tyr
        100                 105                 110 cag cag ctg aat gac ttg gaa gcc tgt gtg atg cag gag gag agg gtg       441
Gln Gln Leu Asn Asp Leu Glu Ala Cys Val Met Gln Glu Glu Arg Val
    115                 120                 125 gga gaa act ccc ctg atg aat gtg gac tcc atc ttg gct gtg aag aaa       489
Gly Glu Thr Pro Leu Met Asn Val Asp Ser Ile Leu Ala Val Lys Lys
130                 135                 140                 145 tac ttc cga aga atc act ctc tat ctg aca gag aag aaa tac agc cct       537
Tyr Phe Arg Arg Ile Thr Leu Tyr Leu Thr Glu Lys Lys Tyr Ser Pro
                150                 155                 160 tgt gcc tgg gag gtt gtc aga gca gaa atc atg aga tcc ctc tct tta       585
Cys Ala Trp Glu Val Val Arg Ala Glu Ile Met Arg Ser Leu Ser Leu
            165                 170                 175 tca aca aac ttg caa gaa aga tta agg agg aag gaa taatatctgg             631
Ser Thr Asn Leu Gln Glu Arg Leu Arg Arg Lys Glu
        180                 185 tccaacatga aacaattct tattgactca taccaggt cacgctttca tgaattctgt         691
catttcaaag actctcaccc ctgctataac tatgaccatg ctgataaact gatttatcta     751
tttaaatatt tatttaacta ttcataagat ttaaattatt tttgttcata taacgtcatg     811 tgcacccttta cactgtggtt agtgtaataa aacatgttcc ttatatttac tc            863

<210> SEQ ID NO 8
<211> LENGTH: 189
```

```
<212> TYPE: PRT
<213> ORGANISM: Homo sapiens

<400> SEQUENCE: 8

Met Ala Ser Pro Phe Ala Leu Leu Met Val Leu Val Leu Ser Cys
 1               5                  10                  15

Lys Ser Ser Cys Ser Leu Gly Cys Asp Leu Pro Glu Thr His Ser Leu
                20                  25                  30

Asp Asn Arg Arg Thr Leu Met Leu Leu Ala Gln Met Ser Arg Ile Ser
            35                  40                  45

Pro Ser Ser Cys Leu Met Asp Arg His Asp Phe Gly Phe Pro Gln Glu
    50                  55                  60

Glu Phe Asp Gly Asn Gln Phe Gln Lys Ala Pro Ala Ile Ser Val Leu
65                  70                  75                  80

His Glu Leu Ile Gln Gln Ile Phe Asn Leu Phe Thr Thr Lys Asp Ser
                85                  90                  95

Ser Ala Ala Trp Asp Glu Asp Leu Leu Asp Lys Phe Cys Thr Glu Leu
                100                 105                 110

Tyr Gln Gln Leu Asn Asp Leu Glu Ala Cys Val Met Gln Glu Glu Arg
            115                 120                 125

Val Gly Glu Thr Pro Leu Met Asn Val Asp Ser Ile Leu Ala Val Lys
130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Leu Ser Thr Asn Leu Gln Glu Arg Leu Arg Arg Lys Glu
            180                 185

<210> SEQ ID NO 9
<211> LENGTH: 876
<212> TYPE: DNA
<213> ORGANISM: Homo sapiens
<220> FEATURE:
<221> NAME/KEY: CDS
<222> LOCATION: (1)...(510)

<400> SEQUENCE: 9 ctg cct ctg ggc tgt gat ctg cct cag gcc cac agc gtg ggt aac agg     48
Leu Pro Leu Gly Cys Asp Leu Pro Gln Ala His Ser Val Gly Asn Arg
 1               5                  10                  15 agg gcc ttc ata ctc ctg aca caa atg agg aga atc tct cct ttt tct     96
Arg Ala Phe Ile Leu Leu Thr Gln Met Arg Arg Ile Ser Pro Phe Ser
                20                  25                  30 tac ctg aag gac aga cat gac ttt gat ttt cca tca tca ggt gtt tca    144
Tyr Leu Lys Asp Arg His Asp Phe Asp Phe Pro Ser Ser Gly Val Ser
            35                  40                  45 tgg caa cca ctt cca gaa ggt tca agc tat ctt cct ttt cca tga gat    192
Trp Gln Pro Leu Pro Glu Gly Ser Ser Tyr Leu Pro Phe Pro  *  Asp
    50                  55                  60 gat gca gca gac ctt caa cct ctt cag cac aaa gga ctc atc tga tac    240
Asp Ala Ala Asp Leu Gln Pro Leu Gln His Lys Gly Leu Ile  *  Tyr
65                  70                  75 ttg gga tga gac cct ttt aga caa atc cta cac tga act tta cca gca    288
Leu Gly  *  Asp Pro Phe Arg Gln Ile Leu His  *  Thr Leu Pro Ala
        80                  85                  90 gct gaa tga cct gga agc ctg tgt gat gta gaa ggt tgg agt gga aga    336
Ala Glu  *  Pro Gly Ser Leu Cys Asp Val Glu Gly Trp Ser Gly Arg
        95                  100                 105
```

-continued

```
gac tcc cct gag gaa tgt gga ctc cat cct ggc tgt gag aaa ata ctt      384
Asp Ser Pro Glu Glu Cys Gly Leu His Pro Gly Cys Glu Lys Ile Leu
        110                 115                 120 tca aag aat cac tct tta tct gac aaa gaa gaa gta tag ccc ttg ttc      432
Ser Lys Asn His Ser Leu Ser Asp Lys Glu Glu Val  *  Pro Leu Phe
125                 130                 135 ctg gga ggc tgt cag agc aga aat cat gag atc ctt ctc ttt atg aac      480
Leu Gly Gly Cys Gln Ser Arg Asn His Glu Ile Leu Leu Phe Met Asn
        140                 145                 150 gaa ctt gca gga aag att aag gag gaa gga atgaaaactg gttcaacatg        530
Glu Leu Ala Gly Lys Ile Lys Glu Glu Gly
155                 160 gaaatgagaa acatttccat gattaataca tcatctcaca cattcatgaa ttctgccatt    590
tgtcattttt gctatatcca tgacatgagt tgaatcaaaa ttttaaaatg ttttcaggaa    650
tgttaagcag catcatgttc agctgtacag gcactagttc cttacggatg atcatgctga    710
tggatctgtt tatctatttg tctaaataat tatttaacta tttataatat ttaaaatctt    770
cttttcatgt atcatgtatt tttactttgt ggtaatata acaacacatg ttctttatat     830
ttagtcaata tattactttg ctttttttcat taaatttta ctatgg                    876
```

<210> SEQ ID NO 10
<211> LENGTH: 62
<212> TYPE: PRT
<213> ORGANISM: Homo sapiens

<400> SEQUENCE: 10

```
Leu Pro Leu Gly Cys Asp Leu Pro Gln Ala His Ser Val Gly Asn Arg
1               5                   10                  15

Arg Ala Phe Ile Leu Leu Thr Gln Met Arg Arg Ile Ser Pro Phe Ser
            20                  25                  30

Tyr Leu Lys Asp Arg His Asp Phe Asp Phe Pro Ser Ser Gly Val Ser
        35                  40                  45

Trp Gln Pro Leu Pro Glu Gly Ser Ser Tyr Leu Pro Phe Pro
    50                  55                  60
```

<210> SEQ ID NO 11
<211> LENGTH: 985
<212> TYPE: DNA
<213> ORGANISM: Homo sapiens
<220> FEATURE:
<221> NAME/KEY: CDS
<222> LOCATION: (9)...(575)

<400> SEQUENCE: 11

```
acatccca atg gcc ctg tcc ttt tct tta ctg atg gcc gtg ctg gtg ctc     50
         Met Ala Leu Ser Phe Ser Leu Leu Met Ala Val Leu Val Leu
         1               5                   10 agc tac aaa tcc atc tgt tct ctg ggc tgt gat ctg cct cag acc cac     98
Ser Tyr Lys Ser Ile Cys Ser Leu Gly Cys Asp Leu Pro Gln Thr His
15                  20                  25                  30 agc ctg ggt aat agg agg gcc ttg ata ctc ctg gca caa atg gga aga     146
Ser Leu Gly Asn Arg Arg Ala Leu Ile Leu Leu Ala Gln Met Gly Arg
            35                  40                  45 atc tct cct ttc tcc tgc ctg aag gac aga cat gac ttt gga ttc ccc     194
Ile Ser Pro Phe Ser Cys Leu Lys Asp Arg His Asp Phe Gly Phe Pro
        50                  55                  60 caa gag gag ttt gat ggc aac cag ttc cag aag gct caa gcc atc tct     242
Gln Glu Glu Phe Asp Gly Asn Gln Phe Gln Lys Ala Gln Ala Ile Ser
```

|   |   |   |   |   |   |   |   |   |   |   |   |   |   |   |   |   |
|---|---|---|---|---|---|---|---|---|---|---|---|---|---|---|---|---|
|   |   |   | 65 |   |   |   | 70 |   |   |   | 75 |   |   |   |   |   |
| gtc | ctc | cat | gag | atg | atc | cag | cag | acc | ttc | aat | ctc | ttc | agc | aca | aag | 290 |
| Val | Leu | His | Glu | Met | Ile | Gln | Gln | Thr | Phe | Asn | Leu | Phe | Ser | Thr | Lys |   |
|   |   | 80 |   |   |   |   | 85 |   |   |   |   | 90 |   |   |   |   |
| gac | tca | tct | gct | act | tgg | gaa | cag | agc | ctc | cta | gaa | aaa | ttt | tcc | act | 338 |
| Asp | Ser | Ser | Ala | Thr | Trp | Glu | Gln | Ser | Leu | Leu | Glu | Lys | Phe | Ser | Thr |   |
| 95 |   |   |   |   | 100 |   |   |   |   | 105 |   |   |   |   | 110 |   |
| gaa | ctt | aac | cag | cag | ctg | aat | gac | atg | gaa | gcc | tgc | gtg | ata | cag | gag | 386 |
| Glu | Leu | Asn | Gln | Gln | Leu | Asn | Asp | Met | Glu | Ala | Cys | Val | Ile | Gln | Glu |   |
|   |   |   |   | 115 |   |   |   |   | 120 |   |   |   |   | 125 |   |   |
| gtt | ggg | gtg | gaa | gag | act | ccc | ctg | atg | aat | gtg | gac | tcc | atc | ttg | gct | 434 |
| Val | Gly | Val | Glu | Glu | Thr | Pro | Leu | Met | Asn | Val | Asp | Ser | Ile | Leu | Ala |   |
|   |   |   | 130 |   |   |   |   | 135 |   |   |   |   | 140 |   |   |   |
| gtg | aag | aaa | tac | ttc | caa | aga | atc | act | ctt | tat | ctg | aca | gag | aag | aaa | 482 |
| Val | Lys | Lys | Tyr | Phe | Gln | Arg | Ile | Thr | Leu | Tyr | Leu | Thr | Glu | Lys | Lys |   |
|   |   | 145 |   |   |   |   | 150 |   |   |   |   | 155 |   |   |   |   |
| tac | agc | cct | tgt | gct | tgg | gag | gtt | gtc | aga | gca | gaa | atc | atg | aga | tcc | 530 |
| Tyr | Ser | Pro | Cys | Ala | Trp | Glu | Val | Val | Arg | Ala | Glu | Ile | Met | Arg | Ser |   |
| 160 |   |   |   |   | 165 |   |   |   |   | 170 |   |   |   |   |   |   |
| ttc | tct | tta | tca | aaa | att | ttt | caa | gaa | aga | tta | agg | agg | aag | gaa |   | 575 |
| Phe | Ser | Leu | Ser | Lys | Ile | Phe | Gln | Glu | Arg | Leu | Arg | Arg | Lys | Glu |   |   |
| 175 |   |   |   | 180 |   |   |   |   | 185 |   |   |   |   |   |   |   | tgaaaccgtt tcaacatgga aatgatctgt attgactaat acaccagtcc acacttctat     635 gacttctgcc atttcaaaga ctcatttctc ctataaccac cgcatgagtt gaatcaaaat     695 tttcagatct tttcaggagt gtaaggaaac atcatgttta cctgtgcagg cactagtcct     755 ttacagatga ccatgctgat agatctaatt atctatctat tgaaatattt atttatttat     815 tagatttaaa ttattttgt ccatgtaata ttatgtgtac ttttacattg tgttatatca      875 aaatatgtta atctaatatt tagtcaatat attattttct ttttattaat ttttactatt    935 aaaacttctt atattatttg gttattcttt aataaagaaa ttccaagccc                985

<210> SEQ ID NO 12
<211> LENGTH: 189
<212> TYPE: PRT
<213> ORGANISM: Homo sapiens

<400> SEQUENCE: 12

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

Pro Phe Ser Cys Leu Lys Asp Arg His Asp Phe Gly Phe Pro Gln Glu
    50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Thr Trp Glu Gln Ser Leu Leu Glu Lys Phe Ser Thr Glu Leu
            100                 105                 110

Asn Gln Gln Leu Asn Asp Met Glu Ala Cys Val Ile Gln Glu Val Gly
        115                 120                 125

Val Glu Glu Thr Pro Leu Met Asn Val Asp Ser Ile Leu Ala Val Lys
    130                 135                 140

```
Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Phe Ser
                165                 170                 175

Leu Ser Lys Ile Phe Gln Glu Arg Leu Arg Arg Lys Glu
            180                 185

<210> SEQ ID NO 13
<211> LENGTH: 760
<212> TYPE: DNA
<213> ORGANISM: Homo sapiens
<220> FEATURE:
<221> NAME/KEY: CDS
<222> LOCATION: (1)...(399)

<400> SEQUENCE: 13 cat gac ttt gga ttt cct cag gag gag ttt gat ggc aac cag ttc cag      48
His Asp Phe Gly Phe Pro Gln Glu Glu Phe Asp Gly Asn Gln Phe Gln
 1               5                  10                  15 aag gct caa gcc atc tct gtc ctc cat gag atg atc cag cag acc ttc      96
Lys Ala Gln Ala Ile Ser Val Leu His Glu Met Ile Gln Gln Thr Phe
             20                  25                  30 aat ctc ttc agc aca aag gac tca tct gct act tgg gat gag aca ctt     144
Asn Leu Phe Ser Thr Lys Asp Ser Ser Ala Thr Trp Asp Glu Thr Leu
         35                  40                  45 cta gac aaa ttc tac act gaa ctt tac cag cag ctg aat gac ctg gaa     192
Leu Asp Lys Phe Tyr Thr Glu Leu Tyr Gln Gln Leu Asn Asp Leu Glu
     50                  55                  60 gcc tgt atg atg cag gag gtt gga gtg gaa gac act cct ctg atg aat     240
Ala Cys Met Met Gln Glu Val Gly Val Glu Asp Thr Pro Leu Met Asn
 65                  70                  75                  80 gtg gac tct atc ctg act gtg aga aaa tac ttt caa aga atc acc ctc     288
Val Asp Ser Ile Leu Thr Val Arg Lys Tyr Phe Gln Arg Ile Thr Leu
                 85                  90                  95 tat ctg aca gag aag aaa tac agc cct tgt gca tgg gag gtt gtc aga     336
Tyr Leu Thr Glu Lys Lys Tyr Ser Pro Cys Ala Trp Glu Val Val Arg
            100                 105                 110 gca gaa atc atg aga tcc ttc tct tta tca gca aac ttg caa gaa aga     384
Ala Glu Ile Met Arg Ser Phe Ser Leu Ser Ala Asn Leu Gln Glu Arg
        115                 120                 125 tta agg agg aag gaa tgaaaactgg ttcaacatcg aaatgattct cattgactag     439
Leu Arg Arg Lys Glu
    130 tacaccattt cacacttctt gagttctgcc gtttcaaata ttaatttctg ctatatccat    499 gacttgagtt gaatcaaaat tttcaaacgt tttcacacgt gttaagcaac acttctttag   559 ctgcacaggg actagtcttt tacagatgat catgctgaca tctattcttc tatttatcgt   619 catcattgtc gttttactac tattaatatt tatattatta ttgtttcatg ttattttttat 679 gtttagtttt agtttgtggt taatataaca aaatatgttt tgtggtcata tattaatttg   739 cttttttatta aattagtttg t                                            760

<210> SEQ ID NO 14
<211> LENGTH: 133
<212> TYPE: PRT
<213> ORGANISM: Homo sapiens

<400> SEQUENCE: 14

His Asp Phe Gly Phe Pro Gln Glu Glu Phe Asp Gly Asn Gln Phe Gln
 1               5                  10                  15
```

-continued

```
Lys Ala Gln Ala Ile Ser Val Leu His Glu Met Ile Gln Gln Thr Phe
         20                  25                  30

Asn Leu Phe Ser Thr Lys Asp Ser Ser Ala Thr Trp Asp Glu Thr Leu
         35                  40                  45

Leu Asp Lys Phe Tyr Thr Glu Leu Tyr Gln Gln Leu Asn Asp Leu Glu
 50                  55                  60

Ala Cys Met Met Gln Glu Val Gly Val Glu Asp Thr Pro Leu Met Asn
 65                  70                  75                  80

Val Asp Ser Ile Leu Thr Val Arg Lys Tyr Phe Gln Arg Ile Thr Leu
                 85                  90                  95

Tyr Leu Thr Glu Lys Lys Tyr Ser Pro Cys Ala Trp Glu Val Val Arg
                 100                 105                 110

Ala Glu Ile Met Arg Ser Phe Ser Leu Ser Ala Asn Leu Gln Glu Arg
             115                 120                 125

Leu Arg Arg Lys Glu
        130
```

<210> SEQ ID NO 15
<211> LENGTH: 985
<212> TYPE: DNA
<213> ORGANISM: Homo sapiens
<220> FEATURE:
<221> NAME/KEY: CDS
<222> LOCATION: (57)...(623)

<400> SEQUENCE: 15

```
ccaaggttca gtgttacccc tcatcaacca gcccagcagc atcttcggga ttccca atg      59
                                                            Met
                                                              1 gca ttg ccc ttt gct tta atg atg gcc cta gtg gtg ctc agc tgc aag      107
Ala Leu Pro Phe Ala Leu Met Met Ala Leu Val Val Leu Ser Cys Lys
          5                  10                  15 tca agc tgc tct ctg ggc tgt aat ctg tct caa acc cac agc ctg aat      155
Ser Ser Cys Ser Leu Gly Cys Asn Leu Ser Gln Thr His Ser Leu Asn
         20                  25                  30 aac agg agg act ttg atg ctc atg gca caa atg agg aga atc tct cct      203
Asn Arg Arg Thr Leu Met Leu Met Ala Gln Met Arg Arg Ile Ser Pro
     35                  40                  45 ttc tcc tgc ctg aag gac aga cat gac ttt gaa ttt ccc cag gag gaa      251
Phe Ser Cys Leu Lys Asp Arg His Asp Phe Glu Phe Pro Gln Glu Glu
 50                  55                  60                  65 ttt gat ggc aac cag ttc cag aaa gct caa gcc atc tct gtc ctc cat      299
Phe Asp Gly Asn Gln Phe Gln Lys Ala Gln Ala Ile Ser Val Leu His
                 70                  75                  80 gag atg atg cag cag acc ttc aat ctc ttc agc aca aag aac tca tct      347
Glu Met Met Gln Gln Thr Phe Asn Leu Phe Ser Thr Lys Asn Ser Ser
             85                  90                  95 gct gct tgg gat gag acc ctc cta gaa aaa ttc tac att gaa ctt ttc      395
Ala Ala Trp Asp Glu Thr Leu Leu Glu Lys Phe Tyr Ile Glu Leu Phe
         100                 105                 110 cag caa atg aat gac ctg gaa gcc tgt gtg ata cag gag gtt ggg gtg      443
Gln Gln Met Asn Asp Leu Glu Ala Cys Val Ile Gln Glu Val Gly Val
     115                 120                 125 gaa gag act ccc ctg atg aat gag gac tcc atc ctg gct gtg aag aaa      491
Glu Glu Thr Pro Leu Met Asn Glu Asp Ser Ile Leu Ala Val Lys Lys
130                 135                 140                 145 tac ttc caa aga atc act ctt tat ctg atg gag aag aaa tac agc cct      539
Tyr Phe Gln Arg Ile Thr Leu Tyr Leu Met Glu Lys Lys Tyr Ser Pro
                 150                 155                 160
```

```
tgt gcc tgg gag gtt gtc aga gca gaa atc atg aga tcc ttc tct ttt      587
Cys Ala Trp Glu Val Val Arg Ala Glu Ile Met Arg Ser Phe Ser Phe
        165                 170                 175 tca aca aac ttg caa aaa aga tta agg agg aag gat tgaaaactgg           633
Ser Thr Asn Leu Gln Lys Arg Leu Arg Arg Lys Asp
        180                 185 ttcatcatgg aaatgattct cattgactaa tacatcatct cacactttca tgttcttcca    693
tttcaaagac tcacttctat aaccaccaca agttgaatca aaatttccaa atgttttcag    753
gagtgttaag aagcatcgtg tttacctgtg caggcactag tcctttacag atgaccattc    813
tgatgtctcc tttcatctat ttatttaaat atttatttat ttaactattt ttattattta    873
aattattttt tatgtaatat catgagtacc tttacattgt ggttaatgta acaaatatgt    933
tcttcatatt tagccaatat attaatttcc tttttcatta aattttttact at           985
```

<210> SEQ ID NO 16
<211> LENGTH: 189
<212> TYPE: PRT
<213> ORGANISM: Homo sapiens

<400> SEQUENCE: 16

```
Met Ala Leu Pro Phe Ala Leu Met Met Ala Leu Val Val Leu Ser Cys
  1               5                  10                  15

Lys Ser Ser Cys Ser Leu Gly Cys Asn Leu Ser Gln Thr His Ser Leu
             20                  25                  30

Asn Asn Arg Arg Thr Leu Met Leu Met Ala Gln Met Arg Arg Ile Ser
         35                  40                  45

Pro Phe Ser Cys Leu Lys Asp Arg His Asp Phe Glu Phe Pro Gln Glu
     50                  55                  60

Glu Phe Asp Gly Asn Gln Phe Gln Lys Ala Gln Ala Ile Ser Val Leu
 65                  70                  75                  80

His Glu Met Met Gln Gln Thr Phe Asn Leu Phe Ser Thr Lys Asn Ser
                 85                  90                  95

Ser Ala Ala Trp Asp Glu Thr Leu Leu Glu Lys Phe Tyr Ile Glu Leu
            100                 105                 110

Phe Gln Gln Met Asn Asp Leu Glu Ala Cys Val Ile Gln Glu Val Gly
        115                 120                 125

Val Glu Glu Thr Pro Leu Met Asn Glu Asp Ser Ile Leu Ala Val Lys
    130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Asn Leu Gln Lys Arg Leu Arg Arg Lys Asp
            180                 185
```

<210> SEQ ID NO 17
<211> LENGTH: 188
<212> TYPE: PRT
<213> ORGANISM: Homo sapiens

<400> SEQUENCE: 17

```
Met Ala Leu Thr Phe Ala Leu Leu Val Ala Leu Leu Val Leu Ser Cys
  1               5                  10                  15

Lys Ser Ser Cys Ser Val Gly Cys Asp Leu Pro Gln Thr His Ser Leu
             20                  25                  30

Gly Ser Arg Arg Thr Leu Met Leu Leu Ala Gln Met Arg Lys Ile Ser
```

```
                35                  40                  45
Leu Phe Ser Cys Leu Lys Asp Arg His Asp Phe Gly Phe Pro Gln Glu
 50                  55                  60

Glu Phe Gly Asn Gln Phe Gln Lys Ala Glu Thr Ile Pro Val Leu His
 65                  70                  75                  80

Glu Met Ile Gln Gln Ile Phe Asn Leu Phe Ser Thr Lys Asp Ser Ser
                 85                  90                  95

Ala Ala Trp Asp Glu Thr Leu Leu Asp Lys Phe Tyr Thr Glu Leu Tyr
                100                 105                 110

Gln Gln Leu Asn Asp Leu Glu Ala Cys Val Ile Gln Gly Val Gly Val
                115                 120                 125

Thr Glu Thr Pro Leu Met Lys Glu Asp Ser Ile Leu Ala Val Arg Lys
130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
                180                 185
```

<210> SEQ ID NO 18
<211> LENGTH: 189
<212> TYPE: PRT
<213> ORGANISM: Homo sapiens

<400> SEQUENCE: 18

```
Met Ala Leu Thr Phe Tyr Leu Met Val Ala Leu Val Val Leu Ser Tyr
  1               5                  10                  15

Lys Ser Phe Ser Ser Leu Gly Cys Asp Leu Pro Gln Thr His Ser Leu
                 20                  25                  30

Gly Asn Arg Arg Ala Leu Ile Leu Leu Ala Gln Met Arg Arg Ile Ser
                 35                  40                  45

Pro Phe Ser Cys Leu Lys Asp Arg His Asp Phe Glu Phe Pro Gln Glu
 50                  55                  60

Glu Phe Asp Asp Lys Gln Phe Gln Lys Ala Gln Ala Ile Ser Val Leu
 65                  70                  75                  80

His Glu Met Ile Gln Gln Thr Phe Asn Leu Phe Ser Thr Lys Asp Ser
                 85                  90                  95

Ser Ala Ala Leu Asp Glu Thr Leu Leu Asp Glu Phe Tyr Ile Glu Leu
                100                 105                 110

Asp Gln Gln Leu Asn Asp Leu Glu Val Leu Cys Asp Gln Glu Val Gly
                115                 120                 125

Val Ile Glu Ser Pro Leu Met Tyr Glu Asp Ser Ile Leu Ala Val Arg
130                 135                 140

Lys Tyr Phe Gln Arg Ile Thr Leu Tyr Leu Thr Glu Lys Lys Tyr Ser
145                 150                 155                 160

Ser Cys Ala Trp Glu Val Val Arg Ala Glu Ile Met Arg Ser Phe Ser
                165                 170                 175

Leu Ser Ile Asn Leu Gln Lys Arg Leu Lys Ser Lys Glu
                180                 185
```

<210> SEQ ID NO 19
<211> LENGTH: 189
<212> TYPE: PRT
<213> ORGANISM: Homo sapiens

```
<400> SEQUENCE: 19

Met Ala Leu Ser Phe Ser Leu Leu Met Ala Val Leu Val Leu Ser Tyr
 1               5                  10                  15

Lys Ser Ile Cys Ser Leu Gly Cys Asp Leu Pro Gln Thr His Ser Leu
             20                  25                  30

Gly Asn Arg Arg Ala Leu Ile Leu Leu Gly Gln Met Gly Arg Ile Ser
         35                  40                  45

Pro Phe Ser Cys Leu Lys Asp Arg His Asp Phe Arg Ile Pro Gln Glu
     50                  55                  60

Glu Phe Asp Gly Asn Gln Phe Gln Lys Ala Gln Ala Ile Ser Val Leu
 65                  70                  75                  80

His Glu Met Ile Gln Gln Thr Phe Asn Leu Phe Ser Thr Glu Asp Ser
                 85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Ile Glu Arg Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
                180                 185

<210> SEQ ID NO 20
<211> LENGTH: 189
<212> TYPE: PRT
<213> ORGANISM: Homo sapiens

<400> SEQUENCE: 20

Met Ala Ser Pro Phe Ala Leu Leu Met Val Leu Val Val Leu Ser Cys
 1               5                  10                  15

Lys Ser Ser Cys Ser Leu Gly Cys Asp Leu Pro Glu Thr His Ser Leu
             20                  25                  30

Asp Asn Arg Arg Thr Leu Met Leu Leu Ala Gln Met Ser Arg Ile Ser
         35                  40                  45

Pro Ser Ser Cys Leu Met Asp Arg His Asp Phe Gly Phe Pro Gln Glu
     50                  55                  60

Glu Phe Asp Gly Asn Gln Phe Gln Lys Ala Pro Ala Ile Ser Val Leu
 65                  70                  75                  80

His Glu Leu Ile Gln Gln Ile Phe Asn Leu Phe Thr Thr Lys Asp Ser
                 85                  90                  95

Ser Ala Ala Trp Asp Glu Asp Leu Leu Asp Lys Phe Cys Thr Glu Leu
            100                 105                 110

Tyr Gln Gln Leu Asn Asp Leu Glu Ala Cys Val Met Gln Glu Glu Arg
        115                 120                 125

Val Gly Glu Thr Pro Leu Met Asn Val Asp Ser Ile Leu Ala Val Lys
    130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175
```

-continued

Leu Ser Thr Asn Leu Gln Glu Arg Leu Arg Arg Lys Glu
                180                 185

<210> SEQ ID NO 21
<211> LENGTH: 105
<212> TYPE: PRT
<213> ORGANISM: Homo sapiens

<400> SEQUENCE: 21

Leu Pro Leu Gly Cys Asp Leu Pro Gln Ala His Ser Val Gly Asn Arg
 1               5                  10                  15

Arg Ala Phe Ile Leu Leu Thr Gln Met Arg Arg Ile Ser Pro Phe Ser
                20                  25                  30

Tyr Leu Lys Asp Arg His Asp Phe Asp Phe Pro His Gln Val Phe His
                35                  40                  45

Gly Asn His Phe Gln Lys Val Gln Ala Ile Phe Leu Phe His Glu Met
            50                  55                  60

Met Gln Gln Thr Phe Asn Leu Phe Ser Thr Lys Asp Ser Ser Asp Thr
65                  70                  75                  80

Trp Asp Glu Thr Leu Leu Asp Lys Ser Tyr Thr Glu Leu Tyr Gln Gln
                85                  90                  95

Leu Asn Asp Leu Glu Ala Cys Val Met
                100                 105

<210> SEQ ID NO 22
<211> LENGTH: 189
<212> TYPE: PRT
<213> ORGANISM: Homo sapiens

<400> SEQUENCE: 22

Met Ala Leu Ser Phe Ser Leu Leu Met Ala Val Leu Val Leu Ser Tyr
 1               5                  10                  15

Lys Ser Ile Cys Ser Leu Gly Cys Asp Leu Pro Gln Thr His Ser Leu
                20                  25                  30

Gly Asn Arg Arg Ala Leu Ile Leu Leu Ala Gln Met Gly Arg Ile Ser
                35                  40                  45

Pro Phe Ser Cys Leu Lys Asp Arg His Asp Phe Gly Phe Pro Gln Glu
            50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Thr Trp Glu Gln Ser Leu Leu Glu Lys Phe Ser Thr Glu Leu
                100                 105                 110

Asn Gln Gln Leu Asn Asp Met Glu Ala Cys Val Ile Gln Glu Val Gly
            115                 120                 125

Val Glu Glu Thr Pro Leu Met Asn Val Asp Ser Ile Leu Ala Val Lys
130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Phe Ser
                165                 170                 175

Leu Ser Lys Ile Phe Gln Glu Arg Leu Arg Arg Lys Glu
                180                 185

<210> SEQ ID NO 23
<211> LENGTH: 133

```
<212> TYPE: PRT
<213> ORGANISM: Homo sapiens

<400> SEQUENCE: 23

His Asp Phe Gly Phe Pro Gln Glu Glu Phe Asp Gly Asn Gln Phe Gln
 1               5                  10                  15

Lys Ala Gln Ala Ile Ser Val Leu His Glu Met Ile Gln Gln Thr Phe
            20                  25                  30

Asn Leu Phe Ser Thr Lys Asp Ser Ser Ala Thr Trp Asp Glu Thr Leu
        35                  40                  45

Leu Asp Lys Phe Tyr Thr Glu Leu Tyr Gln Gln Leu Asn Asp Leu Glu
    50                  55                  60

Ala Cys Met Met Gln Glu Val Gly Val Glu Asp Thr Pro Leu Met Asn
65                  70                  75                  80

Val Asp Ser Ile Leu Thr Val Arg Lys Tyr Phe Gln Arg Ile Thr Leu
                85                  90                  95

Tyr Leu Thr Glu Lys Lys Tyr Ser Pro Cys Ala Trp Glu Val Val Arg
            100                 105                 110

Ala Glu Ile Met Arg Ser Phe Ser Leu Ser Ala Asn Leu Gln Glu Arg
            115                 120                 125

Leu Arg Arg Lys Glu
            130

<210> SEQ ID NO 24
<211> LENGTH: 189
<212> TYPE: PRT
<213> ORGANISM: Homo sapiens

<400> SEQUENCE: 24

Met Ala Leu Pro Phe Ser Leu Met Met Ala Leu Val Val Leu Ser Cys
 1               5                  10                  15

Lys Ser Ser Cys Ser Leu Gly Cys Asn Leu Ser Gln Thr His Ser Leu
            20                  25                  30

Asn Asn Arg Arg Thr Leu Met Leu Met Ala Gln Met Arg Arg Ile Ser
        35                  40                  45

Pro Phe Ser Cys Leu Lys Asp Arg His Asp Phe Glu Phe Pro Gln Glu
    50                  55                  60

Glu Phe Asp Gly Asn Gln Phe Gln Lys Ala Gln Ala Ile Ser Val Leu
65                  70                  75                  80

His Glu Met Met Gln Gln Thr Phe Asn Leu Phe Ser Thr Lys Asn Ser
                85                  90                  95

Ser Ala Ala Trp Asp Glu Thr Leu Leu Glu Lys Phe Tyr Ile Glu Leu
            100                 105                 110

Phe Gln Gln Met Asn Asp Leu Glu Ala Cys Val Ile Gln Glu Val Gly
            115                 120                 125

Val Glu Glu Thr Pro Leu Met Asn Glu Asp Ser Ile Leu Ala Val Arg
            130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Asn Leu Gln Lys Arg Leu Arg Arg Lys Asp
            180                 185

<210> SEQ ID NO 25
<211> LENGTH: 1107
```

```
<212> TYPE: DNA
<213> ORGANISM: Homo sapiens
<220> FEATURE:
<221> NAME/KEY: CDS
<222> LOCATION: (111)...(674)

<400> SEQUENCE: 25
gtatgttccc tatttaaggc taggcacaaa gcaaggtctt cagagaacct ggagcctaag      60
gtttaggctc acccatttca accagtctag cagcatctgc aacatctaca atg gcc       116
                                                          Met Ala
                                                            1 ttg acc ttt gct tta ctg gtg gcc ctc ctg gtg ctc agc tgc aag tca      164
Leu Thr Phe Ala Leu Leu Val Ala Leu Leu Val Leu Ser Cys Lys Ser
         5                  10                  15 agc tgc tct gtg ggc tgt gat ctg cct caa acc cac agc ctg ggt agc      212
Ser Cys Ser Val Gly Cys Asp Leu Pro Gln Thr His Ser Leu Gly Ser
 20                  25                  30 agg agg acc ttg atg ctc ctg gca cag atg agg aga atc tct ctt ttc      260
Arg Arg Thr Leu Met Leu Leu Ala Gln Met Arg Arg Ile Ser Leu Phe
 35                  40                  45                  50 tcc tgc ttg aag gac aga cat gac ttt gga ttt ccc cag gag gag ttt      308
Ser Cys Leu Lys Asp Arg His Asp Phe Gly Phe Pro Gln Glu Glu Phe
             55                  60                  65 ggc aac cag ttc caa aag gct gaa acc atc cct gtc ctc cat gag atg      356
Gly Asn Gln Phe Gln Lys Ala Glu Thr Ile Pro Val Leu His Glu Met
                 70                  75                  80 atc cag cag atc ttc aat ctc ttc agc aca aag gac tca tct gct gct      404
Ile Gln Gln Ile Phe Asn Leu Phe Ser Thr Lys Asp Ser Ser Ala Ala
                     85                  90                  95 tgg gat gag acc ctc cta gac aaa ttc tac act gaa ctc tac cag cag      452
Trp Asp Glu Thr Leu Leu Asp Lys Phe Tyr Thr Glu Leu Tyr Gln Gln
                 100                 105                 110 ctg aat gac ctg gaa gcc tgt gtg ata cag ggg gtg ggg gtg aca gag      500
Leu Asn Asp Leu Glu Ala Cys Val Ile Gln Gly Val Gly Val Thr Glu
115                 120                 125                 130 act ccc ctg atg aag gag gac tcc att ctg gct gtg agg aaa tac ttc      548
Thr Pro Leu Met Lys Glu Asp Ser Ile Leu Ala Val Arg Lys Tyr Phe
                 135                 140                 145 caa aga atc act ctc tat ctg aaa gag aag aaa tac agc cct tgt gcc      596
Gln Arg Ile Thr Leu Tyr Leu Lys Glu Lys Lys Tyr Ser Pro Cys Ala
             150                 155                 160 tgg gag gtt gtc aga gca gaa atc atg aga tct ttt tct ttg tca aca      644
Trp Glu Val Val Arg Ala Glu Ile Met Arg Ser Phe Ser Leu Ser Thr
         165                 170                 175 aac ttg caa gaa agt tta aga agt aag gaa tgaaaactgg ttcaacatgg         694
Asn Leu Gln Glu Ser Leu Arg Ser Lys Glu
     180                 185 aaatgatttt cattgattcg tatgccagct cacctttta tgatctgcca tttcaaagac     754
tcatgtttct gctatgacca tgacacgatt taaatctttt caaatgtttt taggagtatt    814
aatcaacatt gtattcagct cttaaggcac tagtcccta cagaggacca tgctgactga     874
tccattatct atttaaatat ttttaaaata ttatttattt aactatttat aaaacaactt    934
atttttgttc atattatgtc atgtgcacct ttgcacagtg gttaatgtaa taaaatgtgt    994
tctttgtatt tggtaaattt attttgtgtt gttcattgaa cttttgctat ggaacttttg   1054
tacttgttta ttctttaaaa tgaaattcca agcctaattg tgcaacctga tta          1107

<210> SEQ ID NO 26
```

```
<211> LENGTH: 188
<212> TYPE: PRT
<213> ORGANISM: Homo sapiens

<400> SEQUENCE: 26

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 27
<211> LENGTH: 1069
<212> TYPE: DNA
<213> ORGANISM: Homo sapiens
<220> FEATURE:
<221> NAME/KEY: CDS
<222> LOCATION: (111)...(677)

<400> SEQUENCE: 27
gtatgttccc tatttaaggc taggcacaaa gcaaggtctt cagagaacct ggagcctaag      60
gtttaggctc acccatttca accagtctag cagcatctgc aacatctaca atg gca       116
                                                        Met Ala
                                                        1 ttg ccc ttt gct tta atg atg gcc ctg gtg gtg ctc agc tgc aag tca     164
Leu Pro Phe Ala Leu Met Met Ala Leu Val Val Leu Ser Cys Lys Ser
        5                   10                  15 agc tgc tct ctg ggc tgt aat ctg tct caa acc cac agc ctg aat aac     212
Ser Cys Ser Leu Gly Cys Asn Leu Ser Gln Thr His Ser Leu Asn Asn
    20                  25                  30 agg agg act ttg atg ctc atg gca caa atg agg aga atc tct cct ttc     260
Arg Arg Thr Leu Met Leu Met Ala Gln Met Arg Arg Ile Ser Pro Phe
35                  40                  45                  50 tcc tgc ctg aag gac aga cat gac ttt gaa ttt ccc cag gag gaa ttt     308
Ser Cys Leu Lys Asp Arg His Asp Phe Glu Phe Pro Gln Glu Glu Phe
                55                  60                  65 gat ggc aac cag ttc cag aaa gct caa gcc atc tct gtc ctc cat gag     356
Asp Gly Asn Gln Phe Gln Lys Ala Gln Ala Ile Ser Val Leu His Glu
            70                  75                  80
```

```
atg atg cag cag acc ttc aat ctc ttc agc aca aag aac tca tct gct      404
Met Met Gln Gln Thr Phe Asn Leu Phe Ser Thr Lys Asn Ser Ser Ala
         85                  90                  95 gct tgg gat gag acc ctc cta gaa aaa ttc tac att gaa ctt ttc cag      452
Ala Trp Asp Glu Thr Leu Leu Glu Lys Phe Tyr Ile Glu Leu Phe Gln
100                 105                 110 caa atg aat gac ctg gaa gcc tgt gtg ata cag gag gtt ggg gtg gaa      500
Gln Met Asn Asp Leu Glu Ala Cys Val Ile Gln Glu Val Gly Val Glu
115                 120                 125                 130 gag act ccc ctg atg aat gag gac tcc atc ctg gct gtg aag aaa tac      548
Glu Thr Pro Leu Met Asn Glu Asp Ser Ile Leu Ala Val Lys Lys Tyr
                135                 140                 145 ttc caa aga atc act ctt tat ctg atg gag aag aaa tac agc cct tgt      596
Phe Gln Arg Ile Thr Leu Tyr Leu Met Glu Lys Lys Tyr Ser Pro Cys
            150                 155                 160 gcc tgg gag gtt gtc aga gca gaa atc atg aga tcc ctc tct ttt tca      644
Ala Trp Glu Val Val Arg Ala Glu Ile Met Arg Ser Leu Ser Phe Ser
                165                 170                 175 aca aac ttg caa aaa aga tta agg agg aag gat tgaaaagtgg ttcatcatgg    697
Thr Asn Leu Gln Lys Arg Leu Arg Arg Lys Asp
180                 185 aaatgattct cattgactaa tacatcatct cacactttca tgagttcttc catttcaaag    757
actcacttct cctataacca ccacaagttg aatcaaaatt ttcaaatgtt ttcaggagtg    817
taaagaagca tcatgtatac ctgtgcaggc actagtcctt tacagatgac catgctgatg    877
tctcctttca tctatttatt taaatattta tttatttaac tattttatt atttaaatta     937 tttttatgt taatatcatg tgtacctta cattgtggtt aatataacaa atatgttctt      997
catatttagc caatatatta atttccttt tcattaaatt tttactatac aaaatttctg    1057
tgtttggtat tt                                                       1069

<210> SEQ ID NO 28
<211> LENGTH: 189
<212> TYPE: PRT
<213> ORGANISM: Homo sapiens

<400> SEQUENCE: 28

Met Ala Leu Pro Phe Ala Leu Met Met Ala Leu Val Val Leu Ser Cys
1               5                   10                  15

Lys Ser Ser Cys Ser Leu Gly Cys Asn Leu Ser Gln Thr His Ser Leu
            20                  25                  30

Asn Asn Arg Arg Thr Leu Met Leu Met Ala Gln Met Arg Arg Ile Ser
        35                  40                  45

Pro Phe Ser Cys Leu Lys Asp Arg His Asp Phe Glu Phe Pro Gln Glu
    50                  55                  60

Glu Phe Asp Gly Asn Gln Phe Gln Lys Ala Gln Ala Ile Ser Val Leu
65                  70                  75                  80

His Glu Met Met Gln Gln Thr Phe Asn Leu Phe Ser Thr Lys Asn Ser
                85                  90                  95

Ser Ala Ala Trp Asp Glu Thr Leu Leu Glu Lys Phe Tyr Ile Glu Leu
            100                 105                 110

Phe Gln Gln Met Asn Asp Leu Glu Ala Cys Val Ile Gln Glu Val Gly
        115                 120                 125

Val Glu Glu Thr Pro Leu Met Asn Glu Asp Ser Ile Leu Ala Val Lys
    130                 135                 140

Lys Tyr Phe Gln Arg Ile Thr Leu Tyr Leu Met Glu Lys Lys Tyr Ser
145                 150                 155                 160
```

```
            Pro Cys Ala Trp Glu Val Val Arg Ala Glu Ile Met Arg Ser Leu Ser
                            165                 170                 175

Phe Ser Thr Asn Leu Gln Lys Arg Leu Arg Arg Lys Asp
                            180                 185

<210> SEQ ID NO 29
<211> LENGTH: 1112
<212> TYPE: DNA
<213> ORGANISM: Homo sapiens
<220> FEATURE:
<221> NAME/KEY: CDS
<222> LOCATION: (113)...(679)

<400> SEQUENCE: 29
gtatgttcct tatttaagac ctatgcacag agcaaggtct tcagaaaacc tacaacccaa          60
ggttcagtgt taccctcat caaccagccc agcagcatct tcagggttcc ca atg gcc         118
                                                            Met Ala
                                                              1 ctg tcc ttt tct tta ctg atg gcc gtg ctg gtg ctc agc tac aaa tcc         166
Leu Ser Phe Ser Leu Leu Met Ala Val Leu Val Leu Ser Tyr Lys Ser
        5                   10                  15 atc tgt tct cta ggc tgt gat ctg cct cag acc cac agc ctg ggt aat         214
Ile Cys Ser Leu Gly Cys Asp Leu Pro Gln Thr His Ser Leu Gly Asn
 20                  25                  30 agg agg gcc ttg ata ctc ctg gca caa atg gga aga atc tct cct ttc         262
Arg Arg Ala Leu Ile Leu Leu Ala Gln Met Gly Arg Ile Ser Pro Phe
 35                  40                  45                  50 tcc tgc ctg aag gac aga cct gac ttt gga ctt ccc cag gag gag ttt         310
Ser Cys Leu Lys Asp Arg Pro Asp Phe Gly Leu Pro Gln Glu Glu Phe
                 55                  60                  65 gat ggc aac cag ttc cag aag act caa gcc atc tct gtc ctc cat gag         358
Asp Gly Asn Gln Phe Gln Lys Thr Gln Ala Ile Ser Val Leu His Glu
             70                  75                  80 atg atc cag cag acc ttc aat ctc ttc agc aca gag gac tca tct gct         406
Met Ile Gln Gln Thr Phe Asn Leu Phe Ser Thr Glu Asp Ser Ser Ala
         85                  90                  95 gct tgg gaa cag agc ctc cta gaa aaa ttt tcc act gaa ctt tac cag         454
Ala Trp Glu Gln Ser Leu Leu Glu Lys Phe Ser Thr Glu Leu Tyr Gln
100                 105                 110 caa ctg aat aac ctg gaa gca tgt gtg ata cag gag gtt ggg atg gaa         502
Gln Leu Asn Asn Leu Glu Ala Cys Val Ile Gln Glu Val Gly Met Glu
115                 120                 125                 130 gag act ccc ctg atg aat gag gac tcc atc ctg gct gtg agg aaa tac         550
Glu Thr Pro Leu Met Asn Glu Asp Ser Ile Leu Ala Val Arg Lys Tyr
                135                 140                 145 ttc caa aga atc act ctt tat cta aca gag aag aaa tac agc cct tca         598
Phe Gln Arg Ile Thr Leu Tyr Leu Thr Glu Lys Lys Tyr Ser Pro Ser
            150                 155                 160 gcc tgg gag gtt gtc aga gca gaa atc atg aga tct ctc tct ttt tca         646
Ala Trp Glu Val Val Arg Ala Glu Ile Met Arg Ser Leu Ser Phe Ser
        165                 170                 175 aca aac ttg caa aaa ata tta agg agg aag gat tgaaaactgg ttcaacatgg        699
Thr Asn Leu Gln Lys Ile Leu Arg Arg Lys Asp
180                 185 caatgatcct gattgactaa tacattatct cacactttca tgagttcctc catttcaaag        759
actcacttct ataaccacca cgagttgaat caaaattttc aaatgttttc agcagtgtaa        819
agaagcgtcg tgtatacctg tgcaggcact agtacttac agatgaccat gctgatgtct         879
ctgttcatct atttatttaa atatttattt aattattttt aagatttaaa ttattttttt        939
```

```
atgtaatatc atgtgtacct ttacattgtg gtgaatgtaa caatatatgt tcttcatatt      999
tagccaatat attaatttcc tttttcatta aatttttact atacaaaatt tcttgagttt     1059
gtttattctt aagaataaaa tgtcgaggct gactttacaa cctgacttaa aaa            1112
```

<210> SEQ ID NO 30
<211> LENGTH: 189
<212> TYPE: PRT
<213> ORGANISM: Homo sapiens

<400> SEQUENCE: 30

```
Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

Pro Phe Ser Cys Leu Lys Asp Arg Pro Asp Phe Gly Leu Pro Gln Glu
    50                  55                  60

Glu Phe Asp Gly Asn Gln Phe Gln Lys Thr Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asn Leu Glu Ala Cys Val Ile Gln Glu Val Gly
        115                 120                 125

Met Glu Glu Thr Pro Leu Met Asn Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Pro Ser Ala Trp Glu Val Val Arg Ala Glu Ile Met Arg Ser Leu Ser
                165                 170                 175

Phe Ser Thr Asn Leu Gln Lys Ile Leu Arg Arg Lys Asp
            180                 185
```

<210> SEQ ID NO 31
<211> LENGTH: 1109
<212> TYPE: DNA
<213> ORGANISM: Homo sapiens
<220> FEATURE:
<221> NAME/KEY: CDS
<222> LOCATION: (111)...(677)

<400> SEQUENCE: 31

```
gtatgttcac tatttaaggc ctatgcacag agcaaagtct tcagaaaacc tagaggccaa       60
agttcaaggt tacccatctc aagtagccta gcaacatttg caacatccca atg gcc        116
                                                       Met Ala
                                                         1 cgg tcc ttt tct tta ctg atg gtc gtg ctg gta ctc agc tac aaa tcc       164
Arg Ser Phe Ser Leu Leu Met Val Val Leu Val Leu Ser Tyr Lys Ser
        5                   10                  15 atc tgc tct ctg ggc tgt gat ctg cct cag acc cac agc ctg cgt aat       212
Ile Cys Ser Leu Gly Cys Asp Leu Pro Gln Thr His Ser Leu Arg Asn
    20                  25                  30 agg agg gcc ttg ata ctc ctg gca caa atg gga aga atc tct cct ttc       260
Arg Arg Ala Leu Ile Leu Leu Ala Gln Met Gly Arg Ile Ser Pro Phe
35                  40                  45                  50
```

```
tcc tgc ttg aag gac aga cat gaa ttc aga ttc cca gag gag gag ttt      308
Ser Cys Leu Lys Asp Arg His Glu Phe Arg Phe Pro Glu Glu Glu Phe
             55                  60                  65 gat ggc cac cag ttc cag aag act caa gcc atc tct gtc ctc cat gag      356
Asp Gly His Gln Phe Gln Lys Thr Gln Ala Ile Ser Val Leu His Glu
         70                  75                  80 atg atc cag cag acc ttc aat ctc ttc agc aca gag gac tca tct gct      404
Met Ile Gln Gln Thr Phe Asn Leu Phe Ser Thr Glu Asp Ser Ser Ala
         85                  90                  95 gct tgg gaa cag agc ctc cta gaa aaa ttt tcc act gaa ctt tac cag      452
Ala Trp Glu Gln Ser Leu Leu Glu Lys Phe Ser Thr Glu Leu Tyr Gln
        100                 105                 110 caa ctg aat gac ctg gaa gca tgt gtg ata cag gag gtt ggg gtg aa       500
Gln Leu Asn Asp Leu Glu Ala Cys Val Ile Gln Glu Val Gly Val Glu
115                 120                 125                 130 gag act ccc ctg atg aat gag gac ttc atc ctg gct gtg agg aaa tac      548
Glu Thr Pro Leu Met Asn Glu Asp Phe Ile Leu Ala Val Arg Lys Tyr
                135                 140                 145 ttc caa aga atc act ctt tat cta atg gag aag aaa tac agc cct tgt      596
Phe Gln Arg Ile Thr Leu Tyr Leu Met Glu Lys Lys Tyr Ser Pro Cys
            150                 155                 160 gcc tgg gag gtt gtc aga gca gaa atc atg aga tcc ttc tct ttt tca      644
Ala Trp Glu Val Val Arg Ala Glu Ile Met Arg Ser Phe Ser Phe Ser
        165                 170                 175 aca aac ttg aaa aaa gga tta agg agg aag gat tgaaaactgg ttcatcatgg    697
Thr Asn Leu Lys Lys Gly Leu Arg Arg Lys Asp
        180                 185 aaatgattct cattgactaa tgcatcatct cacactttca tgagttcttc catttcaaag    757
actcacttct ataaccacca caagttgaat caaaatttcc aaatgttttc aggagtgtta    817
agaagcatcg tgtttacctg tgcaggcact agtcctttac agatgaccat tctgatgtct    877
cctttcatct atttatttaa atatttattt atttaactat ttttattatt taaattattt    937
tttatgtaat atcatatgta cctttacatt gtggttaatg taacaaatat gttcttcata    997
tttagccaat atattaattt cctttttcat taaattttta ctatacaaaa tttcttgtgt    1057
ttgtttattt tttaagatta aatgccaagc ctgactgtat aacctgactt aa            1109
```

<210> SEQ ID NO 32
<211> LENGTH: 189
<212> TYPE: PRT
<213> ORGANISM: Homo sapiens

<400> SEQUENCE: 32

```
Met Ala Arg Ser Phe Ser Leu Leu Met Val Val Leu Val Leu Ser Tyr
1               5                   10                  15

Lys Ser Ile Cys Ser Leu Gly Cys Asp Leu Pro Gln Thr His Ser Leu
            20                  25                  30

Arg Asn Arg Arg Ala Leu Ile Leu Leu Ala Gln Met Gly Arg Ile Ser
        35                  40                  45

Pro Phe Ser Cys Leu Lys Asp Arg His Glu Phe Arg Phe Pro Glu Glu
    50                  55                  60

Glu Phe Asp Gly His Gln Phe Gln Lys Thr Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110
```

```
        Tyr Gln Gln Leu Asn Asp Leu Glu Ala Cys Val Ile Gln Glu Val Gly
                    115                 120                 125

Val Glu Glu Thr Pro Leu Met Asn Glu Asp Phe Ile Leu Ala Val Arg
            130                 135                 140

Lys Tyr Phe Gln Arg Ile Thr Leu Tyr Leu Met Glu Lys Lys Tyr Ser
        145                 150                 155                 160

Pro Cys Ala Trp Glu Val Val Arg Ala Glu Ile Met Arg Ser Phe Ser
                        165                 170                 175

Phe Ser Thr Asn Leu Lys Lys Gly Leu Arg Arg Lys Asp
                    180                 185

<210> SEQ ID NO 33
<211> LENGTH: 1109
<212> TYPE: DNA
<213> ORGANISM: Homo sapiens
<220> FEATURE:
<221> NAME/KEY: CDS
<222> LOCATION: (110)...(676)

<400> SEQUENCE: 33
gtatgttcac tatttaagac ctatgcacag agcaaagtct tcagaaaacc tagaggccac     60
ggttcaagtt acccacctca ggtagcctag tgatatttgc aaaatcccca atg gcc ctg   118
                                                      Met Ala Leu
                                                        1 tcc ttt tct tta ctt atg gcc gtg ctg gtg ctc agc tac aaa tcc atc     166
Ser Phe Ser Leu Leu Met Ala Val Leu Val Leu Ser Tyr Lys Ser Ile
        5                  10                  15 tga tct ctg ggc tgt gat ctg cct cag acc cac acc ctg cgt aat agg     214
 *  Ser Leu Gly Cys Asp Leu Pro Gln Thr His Thr Leu Arg Asn Arg
    20                  25                  30 agg gcc ttg ata ctc ctg gga caa atg gga aga atc tct cct ttc tcc     262
Arg Ala Leu Ile Leu Leu Gly Gln Met Gly Arg Ile Ser Pro Phe Ser
 35                  40                  45                  50 tgc ctg aag gac aga cat gat ttc cga atc ccc cag gag gag ttt gat     310
Cys Leu Lys Asp Arg His Asp Phe Arg Ile Pro Gln Glu Glu Phe Asp
                 55                  60                  65 ggc aac cag ttc cag aag gct caa gcc atc tct gtc ctc cat gag atg     358
Gly Asn Gln Phe Gln Lys Ala Gln Ala Ile Ser Val Leu His Glu Met
             70                  75                  80 atc cag cag acc ttc aat ctc ttc agc aca gag gac tca tct gct gct     406
Ile Gln Gln Thr Phe Asn Leu Phe Ser Thr Glu Asp Ser Ser Ala Ala
         85                  90                  95 tgg gaa cag agc ctc cta gaa aaa ttt tcc act gaa att tac cag caa     454
Trp Glu Gln Ser Leu Leu Glu Lys Phe Ser Thr Glu Ile Tyr Gln Gln
100                 105                 110 ctg aat gac ctg gaa gca tgt gtg ata cag gag gtt ggg gtg gaa gag     502
Leu Asn Asp Leu Glu Ala Cys Val Ile Gln Glu Val Gly Val Glu Glu
115                 120                 125                 130 act ccc ctg atg aat gag gac tcc atc ctg gct gtg agg aaa tac ttc     550
Thr Pro Leu Met Asn Glu Asp Ser Ile Leu Ala Val Arg Lys Tyr Phe
                135                 140                 145 caa aga atc act ctt tat cta ata gag agg aaa tac agc cct tgt gcc     598
Gln Arg Ile Thr Leu Tyr Leu Ile Glu Arg Lys Tyr Ser Pro Cys Ala
            150                 155                 160 tgg gag gtt gtc aga gca gaa atc atg aga tcc ctc tcg ttt tca aca     646
Trp Glu Val Val Arg Ala Glu Ile Met Arg Ser Leu Ser Phe Ser Thr
        165                 170                 175 aac ttg caa aaa aga tta agg agg aag gat tgaaaactgg ttcaacatgg       696
Asn Leu Gln Lys Arg Leu Arg Arg Lys Asp
    180                 185
```

```
caatgatcct gattgactaa tacattatct cacactttca tgagttcttc catttcaaag      756
actcacttct ataaccacga cgtgttgaat caaaattttc aaatgttttc agcagtgtaa      816
agaagtgtcg tgtatacctg tgcaggcact agtcctttac agatgaccat tctgatgtct      876
ctgttcatct tttgtttaaa tatttattta attattttta aaatttatgt aatatcatga      936
gtcgctttac attgtggtta atgtaacaat atatgttctt catatttagc caatatatta      996 atttccttt tcattaaatt tttactatac aaaatttctt gtgtttgttt attctttaag     1056
ataaaatgcc aaggctgact ttacaacctg acttaaaaat agatgattta att            1109
```

<210> SEQ ID NO 34
<211> LENGTH: 169
<212> TYPE: PRT
<213> ORGANISM: Homo sapiens

<400> SEQUENCE: 34

```
Ser Leu Gly Cys Asp Leu Pro Gln Thr His Thr Leu Arg Asn Arg Arg
 1               5                  10                  15

Ala Leu Ile Leu Leu Gly Gln Met Gly Arg Ile Ser Pro Phe Ser Cys
                20                  25                  30

Leu Lys Asp Arg His Asp Phe Arg Ile Pro Gln Glu Glu Phe Asp Gly
            35                  40                  45

Asn Gln Phe Gln Lys Ala Gln Ala Ile Ser Val Leu His Glu Met Ile
 50                  55                  60

Gln Gln Thr Phe Asn Leu Phe Ser Thr Glu Asp Ser Ser Ala Ala Trp
 65                  70                  75                  80

Glu Gln Ser Leu Leu Glu Lys Phe Ser Thr Glu Ile Tyr Gln Gln Leu
                85                  90                  95

Asn Asp Leu Glu Ala Cys Val Ile Gln Glu Val Gly Val Glu Glu Thr
            100                 105                 110

Pro Leu Met Asn Glu Asp Ser Ile Leu Ala Val Arg Lys Tyr Phe Gln
        115                 120                 125

Arg Ile Thr Leu Tyr Leu Ile Glu Arg Lys Tyr Ser Pro Cys Ala Trp
    130                 135                 140

Glu Val Val Arg Ala Glu Ile Met Arg Ser Leu Ser Phe Ser Thr Asn
145                 150                 155                 160

Leu Gln Lys Arg Leu Arg Arg Lys Asp
                165
```

<210> SEQ ID NO 35
<211> LENGTH: 188
<212> TYPE: PRT
<213> ORGANISM: Homo sapiens

<400> SEQUENCE: 35

```
Met Ala Leu Thr Phe Ala Leu Leu Val Ala Leu Leu Val Leu Ser Cys
 1               5                  10                  15

Lys Ser Ser Cys Ser Val Gly Cys Asp Leu Pro Gln Thr His Ser Leu
                20                  25                  30

Gly Ser Arg Arg Thr Leu Met Leu Leu Ala Gln Met Arg Arg Ile Ser
            35                  40                  45

Leu Phe Ser Cys Leu Lys Asp Arg His Asp Phe Gly Phe Pro Gln Glu
 50                  55                  60

Glu Phe Gly Asn Gln Phe Gln Lys Ala Glu Thr Ile Pro Val Leu His
 65                  70                  75                  80
```

```
Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
            165                 170                 175

Ser Thr Asn Leu Gln Glu Ser Leu Arg Ser Lys Glu
            180                 185

<210> SEQ ID NO 36
<211> LENGTH: 189
<212> TYPE: PRT
<213> ORGANISM: Homo sapiens

<400> SEQUENCE: 36

Met Ala Leu Pro Phe Ser Leu Met Met Ala Leu Val Val Leu Ser Cys
1               5                   10                  15

Lys Ser Ser Cys Ser Leu Gly Cys Asn Leu Ser Gln Thr His Ser Leu
            20                  25                  30

Asn Asn Arg Arg Thr Leu Met Leu Met Ala Gln Met Arg Arg Ile Ser
        35                  40                  45

Pro Phe Ser Cys Leu Lys Asp Arg His Asp Phe Glu Phe Pro Gln Glu
    50                  55                  60

Glu Phe Asp Gly Asn Gln Phe Gln Lys Ala Gln Ala Ile Ser Val Leu
65                  70                  75                  80

His Glu Met Met Gln Gln Thr Phe Asn Leu Phe Ser Thr Lys Asn Ser
                85                  90                  95

Ser Ala Ala Trp Asp Glu Thr Leu Leu Glu Lys Phe Tyr Ile Glu Leu
            100                 105                 110

Phe Gln Gln Met Asn Asp Leu Glu Ala Cys Val Ile Glu Val Gly
        115                 120                 125

Val Glu Glu Thr Pro Leu Met Asn Glu Asp Ser Ile Leu Ala Val Arg
        130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Leu Ser
            165                 170                 175

Phe Ser Thr Asn Leu Gln Lys Arg Leu Arg Arg Lys Asp
            180                 185

<210> SEQ ID NO 37
<211> LENGTH: 189
<212> TYPE: PRT
<213> ORGANISM: Homo sapiens

<400> SEQUENCE: 37

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30
```

Gly Asn Arg Arg Ala Leu Ile Leu Leu Ala Gln Met Gly Arg Ile Ser
                35                  40                  45

Pro Phe Ser Cys Leu Lys Asp Arg Pro Asp Phe Gly Leu Pro Gln Glu
         50                  55                  60

Glu Phe Asp Gly Asn Gln Phe Gln Lys Thr Gln Ala Ile Ser Val Leu
65                  70                  75                  80

His Glu Met Ile Gln Gln Thr Phe Asn Leu Phe Ser Thr Glu Asp Ser
                 85                  90                  95

Ser Ala Ala Trp Glu Gln Ser Leu Leu Glu Lys Phe Ser Thr Glu Leu
            100                 105                 110

Tyr Gln Gln Leu Asn Asn Leu Glu Ala Cys Val Ile Gln Glu Val Gly
            115                 120                 125

Met Glu Glu Thr Pro Leu Met Asn Glu Asp Ser Ile Leu Ala Val Arg
        130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Ile Leu Arg Arg Lys Asp
            180                 185

<210> SEQ ID NO 38
<211> LENGTH: 169
<212> TYPE: PRT
<213> ORGANISM: Homo sapiens

<400> SEQUENCE: 38

Ser Leu Gly Cys Asp Leu Pro Gln Thr His Ser Leu Gly Asn Arg Arg
1               5                   10                  15

Ala Leu Ile Leu Leu Gly Gln Met Gly Arg Ile Ser Pro Phe Ser Cys
            20                  25                  30

Leu Lys Asp Arg His Asp Phe Arg Ile Pro Gln Glu Glu Phe Asp Gly
        35                  40                  45

Asn Gln Phe Gln Lys Ala Gln Ala Ile Ser Val Leu His Glu Met Ile
 50                 55                  60

Gln Gln Thr Phe Asn Leu Phe Ser Thr Glu Asp Ser Ser Ala Ala Trp
65                  70                  75                  80

Glu Gln Ser Leu Leu Glu Lys Phe Ser Thr Glu Ile Tyr Gln Gln Leu
                85                  90                  95

Asn Asp Leu Glu Ala Cys Val Ile Gln Glu Val Gly Val Glu Glu Thr
            100                 105                 110

Pro Leu Met Asn Glu Asp Ser Ile Leu Ala Val Arg Lys Tyr Phe Gln
        115                 120                 125

Arg Ile Thr Leu Tyr Leu Ile Glu Arg Lys Tyr Ser Pro Cys Ala Trp
    130                 135                 140

Glu Val Val Arg Ala Glu Ile Met Arg Ser Leu Ser Phe Ser Thr Asn
145                 150                 155                 160

Leu Gln Lys Arg Leu Arg Arg Lys Asp
                165

<210> SEQ ID NO 39
<211> LENGTH: 12
<212> TYPE: DNA
<213> ORGANISM: Artificial Sequence
<220> FEATURE:
<223> OTHER INFORMATION: Eco RI linker

```
<400> SEQUENCE: 39
catgaattca tg                                                    12

<210> SEQ ID NO 40
<211> LENGTH: 14
<212> TYPE: DNA
<213> ORGANISM: Unknown
<220> FEATURE:
<223> OTHER INFORMATION: XbaI and EcoRI cleavage sites

<400> SEQUENCE: 40
tctagaattc tatg                                                  14

<210> SEQ ID NO 41
<211> LENGTH: 14
<212> TYPE: DNA
<213> ORGANISM: Unknown
<220> FEATURE:
<223> OTHER INFORMATION: XbaI and EcoRI cleavage sites

<400> SEQUENCE: 41
catagaattc taga                                                  14

<210> SEQ ID NO 42
<211> LENGTH: 11
<212> TYPE: DNA
<213> ORGANISM: Artificial Sequence
<220> FEATURE:
<223> OTHER INFORMATION: Synthetic deoxyoligonucleotides

<400> SEQUENCE: 42
aattcatgtg t                                                     11

<210> SEQ ID NO 43
<211> LENGTH: 11
<212> TYPE: DNA
<213> ORGANISM: Artificial Sequence
<220> FEATURE:
<223> OTHER INFORMATION: Synthetic deoxyoligonucleotides

<400> SEQUENCE: 43
gatcacacat g                                                     11

<210> SEQ ID NO 44
<211> LENGTH: 10
<212> TYPE: DNA
<213> ORGANISM: Artificial Sequence
<220> FEATURE:
<223> OTHER INFORMATION: EcoRI to PstI convertor

<400> SEQUENCE: 44
aattctgcag                                                       10

<210> SEQ ID NO 45
<211> LENGTH: 166
<212> TYPE: PRT
<213> ORGANISM: Homo sapiens

<400> SEQUENCE: 45

Met Cys Asp Leu Pro Gln Thr His Ser Leu Gly Ser Arg Arg Thr Leu
 1               5                  10                  15

Met Leu Leu Ala Gln Met Arg Lys Ile Ser Leu Phe Ser Cys Leu Lys
            20                  25                  30
```

-continued

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
            115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 46
<211> LENGTH: 167
<212> TYPE: PRT
<213> ORGANISM: Homo sapiens

<400> SEQUENCE: 46

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Glu Phe Pro Gln Glu Glu Phe Asp Asp Lys Gln
        35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Ala Leu Asp Glu
65                  70                  75                  80

Thr Leu Leu Asp Glu Phe Tyr Ile Glu Leu Asp Gln Gln Leu Asn Asp
                85                  90                  95

Leu Glu Val Leu Cys Asp Gln Glu Val Gly Val Ile Glu Ser Pro Leu
            100                 105                 110

Met Tyr Glu Asp Ser Ile Leu Ala Val Arg Lys Tyr Phe Gln Arg Ile
            115                 120                 125

Thr Leu Tyr Leu Thr Glu Lys Lys Tyr Ser Ser Cys Ala Trp Glu Val
    130                 135                 140

Val Arg Ala Glu Ile Met Arg Ser Phe Ser Leu Ser Ile Asn Leu Gln
145                 150                 155                 160

Lys Arg Leu Lys Ser Lys Glu
                165

<210> SEQ ID NO 47
<211> LENGTH: 167
<212> TYPE: PRT
<213> ORGANISM: Homo sapiens

<400> SEQUENCE: 47

Met Cys Asp Leu Pro Gln Thr His Ser Leu Gly Asn Arg Arg Ala Leu
1               5                   10                  15

```
Ile Leu Leu Gly Gln Met Gly Arg Ile Ser Pro Phe Ser Cys Leu Lys
            20                  25                  30

Asp Arg His Asp Phe Arg Ile Pro Gln Glu Glu Phe Asp Gly Asn Gln
            35                  40                  45

Phe Gln Lys Ala Gln Ala Ile Ser Val Leu His Glu Met Ile Gln Gln
 50                  55                  60

Thr Phe Asn Leu Phe Ser Thr Glu Asp Ser Ser Ala Ala Trp Glu Gln
 65                  70                  75                  80

Ser Leu Leu Glu Lys Phe Ser Thr Glu Leu Tyr Gln Gln Leu Asn Asp
                85                  90                  95

Leu Glu Ala Cys Val Ile Gln Glu Val Gly Val Glu Glu Thr Pro Leu
                100                 105                 110

Met Asn Glu Asp Ser Ile Leu Ala Val Arg Lys Tyr Phe Gln Arg Ile
                115                 120                 125

Thr Leu Tyr Leu Ile Glu Arg Lys Tyr Ser Pro Cys Ala Trp Glu Val
            130                 135                 140

Val Arg Ala Glu Ile Met Arg Ser Leu Ser Phe Ser Thr Asn Leu Gln
145                 150                 155                 160

Lys Arg Leu Arg Arg Lys Asp
                165

<210> SEQ ID NO 48
<211> LENGTH: 167
<212> TYPE: PRT
<213> ORGANISM: Homo sapiens

<400> SEQUENCE: 48

Met Cys Asp Leu Pro Glu Thr His Ser Leu Asp Asn Arg Arg Thr Leu
  1               5                  10                  15

Met Leu Leu Ala Gln Met Ser Arg Ile Ser Pro Ser Ser Cys Leu Met
            20                  25                  30

Asp Arg His Asp Phe Gly Phe Pro Gln Glu Glu Phe Asp Gly Asn Gln
            35                  40                  45

Phe Gln Lys Ala Pro Ala Ile Ser Val Leu His Glu Leu Ile Gln Gln
 50                  55                  60

Ile Phe Asn Leu Phe Thr Thr Lys Asp Ser Ser Ala Ala Trp Asp Glu
 65                  70                  75                  80

Asp Leu Leu Asp Lys Phe Cys Thr Glu Leu Tyr Gln Gln Leu Asn Asp
                85                  90                  95

Leu Glu Ala Cys Val Met Gln Glu Glu Arg Val Gly Glu Thr Pro Leu
                100                 105                 110

Met Asn Val Asp Ser Ile Leu Ala Val Lys Lys Tyr Phe Arg Arg Ile
                115                 120                 125

Thr Leu Tyr Leu Thr Glu Lys Lys Tyr Ser Pro Cys Ala Trp Glu Val
            130                 135                 140

Val Arg Ala Glu Ile Met Arg Ser Leu Ser Leu Ser Thr Asn Leu Gln
145                 150                 155                 160

Glu Arg Leu Arg Arg Lys Glu
                165

<210> SEQ ID NO 49
<211> LENGTH: 167
<212> TYPE: PRT
<213> ORGANISM: Homo sapiens

<400> SEQUENCE: 49
```

-continued

```
Met Cys Asp Leu Pro Gln Thr His Ser Leu Gly Asn Arg Arg Ala Leu
 1               5                  10                  15

Ile Leu Leu Ala Gln Met Gly Arg Ile Ser Pro Phe Ser Cys Leu Lys
            20                  25                  30

Asp Arg His Asp Phe Gly Phe Pro Gln Glu Glu Phe Asp Gly Asn Gln
            35                  40                  45

Phe Gln Lys Ala Gln Ala Ile Ser Val Leu His Glu Met Ile Gln Gln
 50                  55                  60

Thr Phe Asn Leu Phe Ser Thr Lys Asp Ser Ser Ala Thr Trp Glu Gln
65                   70                  75                  80

Ser Leu Leu Glu Lys Phe Ser Thr Glu Leu Asn Gln Gln Leu Asn Asp
                85                  90                  95

Met Glu Ala Cys Val Ile Gln Glu Val Gly Val Glu Glu Thr Pro Leu
            100                 105                 110

Met Asn Val Asp Ser Ile Leu Ala Val Lys Lys Tyr Phe Gln Arg Ile
            115                 120                 125

Thr Leu Tyr Leu Thr Glu Lys Lys Tyr Ser Pro Cys Ala Trp Glu Val
            130                 135                 140

Val Arg Ala Glu Ile Met Arg Ser Phe Ser Leu Ser Lys Ile Phe Gln
145                 150                 155                 160

Glu Arg Leu Arg Arg Lys Glu
                165
```

<210> SEQ ID NO 50
<211> LENGTH: 167
<212> TYPE: PRT
<213> ORGANISM: Homo sapiens

<400> SEQUENCE: 50

```
Met Cys Asn Leu Ser Gln Thr His Ser Leu Asn Asn Arg Arg Thr Leu
 1               5                  10                  15

Met Leu Met Ala Gln Met Arg Arg Ile Ser Pro Phe Ser Cys Leu Lys
            20                  25                  30

Asp Arg His Asp Phe Glu Phe Pro Gln Glu Glu Phe Asp Gly Asn Gln
            35                  40                  45

Phe Gln Lys Ala Gln Ala Ile Ser Val Leu His Glu Met Met Gln Gln
 50                  55                  60

Thr Phe Asn Leu Phe Ser Thr Lys Asn Ser Ser Ala Ala Trp Asp Glu
65                   70                  75                  80

Thr Leu Leu Glu Lys Phe Tyr Ile Glu Leu Phe Gln Gln Met Asn Asp
                85                  90                  95

Leu Glu Ala Cys Val Ile Gln Glu Val Gly Val Glu Glu Thr Pro Leu
            100                 105                 110

Met Asn Glu Asp Ser Ile Leu Ala Val Arg Lys Tyr Phe Gln Arg Ile
            115                 120                 125

Thr Leu Tyr Leu Met Glu Lys Lys Tyr Ser Pro Cys Ala Trp Glu Val
            130                 135                 140

Val Arg Ala Glu Ile Met Arg Ser Phe Ser Phe Ser Thr Asn Leu Gln
145                 150                 155                 160

Lys Arg Leu Arg Arg Lys Asp
                165
```

<210> SEQ ID NO 51
<211> LENGTH: 167
<212> TYPE: PRT
<213> ORGANISM: Homo sapiens

<400> SEQUENCE: 51

Met Cys Asp Leu Pro Gln Thr His Ser Leu Gly Asn Arg Arg Ala Leu
1               5                   10                  15

Ile Leu Leu Ala Gln Met Gly Arg Ile Ser Pro Phe Ser Cys Leu Lys
            20                  25                  30

Asp Arg Pro Asp Phe Gly Leu Pro Gln Glu Glu Phe Asp Gly Asn Gln
        35                  40                  45

Phe Gln Lys Thr Gln Ala Ile Ser Val Leu His Glu Met Ile Gln Gln
    50                  55                  60

Thr Phe Asn Leu Phe Ser Thr Glu Asp Ser Ser Ala Ala Trp Glu Gln
65                  70                  75                  80

Ser Leu Leu Glu Lys Phe Ser Thr Glu Leu Tyr Gln Gln Leu Asn Asn
                85                  90                  95

Leu Glu Ala Cys Val Ile Gln Glu Val Gly Met Glu Glu Thr Pro Leu
            100                 105                 110

Met Asn Glu Asp Ser Ile Leu Ala Val Arg Lys Tyr Phe Gln Arg Ile
        115                 120                 125

Thr Leu Tyr Leu Thr Glu Lys Lys Tyr Ser Pro Cys Ala Trp Glu Val
    130                 135                 140

Val Arg Ala Glu Ile Met Arg Ser Leu Ser Phe Ser Thr Asn Leu Gln
145                 150                 155                 160

Lys Ile Leu Arg Arg Lys Asp
                165

<210> SEQ ID NO 52
<211> LENGTH: 167
<212> TYPE: PRT
<213> ORGANISM: Homo sapiens

<400> SEQUENCE: 52

Met Cys Asp Leu Pro Gln Thr His Ser Leu Arg Asn Arg Arg Ala Leu
1               5                   10                  15

Ile Leu Leu Ala Gln Met Gly Arg Ile Ser Pro Phe Ser Cys Leu Lys
            20                  25                  30

Asp Arg His Glu Phe Arg Phe Pro Glu Glu Glu Phe Asp Gly His Gln
        35                  40                  45

Phe Gln Lys Thr Gln Ala Ile Ser Val Leu His Glu Met Ile Gln Gln
    50                  55                  60

Thr Phe Asn Leu Phe Ser Thr Glu Asp Ser Ser Ala Ala Trp Glu Gln
65                  70                  75                  80

Ser Leu Leu Glu Lys Phe Ser Thr Glu Leu Tyr Gln Gln Leu Asn Asp
                85                  90                  95

Leu Glu Ala Cys Val Ile Gln Glu Val Gly Val Glu Glu Thr Pro Leu
            100                 105                 110

Met Asn Glu Asp Phe Ile Leu Ala Val Arg Lys Tyr Phe Gln Arg Ile
        115                 120                 125

Thr Leu Tyr Leu Met Glu Lys Lys Tyr Ser Pro Cys Ala Trp Glu Val
    130                 135                 140

Val Arg Ala Glu Ile Met Arg Ser Phe Ser Phe Ser Thr Asn Leu Lys
145                 150                 155                 160

Lys Gly Leu Arg Arg Lys Asp
                165

<210> SEQ ID NO 53

```
<211> LENGTH: 166
<212> TYPE: PRT
<213> ORGANISM: Homo sapiens

<400> SEQUENCE: 53

Met Cys Asp Leu Pro Gln Thr His Ser Leu Gly Ser Arg Arg Thr Leu
1               5                   10                  15
Met Leu Leu Ala Gln Met Arg Arg Ile Ser Leu Phe Ser Cys Leu Lys
                20                  25                  30
Asp Arg His Asp Phe Gly Phe Pro Gln Glu Glu Phe Gly Asn Gln Phe
            35                  40                  45
Gln Lys Ala Glu Thr Ile Pro Val Leu His Glu Met Ile Gln Gln Ile
        50                  55                  60
Phe Asn Leu Phe Ser Thr Lys Asp Ser Ser Ala Ala Trp Asp Glu Thr
65                  70                  75                  80
Leu Leu Asp Lys Phe Tyr Thr Glu Leu Tyr Gln Gln Leu Asn Asp Leu
                85                  90                  95
Glu Ala Cys Val Ile Gln Gly Val Gly Val Thr Glu Thr Pro Leu Met
            100                 105                 110
Lys Glu Asp Ser Ile Leu Ala Val Arg Lys Tyr Phe Gln Arg Ile Thr
        115                 120                 125
Leu Tyr Leu Lys Glu Lys Lys Tyr Ser Pro Cys Ala Trp Glu Val Val
130                 135                 140
Arg Ala Glu Ile Met Arg Ser Phe Ser Leu Ser Thr Asn Leu Gln Glu
145                 150                 155                 160
Ser Leu Arg Ser Lys Glu
                165

<210> SEQ ID NO 54
<211> LENGTH: 167
<212> TYPE: PRT
<213> ORGANISM: Homo sapiens

<400> SEQUENCE: 54

Met Cys Asp Leu Pro Gln Thr His Ser Leu Gly Asn Arg Arg Ala Leu
1               5                   10                  15
Ile Leu Leu Gly Gln Met Gly Arg Ile Ser Pro Phe Ser Cys Leu Lys
                20                  25                  30
Asp Arg His Asp Phe Arg Ile Pro Gln Glu Glu Phe Asp Gly Asn Gln
            35                  40                  45
Phe Gln Lys Ala Gln Ala Ile Ser Val Leu His Glu Met Ile Gln Gln
        50                  55                  60
Thr Phe Asn Leu Phe Ser Thr Glu Asp Ser Ser Ala Ala Trp Glu Gln
65                  70                  75                  80
Ser Leu Leu Glu Lys Phe Ser Thr Glu Ile Tyr Gln Gln Leu Asn Asp
                85                  90                  95
Leu Glu Ala Cys Val Ile Gln Glu Val Gly Val Glu Glu Thr Pro Leu
            100                 105                 110
Met Asn Glu Asp Ser Ile Leu Ala Val Arg Lys Tyr Phe Gln Arg Ile
        115                 120                 125
Thr Leu Tyr Leu Ile Glu Arg Lys Tyr Ser Pro Cys Ala Trp Glu Val
130                 135                 140
Val Arg Ala Glu Ile Met Arg Ser Leu Ser Phe Ser Thr Asn Leu Gln
145                 150                 155                 160
Lys Arg Leu Arg Arg Lys Asp
                165
```

<210> SEQ ID NO 55
<211> LENGTH: 167
<212> TYPE: PRT
<213> ORGANISM: Homo sapiens

<400> SEQUENCE: 55

Met Cys Asn Leu Ser Gln Thr His Ser Leu Asn Asn Arg Arg Thr Leu
1               5                   10                  15

Met Leu Met Ala Gln Met Arg Arg Ile Ser Pro Phe Ser Cys Leu Lys
            20                  25                  30

Asp Arg His Asp Phe Glu Phe Pro Gln Glu Glu Phe Asp Gly Asn Gln
        35                  40                  45

Phe Gln Lys Ala Gln Ala Ile Ser Val Leu His Glu Met Met Gln Gln
    50                  55                  60

Thr Phe Asn Leu Phe Ser Thr Lys Asn Ser Ser Ala Ala Trp Asp Glu
65                  70                  75                  80

Thr Leu Leu Glu Lys Phe Tyr Ile Glu Leu Phe Gln Gln Met Asn Asp
                85                  90                  95

Leu Glu Ala Cys Val Ile Gln Glu Val Gly Val Glu Glu Thr Pro Leu
            100                 105                 110

Met Asn Glu Asp Ser Ile Leu Ala Val Arg Lys Tyr Phe Gln Arg Ile
        115                 120                 125

Thr Leu Tyr Leu Met Glu Lys Lys Tyr Ser Pro Cys Ala Trp Glu Val
    130                 135                 140

Val Arg Ala Glu Ile Met Arg Ser Leu Ser Phe Ser Thr Asn Leu Gln
145                 150                 155                 160

Lys Arg Leu Arg Arg Lys Asp
                165

<210> SEQ ID NO 56
<211> LENGTH: 167
<212> TYPE: PRT
<213> ORGANISM: Homo sapiens

<400> SEQUENCE: 56

Met Cys Asn Leu Ser Gln Thr His Ser Leu Asn Asn Arg Arg Thr Leu
1               5                   10                  15

Met Leu Met Ala Gln Met Arg Arg Ile Ser Pro Phe Ser Cys Leu Lys
            20                  25                  30

Asp Arg His Asp Phe Glu Phe Pro Gln Glu Glu Phe Asp Gly Asn Gln
        35                  40                  45

Phe Gln Lys Ala Gln Ala Ile Ser Val Leu His Glu Met Met Gln Gln
    50                  55                  60

Thr Phe Asn Leu Phe Ser Thr Lys Asn Ser Ser Ala Ala Trp Asp Glu
65                  70                  75                  80

Thr Leu Leu Glu Lys Phe Tyr Ile Glu Leu Phe Gln Gln Met Asn Asp
                85                  90                  95

Leu Glu Ala Cys Val Ile Gln Glu Val Gly Val Glu Glu Thr Pro Leu
            100                 105                 110

Met Asn Glu Asp Ser Ile Leu Ala Val Lys Lys Tyr Phe Gln Arg Ile
        115                 120                 125

Thr Leu Tyr Leu Met Glu Lys Lys Tyr Ser Pro Cys Ala Trp Glu Val
    130                 135                 140

Val Arg Ala Glu Ile Met Arg Ser Phe Ser Phe Ser Thr Asn Leu Gln
145                 150                 155                 160

```
Lys Arg Leu Arg Arg Lys Asp
                165

<210> SEQ ID NO 57
<211> LENGTH: 167
<212> TYPE: PRT
<213> ORGANISM: Homo sapiens

<400> SEQUENCE: 57

Met Cys Asp Leu Pro Gln Thr His Thr Leu Arg Asn Arg Arg Ala Leu
 1               5                  10                  15

Ile Leu Leu Gly Gln Met Gly Arg Ile Ser Pro Phe Ser Cys Leu Lys
                20                  25                  30

Asp Arg His Asp Phe Arg Ile Pro Gln Glu Glu Phe Asp Gly Asn Gln
            35                  40                  45

Phe Gln Lys Ala Gln Ala Ile Ser Val Leu His Glu Met Ile Gln Gln
        50                  55                  60

Thr Phe Asn Leu Phe Ser Thr Glu Asp Ser Ser Ala Ala Trp Glu Gln
65                  70                  75                  80

Ser Leu Leu Glu Lys Phe Ser Thr Glu Ile Tyr Gln Gln Leu Asn Asp
                85                  90                  95

Leu Glu Ala Cys Val Ile Gln Glu Val Gly Val Glu Thr Pro Leu
                100                 105                 110

Met Asn Glu Asp Ser Ile Leu Ala Val Arg Lys Tyr Phe Gln Arg Ile
            115                 120                 125

Thr Leu Tyr Leu Ile Glu Arg Lys Tyr Ser Pro Cys Ala Trp Glu Val
        130                 135                 140

Val Arg Ala Glu Ile Met Arg Ser Leu Ser Phe Ser Thr Asn Leu Gln
145                 150                 155                 160

Lys Arg Leu Arg Arg Lys Asp
                165

<210> SEQ ID NO 58
<211> LENGTH: 167
<212> TYPE: PRT
<213> ORGANISM: Homo sapiens

<400> SEQUENCE: 58

Met Cys Asn Leu Ser Gln Thr His Ser Leu Asn Asn Arg Arg Thr Leu
 1               5                  10                  15

Met Leu Met Ala Gln Met Arg Arg Ile Ser Pro Phe Ser Cys Leu Lys
                20                  25                  30

Asp Arg His Asp Phe Glu Phe Pro Gln Glu Glu Phe Asp Gly Asn Gln
            35                  40                  45

Phe Gln Lys Ala Gln Ala Ile Ser Val Leu His Glu Met Met Gln Gln
        50                  55                  60

Thr Phe Asn Leu Phe Ser Thr Lys Asn Ser Ser Ala Ala Trp Asp Glu
65                  70                  75                  80

Thr Leu Leu Glu Lys Phe Tyr Ile Glu Leu Phe Gln Gln Met Asn Asp
                85                  90                  95

Leu Glu Ala Cys Val Ile Gln Val Gly Val Glu Thr Pro Leu
                100                 105                 110

Met Asn Glu Asp Ser Ile Leu Ala Val Lys Lys Tyr Phe Gln Arg Ile
            115                 120                 125

Thr Leu Tyr Leu Met Glu Lys Lys Tyr Ser Pro Cys Ala Trp Glu Val
        130                 135                 140
```

Val Arg Ala Glu Ile Met Arg Ser Leu Ser Phe Ser Thr Asn Leu Gln
145                 150                 155                 160

Lys Arg Leu Arg Arg Lys Asp
                165

<210> SEQ ID NO 59
<211> LENGTH: 167
<212> TYPE: PRT
<213> ORGANISM: Homo sapiens

<400> SEQUENCE: 59

Met Cys Asp Leu Pro Gln Thr His Ser Leu Gly Asn Arg Arg Ala Leu
1               5                   10                  15

Ile Leu Leu Ala Gln Met Gly Arg Ile Ser Pro Phe Ser Cys Leu Lys
                20                  25                  30

Asp Arg Pro Asp Phe Gly Leu Pro Gln Glu Glu Phe Asp Gly Asn Gln
            35                  40                  45

Phe Gln Lys Thr Gln Ala Ile Ser Val Leu His Glu Met Ile Gln Gln
        50                  55                  60

Thr Phe Asn Leu Phe Ser Thr Glu Asp Ser Ser Ala Ala Trp Glu Gln
65                  70                  75                  80

Ser Leu Leu Glu Lys Phe Ser Thr Glu Leu Tyr Gln Gln Leu Asn Asn
                85                  90                  95

Leu Glu Ala Cys Val Ile Gln Gly Val Gly Met Glu Glu Thr Pro Leu
            100                 105                 110

Met Asn Glu Asp Ser Ile Leu Ala Val Arg Lys Tyr Phe Gln Arg Ile
        115                 120                 125

Thr Leu Tyr Leu Thr Glu Lys Lys Tyr Ser Pro Ser Ala Trp Glu Val
    130                 135                 140

Val Arg Ala Glu Ile Met Arg Ser Leu Ser Phe Ser Thr Asn Leu Gln
145                 150                 155                 160

Lys Ile Leu Arg Arg Lys Asp
                165

<210> SEQ ID NO 60

<400> SEQUENCE: 60

000

<210> SEQ ID NO 61

<400> SEQUENCE: 61

000

<210> SEQ ID NO 62
<211> LENGTH: 15
<212> TYPE: PRT
<213> ORGANISM: Homo sapiens

<400> SEQUENCE: 62

Asp Asp Ala Ala Asp Leu Gln Pro Leu Gln His Lys Gly Leu Ile
1               5                   10                  15

<210> SEQ ID NO 63
<211> LENGTH: 8
<212> TYPE: PRT
<213> ORGANISM: Homo sapiens

-continued

```
<400> SEQUENCE: 63

Asp Pro Phe Arg Gln Ile Leu His
1               5

<210> SEQ ID NO 64
<211> LENGTH: 6
<212> TYPE: PRT
<213> ORGANISM: Homo sapiens

<400> SEQUENCE: 64

Thr Leu Pro Ala Ala Glu
1               5

<210> SEQ ID NO 65
<211> LENGTH: 41
<212> TYPE: PRT
<213> ORGANISM: Homo sapiens

<400> SEQUENCE: 65

Pro Gly Ser Leu Cys Asp Val Glu Gly Trp Ser Gly Arg Asp Ser Pro
1               5                   10                  15

Glu Glu Cys Gly Leu His Pro Gly Cys Glu Lys Ile Leu Ser Lys Asn
            20                  25                  30

His Ser Leu Ser Asp Lys Glu Glu Val
        35                  40

<210> SEQ ID NO 66
<211> LENGTH: 29
<212> TYPE: PRT
<213> ORGANISM: Homo sapiens

<400> SEQUENCE: 66

Pro Leu Phe Leu Gly Gly Cys Gln Ser Arg Asn His Glu Ile Leu Leu
1               5                   10                  15

Phe Met Asn Glu Leu Ala Gly Lys Ile Lys Glu Glu Gly
            20                  25

<210> SEQ ID NO 67
<211> LENGTH: 52
<212> TYPE: PRT
<213> ORGANISM: Homo sapiens

<400> SEQUENCE: 67

Lys Val Gly Val Glu Glu Thr Pro Leu Arg Asn Val Asp Ser Ile Leu
1               5                   10                  15

Ala Val Arg Lys Tyr Phe Gln Arg Ile Thr Leu Tyr Leu Thr Lys Lys
            20                  25                  30

Lys Tyr Ser Pro Cys Ser Trp Glu Ala Val Arg Ala Glu Ile Met Arg
        35                  40                  45

Ser Phe Ser Leu
    50

<210> SEQ ID NO 68
<211> LENGTH: 11
<212> TYPE: PRT
<213> ORGANISM: Homo sapiens

<400> SEQUENCE: 68

Thr Asn Leu Gln Glu Arg Leu Arg Arg Lys Glu
1               5                   10
```

-continued

```
<210> SEQ ID NO 69
<211> LENGTH: 19
<212> TYPE: PRT
<213> ORGANISM: Homo sapiens

<400> SEQUENCE: 69

Met Ala Leu Ser Phe Ser Leu Leu Met Ala Val Leu Val Leu Ser Tyr
1               5                   10                  15

Lys Ser Ile

<210> SEQ ID NO 70
<211> LENGTH: 19
<212> TYPE: PRT
<213> ORGANISM: Homo sapiens

<400> SEQUENCE: 70

Met Ala Leu Ser Phe Ser Leu Leu Met Ala Val Leu Val Leu Ser Tyr
1               5                   10                  15

Lys Ser Ile

<210> SEQ ID NO 71
<211> LENGTH: 165
<212> TYPE: PRT
<213> ORGANISM: Homo sapiens

<400> SEQUENCE: 71

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 72
<211> LENGTH: 166
<212> TYPE: PRT
<213> ORGANISM: Homo sapiens

<400> SEQUENCE: 72

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30
```

```
Arg His Asp Phe Glu Phe Pro Gln Glu Glu Phe Asp Asp Lys Gln Phe
            35                  40                  45
Gln Lys Ala Gln Ala Ile Ser Val Leu His Glu Met Ile Gln Gln Thr
         50                  55                  60
Phe Asn Leu Phe Ser Thr Lys Asp Ser Ser Ala Ala Leu Asp Glu Thr
65                  70                  75                  80
Leu Leu Asp Glu Phe Tyr Ile Glu Leu Asp Gln Gln Leu Asn Asp Leu
                85                  90                  95
Glu Val Leu Cys Asp Gln Glu Val Gly Val Ile Glu Ser Pro Leu Met
                100                 105                 110
Tyr Glu Asp Ser Ile Leu Ala Val Arg Lys Tyr Phe Gln Arg Ile Thr
            115                 120                 125
Leu Tyr Leu Thr Glu Lys Lys Tyr Ser Ser Cys Ala Trp Glu Val Val
        130                 135                 140
Arg Ala Glu Ile Met Arg Ser Phe Ser Leu Ser Ile Asn Leu Gln Lys
145                 150                 155                 160
Arg Leu Lys Ser Lys Glu
                165

<210> SEQ ID NO 73
<211> LENGTH: 166
<212> TYPE: PRT
<213> ORGANISM: Homo sapiens

<400> SEQUENCE: 73

Cys Asp Leu Pro Gln Thr His Ser Leu Gly Asn Arg Arg Ala Leu Ile
1               5                   10                  15
Leu Leu Gly Gln Met Gly Arg Ile Ser Pro Phe Ser Cys Leu Lys Asp
                20                  25                  30
Arg His Asp Phe Arg Ile Pro Gln Glu Glu Phe Asp Gly Asn Gln Phe
            35                  40                  45
Gln Lys Ala Gln Ala Ile Ser Val Leu His Glu Met Ile Gln Gln Thr
         50                  55                  60
Phe Asn Leu Phe Ser Thr Glu Asp Ser Ser Ala Ala Trp Glu Gln Ser
65                  70                  75                  80
Leu Leu Glu Lys Phe Ser Thr Glu Leu Tyr Gln Gln Leu Asn Asp Leu
                85                  90                  95
Glu Ala Cys Val Ile Gln Glu Val Gly Val Glu Glu Thr Pro Leu Met
                100                 105                 110
Asn Glu Asp Ser Ile Leu Ala Val Arg Lys Tyr Phe Gln Arg Ile Thr
            115                 120                 125
Leu Tyr Leu Ile Glu Arg Lys Tyr Ser Pro Cys Ala Trp Glu Val Val
        130                 135                 140
Arg Ala Glu Ile Met Arg Ser Leu Ser Phe Ser Thr Asn Leu Gln Lys
145                 150                 155                 160
Arg Leu Arg Arg Lys Asp
                165

<210> SEQ ID NO 74
<211> LENGTH: 166
<212> TYPE: PRT
<213> ORGANISM: Homo sapiens

<400> SEQUENCE: 74

Cys Asp Leu Pro Glu Thr His Ser Leu Asp Asn Arg Arg Thr Leu Met
1               5                   10                  15
```

```
Leu Leu Ala Gln Met Ser Arg Ile Ser Pro Ser Ser Cys Leu Met Asp
             20                  25                  30

Arg His Asp Phe Gly Phe Pro Gln Glu Glu Phe Asp Gly Asn Gln Phe
             35                  40                  45

Gln Lys Ala Pro Ala Ile Ser Val Leu His Glu Leu Ile Gln Gln Ile
         50                  55                  60

Phe Asn Leu Phe Thr Thr Lys Asp Ser Ser Ala Ala Trp Asp Glu Asp
 65                  70                  75                  80

Leu Leu Asp Lys Phe Cys Thr Glu Leu Tyr Gln Gln Leu Asn Asp Leu
             85                  90                  95

Glu Ala Cys Val Met Gln Glu Glu Arg Val Gly Glu Thr Pro Leu Met
            100                 105                 110

Asn Val Asp Ser Ile Leu Ala Val Lys Lys Tyr Phe Arg Arg Ile Thr
            115                 120                 125

Leu Tyr Leu Thr Glu Lys Lys Tyr Ser Pro Cys Ala Trp Glu Val Val
            130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 75
<211> LENGTH: 166
<212> TYPE: PRT
<213> ORGANISM: Homo sapiens

<400> SEQUENCE: 75

Cys Asp Leu Pro Gln Thr His Ser Leu Gly Asn Arg Arg Ala Leu Ile
 1               5                  10                  15

Leu Leu Ala Gln Met Gly Arg Ile Ser Pro Phe Ser Cys Leu Lys Asp
             20                  25                  30

Arg His Asp Phe Gly Phe Pro Gln Glu Glu Phe Asp Gly Asn Gln Phe
             35                  40                  45

Gln Lys Ala Gln Ala Ile Ser Val Leu His Glu Met Ile Gln Gln Thr
         50                  55                  60

Phe Asn Leu Phe Ser Thr Lys Asp Ser Ser Ala Thr Trp Glu Gln Ser
 65                  70                  75                  80

Leu Leu Glu Lys Phe Ser Thr Glu Leu Asn Gln Gln Leu Asn Asp Met
             85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
            115                 120                 125

Leu Tyr Leu Thr Glu Lys Lys Tyr Ser Pro Cys Ala Trp Glu Val Val
            130                 135                 140

Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 76
<211> LENGTH: 166
<212> TYPE: PRT
<213> ORGANISM: Homo sapiens

<400> SEQUENCE: 76
```

Cys Asn Leu Ser Gln Thr His Ser Leu Asn Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Glu Phe Pro Gln Glu Glu Phe Asp Gly Asn Gln Phe
            35                  40                  45

Gln Lys Ala Gln Ala Ile Ser Val Leu His Glu Met Met Gln Gln Thr
        50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
                100                 105                 110

Asn Glu Asp Ser Ile Leu Ala Val Arg Lys Tyr Phe Gln Arg Ile Thr
                115                 120                 125

Leu Tyr Leu Met Glu Lys Lys Tyr Ser Pro Cys Ala Trp Glu Val Val
            130                 135                 140

Arg Ala Glu Ile Met Arg Ser Phe Ser Phe Ser Thr Asn Leu Gln Lys
145                 150                 155                 160

Arg Leu Arg Arg Lys Asp
                165

<210> SEQ ID NO 77
<211> LENGTH: 166
<212> TYPE: PRT
<213> ORGANISM: Homo sapiens

<400> SEQUENCE: 77

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg Pro Asp Phe Gly Leu Pro Gln Glu Glu Phe Asp Gly Asn Gln Phe
            35                  40                  45

Gln Lys Thr Gln Ala Ile Ser Val Leu His Glu Met Ile Gln Gln Thr
        50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asn Leu
                85                  90                  95

Glu Ala Cys Val Ile Gln Glu Val Gly Met Glu Glu Thr Pro Leu Met
                100                 105                 110

Asn Glu Asp Ser Ile Leu Ala Val Arg Lys Tyr Phe Gln Arg Ile Thr
                115                 120                 125

Leu Tyr Leu Thr Glu Lys Lys Tyr Ser Pro Cys Ala Trp Glu Val Val
            130                 135                 140

Arg Ala Glu Ile Met Arg Ser Leu Ser Phe Ser Thr Asn Leu Gln Lys
145                 150                 155                 160

Ile Leu Arg Arg Lys Asp
                165

<210> SEQ ID NO 78
<211> LENGTH: 166
<212> TYPE: PRT

```
<213> ORGANISM: Homo sapiens

<400> SEQUENCE: 78

Cys Asp Leu Pro Gln Thr His Ser Leu Arg Asn Arg Ala Leu Ile
1               5                   10                  15

Leu Leu Ala Gln Met Gly Arg Ile Ser Pro Phe Ser Cys Leu Lys Asp
            20                  25                  30

Arg His Glu Phe Arg Phe Pro Glu Glu Phe Asp Gly His Gln Phe
            35                  40                  45

Gln Lys Thr Gln Ala Ile Ser Val Leu His Glu Met Ile Gln Gln Thr
        50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Thr Pro Leu Met
                100                 105                 110

Asn Glu Asp Phe Ile Leu Ala Val Arg Lys Tyr Phe Gln Arg Ile Thr
            115                 120                 125

Leu Tyr Leu Met Glu Lys Lys Tyr Ser Pro Cys Ala Trp Glu Val Val
    130                 135                 140

Arg Ala Glu Ile Met Arg Ser Phe Ser Phe Ser Thr Asn Leu Lys Lys
145                 150                 155                 160

Gly Leu Arg Arg Lys Asp
                165

<210> SEQ ID NO 79
<211> LENGTH: 165
<212> TYPE: PRT
<213> ORGANISM: Homo sapiens

<400> SEQUENCE: 79

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
        50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

```
<210> SEQ ID NO 80
<211> LENGTH: 166
<212> TYPE: PRT
<213> ORGANISM: Homo sapiens

<400> SEQUENCE: 80

Cys Asp Leu Pro Gln Thr His Ser Leu Gly Asn Arg Arg Ala Leu Ile
1               5                   10                  15

Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Ile Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Ile Glu Arg Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 81
<211> LENGTH: 166
<212> TYPE: PRT
<213> ORGANISM: Homo sapiens

<400> SEQUENCE: 81

Cys Asn Leu Ser Gln Thr His Ser Leu Asn Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Glu Phe Pro Gln Glu Glu Phe Asp Gly Asn Gln Phe
        35                  40                  45

Gln Lys Ala Gln Ala Ile Ser Val Leu His Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
```

165

<210> SEQ ID NO 82
<211> LENGTH: 166
<212> TYPE: PRT
<213> ORGANISM: Homo sapiens

<400> SEQUENCE: 82

```
Cys Asn Leu Ser Gln Thr His Ser Leu Asn Asn Arg Thr Leu Met
1               5                   10                  15

Leu Met Ala Gln Met Arg Arg Ile Ser Pro Phe Ser Cys Leu Lys Asp
                20                  25                  30

Arg His Asp Phe Glu Phe Pro Gln Glu Glu Phe Asp Gly Asn Gln Phe
            35                  40                  45

Gln Lys Ala Gln Ala Ile Ser Val Leu His Glu Met Met Gln Gln Thr
        50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Lys Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Asp
                165
```

<210> SEQ ID NO 83
<211> LENGTH: 166
<212> TYPE: PRT
<213> ORGANISM: Homo sapiens

<400> SEQUENCE: 83

```
Cys Asp Leu Pro Gln Thr His Thr Leu Arg Asn Arg Arg Ala Leu Ile
1               5                   10                  15

Leu Leu Gly Gln Met Gly Arg Ile Ser Pro Phe Ser Cys Leu Lys Asp
                20                  25                  30

Arg His Asp Phe Arg Ile Pro Gln Glu Glu Phe Asp Gly Asn Gln Phe
            35                  40                  45

Gln Lys Ala Gln Ala Ile Ser Val Leu His Glu Met Ile Gln Gln Thr
        50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Ile Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Ile Glu Arg Lys Tyr Ser Pro Cys Ala Trp Glu Val Val
    130                 135                 140

Arg Ala Glu Ile Met Arg Ser Leu Ser Phe Ser Thr Asn Leu Gln Lys
```

-continued

```
145                 150                 155                 160
Arg Leu Arg Arg Lys Asp
                165

<210> SEQ ID NO 84
<211> LENGTH: 166
<212> TYPE: PRT
<213> ORGANISM: Homo sapiens

<400> SEQUENCE: 84

Cys Asn Leu Ser Gln Thr His Ser Leu Asn Asn Arg Thr Leu Met
1               5                   10                  15

Leu Met Ala Gln Met Arg Arg Ile Ser Pro Phe Ser Cys Leu Lys Asp
                20                  25                  30

Arg His Asp Phe Glu Phe Pro Gln Glu Glu Phe Asp Gly Asn Gln Phe
                35                  40                  45

Gln Lys Ala Gln Ala Ile Ser Val Leu His Glu Met Met Gln Gln Thr
        50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
                100                 105                 110

Asn Glu Asp Ser Ile Leu Ala Val Lys Lys Tyr Phe Gln Arg Ile Thr
            115                 120                 125

Leu Tyr Leu Met Glu Lys Lys Tyr Ser Pro Cys Ala Trp Glu Val Val
        130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 85
<211> LENGTH: 166
<212> TYPE: PRT
<213> ORGANISM: Homo sapiens

<400> SEQUENCE: 85

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
                20                  25                  30

Arg Pro Asp Phe Gly Leu Pro Gln Glu Glu Phe Asp Gly Asn Gln Phe
                35                  40                  45

Gln Lys Thr Gln Ala Ile Ser Val Leu His Glu Met Ile Gln Gln Thr
        50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asn Leu
                85                  90                  95

Glu Ala Cys Val Ile Gln Glu Val Gly Met Glu Glu Thr Pro Leu Met
                100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Ser Ala Trp Glu Val Val
```

```
                  130                 135                 140
Arg Ala Glu Ile Met Arg Ser Leu Ser Phe Ser Thr Asn Leu Gln Lys
145                 150                 155                 160

Ile Leu Arg Arg Lys Asp
                165
```